US012616366B2

(12) United States Patent
Lee et al.

(10) Patent No.: US 12,616,366 B2
(45) Date of Patent: May 5, 2026

(54) SYSTEMS AND METHODS FOR EVALUATING EYE MOVEMENT DISORDERS THROUGH EYE-TRACKING EXERCISES

(71) Applicant: Zenni Optical, Inc., Novato, CA (US)

(72) Inventors: Steven Lee, Barrington, IL (US); Julia Zhen, Novato, CA (US); ChyrSong Ting, Novato, CA (US); Matthew James Golino, Brookhaven, GA (US); Justin Paul Dempsey, Ottawa (CA); Jeffrey Joseph Fillingham, Dartmouth (CA)

(73) Assignee: Zenni Optical, Inc., Novato, CA (US)

( * ) Notice: Subject to any disclaimer, the term of this patent is extended or adjusted under 35 U.S.C. 154(b) by 0 days.

(21) Appl. No.: 18/811,713

(22) Filed: Aug. 21, 2024

(65) Prior Publication Data

US 2026/0053344 A1 Feb. 26, 2026

(51) Int. Cl.
| | |
|---|---|
| *A61B 3/02* | (2006.01) |
| *A61B 3/00* | (2006.01) |
| *A61B 3/14* | (2006.01) |
| *G16H 50/70* | (2018.01) |

(52) U.S. Cl.
CPC ................ *A61B 3/02* (2013.01); *A61B 3/005* (2013.01); *A61B 3/14* (2013.01); *G16H 50/70* (2018.01)

(58) Field of Classification Search
CPC .. A61B 3/02; A61B 3/005; A61B 3/14; G16H 50/70; G06F 3/013
See application file for complete search history.

(56) References Cited

U.S. PATENT DOCUMENTS

| | | | |
|---|---|---|---|
| 2,352,500 | A | 6/1944 | Shepard |
| 4,861,156 | A | 8/1989 | Terry |
| 5,737,060 | A | 4/1998 | Kasha, Jr. |
| 5,767,940 | A | 6/1998 | Hayashi et al. |
| 6,592,222 | B2 | 7/2003 | Massengill et al. |

(Continued)

FOREIGN PATENT DOCUMENTS

| | | |
|---|---|---|
| CN | 2904944 Y | 5/2007 |
| CN | 109431445 A | 3/2019 |

(Continued)

*Primary Examiner* — Stephen G Sherman
(74) *Attorney, Agent, or Firm* — Morgan, Lewis & Bockius LLP

(57) ABSTRACT

A patient's visual health can be evaluated via a virtual reality (VR) system, which includes a VR headset in electronic communication with a computing device. The computing device causes virtual environments, which can include objects, to be displayed on the VR headset. Using varying combinations of eye-tracking sensors, eye-tracking cameras, motion-tracking sensors, handheld devices, and microphones, the VR headset collects data about the patient as she tracks the objects as the objects are displayed in different positions in the virtual environments. Optionally, advanced algorithms in the computing device dynamically alter the positions of the objects and analyze the patient's eye-tracking to evaluate the patient for eye movement disorders. This dynamic evaluation can facilitate a wider scope of testing and a more detailed assessment of the patient's ocular health, as compared to traditional ocular evaluation methods.

17 Claims, 25 Drawing Sheets

(56)            References Cited

U.S. PATENT DOCUMENTS

| | | | |
|---|---|---|---|
| 7,784,948 B2 | 8/2010 | Nozawa et al. | |
| 10,238,280 B2 | 3/2019 | Maeda et al. | |
| 10,610,093 B2 | 4/2020 | Green | |
| 11,426,107 B2 | 8/2022 | Gibbons et al. | |
| 11,633,097 B1 | 4/2023 | Ziff et al. | |
| 11,768,594 B2 | 9/2023 | Cameron | |
| 11,793,403 B2 | 10/2023 | Tran et al. | |
| 11,857,331 B1* | 1/2024 | Berme | A61B 5/1038 |
| 12,210,149 B2 | 1/2025 | Jin et al. | |
| 2016/0270656 A1* | 9/2016 | Samec | A61B 3/1035 |
| 2019/0008441 A1 | 1/2019 | Guzik | |
| 2019/0298166 A1 | 10/2019 | Smith et al. | |
| 2019/0328305 A1 | 10/2019 | Wood et al. | |
| 2019/0350452 A1 | 11/2019 | Lewis | |
| 2020/0104999 A1* | 4/2020 | Edell | G06V 40/161 |
| 2021/0255485 A1* | 8/2021 | Xu | G06F 3/011 |
| 2022/0071483 A1* | 3/2022 | Abitbol | G09G 3/001 |
| 2022/0354413 A1 | 11/2022 | Rah | |
| 2024/0428539 A1* | 12/2024 | Stauber | G06F 1/1671 |

FOREIGN PATENT DOCUMENTS

| | | | | | |
|---|---|---|---|---|---|
| GR | 1005651 | B | 9/2007 | | |
| HU | 185600 | B | 2/1985 | | |
| JP | H0626538 | B2 | 4/1994 | | |
| JP | 2721892 | B2 | 3/1998 | | |
| JP | 2000079095 | A | 3/2000 | | |
| JP | 2001275968 | A | 10/2001 | | |
| JP | 2001286442 | A | 10/2001 | | |
| JP | 3259920 | B2 | 2/2002 | | |
| JP | 2002051981 | A | 2/2002 | | |
| JP | 2003038440 | A | 2/2003 | | |
| JP | 2003079574 | A | 3/2003 | | |
| JP | 2012100758 | A | 5/2012 | | |
| JP | 5007435 | B2 | 8/2012 | | |
| KR | 20240081765 | A * | 6/2024 | | A61B 90/39 |
| RU | 2723598 | C1 | 6/2020 | | |
| WO | 1994013192 | A1 | 6/1994 | | |
| WO | 2011022428 | A2 | 2/2011 | | |
| WO | 2016165272 | A1 | 10/2016 | | |
| WO | 2017070704 | A2 | 4/2017 | | |
| WO | 2021018224 | A1 | 2/2021 | | |
| WO | 2022111663 | A1 | 6/2022 | | |

* cited by examiner

650

700

702

704

702

810

820

830

842

840

844

910
912    914
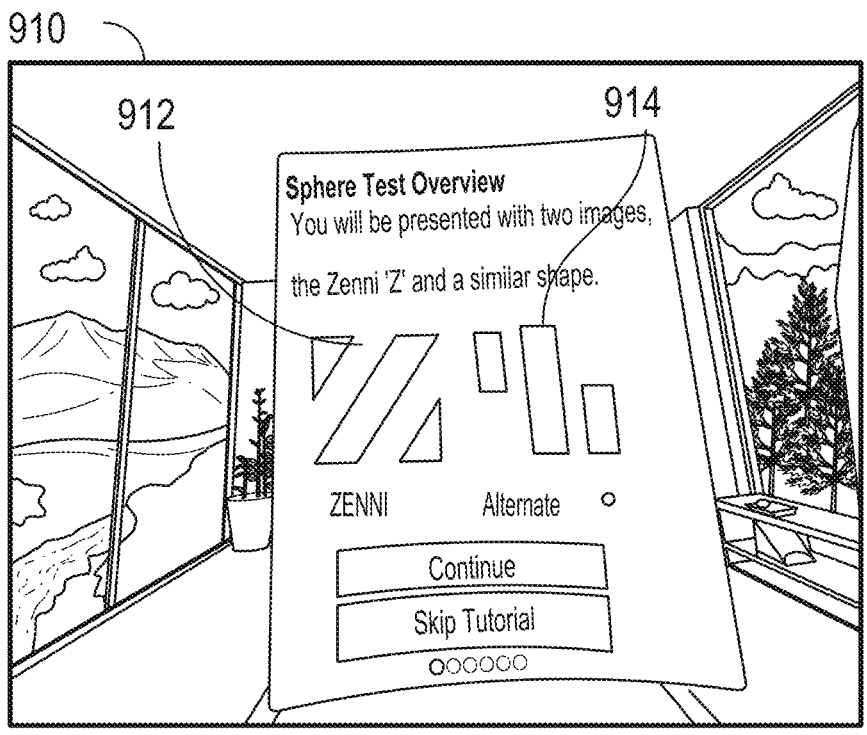
FIG. 9A
920
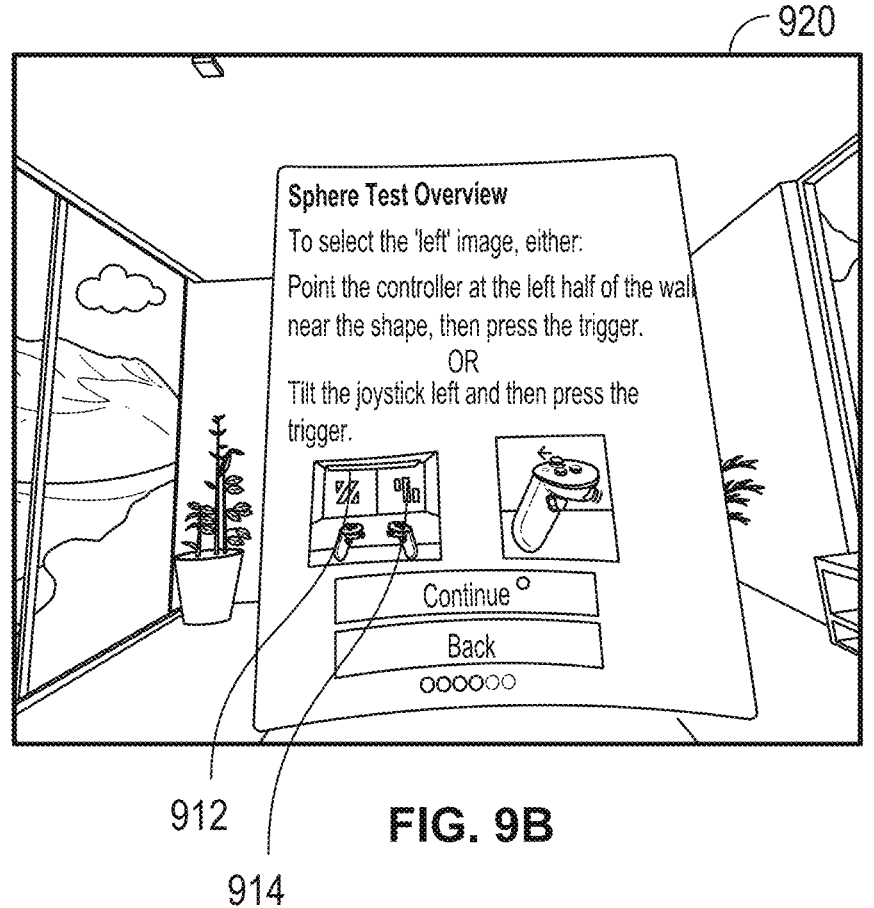
912
914    FIG. 9B

1050

1060

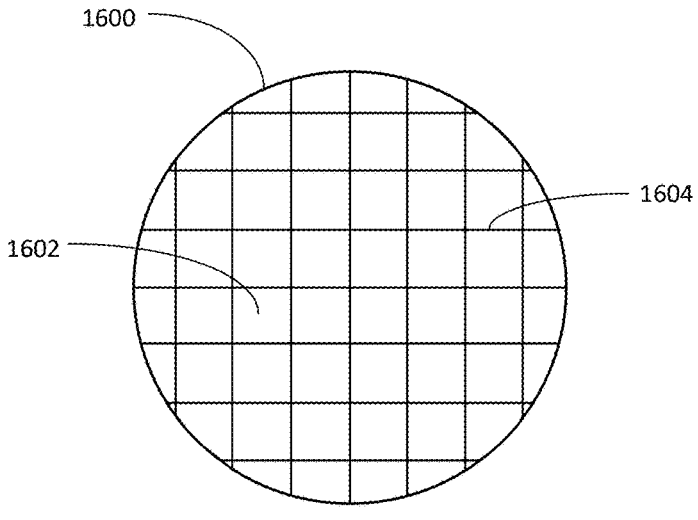
FIG. 16A
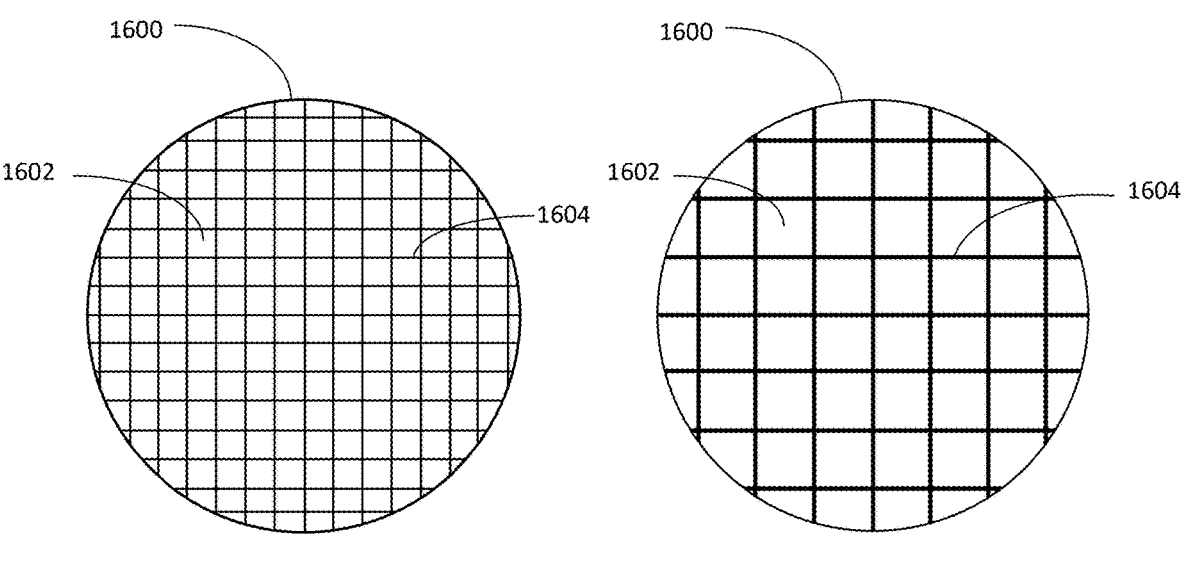
FIG. 16B            FIG. 16C

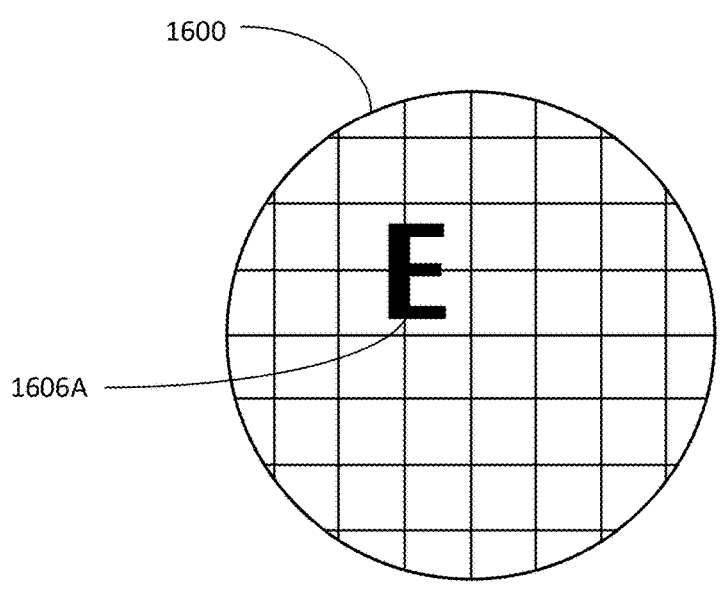
FIG. 16D
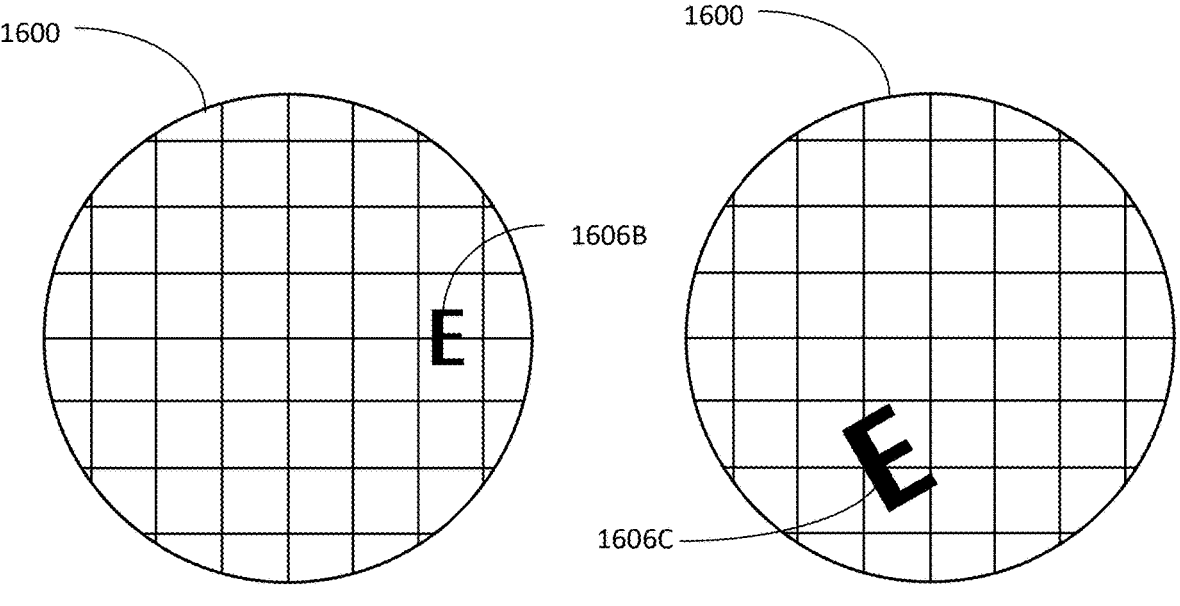
FIG. 16E                     FIG. 16F

SYSTEMS AND METHODS FOR EVALUATING EYE MOVEMENT DISORDERS THROUGH EYE-TRACKING EXERCISES

BACKGROUND

Field of the Inventions

The present application relates to methods of assessing various ocular conditions through extended reality systems. More specifically, methods and systems are applied to conduct visual tasks and exams in extended reality environments to evaluate patients for ocular conditions and diseases, such as eye misalignment and visual processing disorders.

Description of the Related Art

As virtual reality (VR) technology has become increasingly sophisticated, new highly immersive experiences have been made possible through improvements in head and motion tracking systems. Eye-tracking technology allows systems to detect and respond to where the user is looking. This capability enhances user interaction and makes virtual environments more responsive and engaging. Eye tracking is being integrated into a variety of VR applications, from gaming and training simulations to medical diagnostics and research, as it offers a more intuitive way for users to interact with digital content.

SUMMARY

The systems, methods and devices of this disclosure each have several innovative aspects, no single one of which is solely responsible for the desirable attributes disclosed herein.

Despite the advancements in VR technology, and in particular, eye-tracking technology, in accordance with some embodiments disclosed herein is the realization that VR technology can provide unique eyecare solutions through monitoring and tracking one or more of the user's eyes and providing a diagnostic, treatment protocol, and/or treatment system. Indeed, in accordance with some embodiments disclosed herein is the realization that VR technology can be used to address challenges associated with diagnosing a variety of eye disorders and ocular conditions, such as detecting misalignment, macular degeneration, tear film characteristics, floater characteristics, eye tracking issues, motion sensitivity, and other eye movement disorders and the treatment of such.

In some embodiments, a virtual reality (VR) guided examination can be conducted for diagnosing and measuring eye movement disorders through a series of interactive eye-tracking exercises. This method can be implemented through a system that comprises a high-resolution VR headset integrated with precision eye-tracking technology and specialized software capable of generating a variety of visual stimuli and tasks. Patients wear the VR headset and engage in a series of exercises specifically designed to assess different aspects of eye movement, such as saccades, smooth pursuits, and fixation stability. The eye-tracking sensors continuously monitor the patient's eye movements, providing real-time data on the accuracy, speed, and coordination of their ocular motor functions.

Optionally, a VR software can employ a range of diagnostic tasks, such as following moving objects, rapidly shifting gaze between fixed points, and maintaining steady focus on a single target. These tasks are tailored to detect and measure anomalies in eye movements that are indicative of disorders like nystagmus, strabismus, and oculomotor nerve palsies. The software processes the eye-tracking data using advanced algorithms to identify patterns and deviations from normal ocular motor behavior. The results are compiled into a detailed report that highlights specific eye movement abnormalities, providing valuable insights for clinicians to diagnose and monitor the progression of eye movement disorders.

To construct the VR-based eye movement disorder diagnostic system, begin with a high-quality VR headset, such as the Oculus Quest 2, integrated with high-precision eye-tracking technology. The eye-tracking sensors should include infrared cameras capable of capturing detailed and rapid eye movements with high accuracy. The software development involves creating a library of eye-tracking exercises designed to evaluate various aspects of eye movement. These exercises include tasks such as tracking moving targets, performing quick gaze shifts, and maintaining prolonged focus on static objects.

Once the hardware and software components are integrated, the system undergoes calibration using a control group of individuals with known eye movement profiles to establish baseline performance metrics and validate the accuracy of the diagnostic algorithms. Users can then operate the system by wearing the VR headset and participating in the guided eye-tracking exercises within the virtual environments. The eye-tracking sensors monitor their eye movements and responses to the visual stimuli, while the software records and analyzes the data in real-time. The user receives a detailed report outlining their eye movement performance, highlighting any deviations from normal patterns, and providing recommendations for further medical consultation if necessary. This approach offers a precise, non-invasive, and user-friendly method for diagnosing and measuring eye movement disorders, providing substantial benefits for both clinical and research applications.

In some embodiments, a VR method for testing visual reaction time can be performed by using fast-moving objects in a virtual space. This system comprises a high-resolution VR headset equipped with precision eye-tracking sensors and specialized software capable of generating a dynamic virtual environment. Users wear the VR headset and engage in a series of tasks that involve detecting, tracking, and responding to fast-moving objects within the virtual space. The eye-tracking sensors monitor the user's eye movements and reaction times, providing real-time data on their visual processing speed and responsiveness.

In some embodiments, the VR headset can be equipped with a variety of visual tasks designed to challenge the user's reaction time, such as following rapidly moving targets, identifying objects that appear and disappear quickly, and making split-second decisions based on visual cues. The software processes the data collected by the eye-tracking sensors using advanced algorithms to measure the user's reaction time with high precision. The results are compiled into a comprehensive report that provides insights into the user's visual processing speed, highlighting any deficiencies that could indicate underlying neurological or visual impairments. This method offers a dynamic, engaging, and accurate approach to evaluating visual reaction time in a controlled virtual environment.

To construct the VR-based visual reaction time testing system, begin with a high-quality VR headset, such as the Oculus Quest 2, integrated with high-precision eye-tracking technology. The eye-tracking sensors should include infrared cameras capable of capturing detailed eye movements and reaction times with high accuracy. The software development involves creating a library of fast-moving visual stimuli and tasks designed to test different aspects of visual reaction time. These tasks include scenarios where users must quickly identify, track, and respond to objects moving at various speeds and trajectories within the virtual environment.

Once assembled, the VR system undergoes rigorous calibration and testing using a control group of individuals with known visual reaction time profiles to establish baseline performance metrics and validate the accuracy of the reaction time measurements. Users can then operate the system by wearing the VR headset and participating in the guided visual tasks within the virtual environments. The eye-tracking sensors monitor their eye movements and responses to the fast-moving objects, while the software records and analyzes the data in real-time. The user receives a detailed report outlining their visual reaction time performance, highlighting any deviations from normal patterns, and providing recommendations for further medical consultation if necessary. This approach offers a precise, non-invasive, and user-friendly method for assessing visual reaction time, representing a significant advancement over traditional testing techniques and providing substantial benefits for both clinical and research applications.

Optionally, a VR method designed to assess eye coordination can be performed by requiring users to track and interact with moving objects within a virtual environment. This system comprises a high-resolution VR headset equipped with precision eye-tracking sensors and specialized software capable of creating dynamic, interactive visual stimuli. Users wear the VR headset and engage in a series of tasks that involve following and interacting with various moving objects. These tasks are designed to evaluate the user's eye coordination, including saccadic movements, smooth pursuits, and convergence and divergence abilities. The eye-tracking sensors monitor the user's eye movements and responses in real-time, while the software analyzes these responses to provide a detailed assessment of eye coordination.

In some embodiments, the VR system can be equipped with a variety of interactive tasks, such as tracking multiple moving targets, catching or hitting virtual objects, and following complex motion paths. These tasks are designed to challenge the user's ability to coordinate both eyes effectively to track and interact with dynamic objects. The software processes the eye-tracking data using advanced algorithms to measure parameters such as reaction time, accuracy of eye movements, and the synchronization between the eyes. The results are compiled into a comprehensive report that highlights the user's eye coordination performance, identifying any deficiencies that could indicate conditions such as strabismus, amblyopia, or other binocular vision disorders.

To create the VR-based eye coordination assessment system, begin with a high-quality VR headset, such as the Oculus Quest 2, integrated with high-precision eye-tracking technology. The eye-tracking sensors should include infrared cameras capable of capturing detailed eye movements with high accuracy and minimal latency. The software development involves creating a library of interactive visual tasks that simulate moving objects in various patterns and speeds. These tasks include scenarios where users must follow moving targets, interact with virtual objects by catching or hitting them, and track objects moving along complex paths, all designed to challenge and assess different aspects of eye coordination.

Once the hardware and software components are integrated, the system undergoes calibration using a control group of individuals with known eye coordination profiles to establish baseline performance metrics and validate the accuracy of the assessment algorithms. Users can then operate the system by wearing the VR headset and participating in the guided interactive tasks within the virtual environments. The eye-tracking sensors monitor their eye movements and responses to the moving objects, while the software records and analyzes the data in real-time. The user receives a detailed report outlining their eye coordination performance, highlighting any deviations from normal patterns, and providing recommendations for further medical consultation if necessary. This approach offers a precise, non-invasive, and user-friendly method for assessing eye coordination, representing a significant advancement over traditional testing techniques and providing substantial benefits for both clinical and consumer applications.

In some embodiments, a VR method designed to test for sensitivity to motion can be executed using fast-paced, interactive VR scenes. This VR method is carried out using a VR system, which comprises a high-resolution VR headset equipped with precision eye-tracking sensors and specialized software capable of generating dynamic, interactive environments that simulate rapid motion. Users wear the VR headset and engage in a series of tasks that involve detecting, tracking, and responding to fast-moving objects and scenes. The eye-tracking sensors monitor the user's eye movements, tracking accuracy, and reaction times, while the software analyzes these responses to assess the user's sensitivity to motion, including motion perception, motion sickness susceptibility, and visual processing speed.

Optionally, the VR system can be equipped with a variety of interactive scenes, such as navigating through busy virtual environments, following rapidly moving objects, and reacting to sudden changes in the visual field. These tasks are designed to challenge the user's visual system by presenting stimuli that require quick and precise visual processing. The software processes the data in real-time, using advanced algorithms to evaluate the user's ability to perceive and respond to motion accurately. The results are compiled into a comprehensive report that highlights the user's sensitivity to motion, identifying any abnormalities or susceptibilities that could indicate underlying visual or neurological conditions, such as vestibular disorders, motion sickness, or impaired motion perception.

To construct the VR-based motion sensitivity testing system, begin with a high-quality VR headset, such as the Oculus Quest 2, integrated with high-precision eye-tracking technology. The eye-tracking sensors should include infrared cameras capable of capturing detailed eye movements and reaction times with high accuracy. The software development involves creating a library of fast-paced, interactive VR scenes designed to test different aspects of motion sensitivity. These scenes include scenarios where users must navigate through complex environments, follow rapidly moving targets, and react to sudden changes in motion, all designed to challenge and measure the user's sensitivity to motion.

Once assembled, the VR system undergoes rigorous calibration and testing using a control group of individuals with known motion sensitivity profiles to establish baseline performance metrics and validate the accuracy of the assessment algorithms. Users can then operate the system by wearing the VR headset and participating in the guided interactive tasks within the virtual environments. The eye-tracking sensors monitor their eye movements and responses to the fast-paced scenes, while the software records and analyzes the data in real-time. The user receives a detailed report outlining their motion sensitivity performance, highlighting any deviations from normal patterns, and providing recommendations for further medical consultation if necessary. This approach offers a precise, non-invasive, and user-friendly method for assessing motion sensitivity, representing a significant advancement over traditional testing techniques and providing substantial benefits for both clinical and consumer applications.

Optionally, a VR method designed to evaluate spatial awareness can be performed by combining motion tracking with vision testing. This VR system comprises a high-resolution VR headset integrated with both precision eye-tracking and motion-tracking technologies, along with specialized software capable of generating interactive, three-dimensional environments. Users wear the VR headset and engage in a series of tasks that require them to move within a virtual space while simultaneously responding to visual stimuli. The system's motion-tracking sensors capture the user's physical movements and spatial orientation, while the eye-tracking sensors monitor their gaze direction and visual responses. This dual-tracking approach provides a comprehensive assessment of the user's spatial awareness, visual perception, and coordination.

In some embodiments, the VR system can be equipped with a variety of interactive tasks, such as navigating through virtual mazes, avoiding obstacles, and identifying objects from different perspectives. These tasks are designed to challenge the user's ability to integrate visual information with physical movement, thereby testing their spatial awareness and navigation skills. The software processes the data in real-time, using advanced algorithms to evaluate the user's performance in terms of accuracy, reaction time, and spatial orientation. The results are compiled into a detailed report that highlights the user's spatial awareness capabilities, identifying any deficiencies that could indicate conditions such as spatial neglect, balance disorders, or impaired depth perception. This VR method offers a dynamic, engaging, and precise approach to evaluating spatial awareness in a controlled virtual environment.

To create the VR spatial awareness assessment system, begin with a high-quality VR headset, such as the Oculus Quest 2, integrated with both high-precision eye-tracking and motion-tracking technologies. The eye-tracking sensors should include infrared cameras capable of capturing detailed eye movements, while the motion-tracking sensors should include accelerometers and gyroscopes to accurately capture the user's physical movements and orientation. The software development involves creating a library of interactive 3D environments and tasks designed to test different aspects of spatial awareness. These tasks include scenarios where users must navigate through complex mazes, avoid virtual obstacles, and identify objects from various angles, all designed to challenge and measure the user's spatial awareness and coordination.

Once the hardware and software components of the VR system are integrated, the VR system undergoes calibration using a control group of individuals with known spatial awareness profiles to establish baseline performance metrics and validate the accuracy of the assessment algorithms. Users can then operate the system by wearing the VR headset and participating in the guided interactive tasks within the virtual environments. The motion-tracking sensors capture their physical movements and spatial orientation, while the eye-tracking sensors monitor their gaze direction and visual responses. The software records and analyzes the data in real-time, and the user receives a detailed report outlining their spatial awareness performance, highlighting any deviations from normal patterns, and providing recommendations for further medical consultation if necessary. This approach offers a precise, non-invasive, and user-friendly method for assessing spatial awareness, representing a significant advancement over traditional testing techniques and providing substantial benefits for both clinical and consumer applications.

In some embodiments, VR method for assessing the stability and effectiveness of eye tracking can be carried out using gaze-contingent displays. This VR system consists of a high-resolution VR headset equipped with precision eye-tracking sensors and specialized software capable of generating interactive visual stimuli that dynamically respond to the user's gaze. Users wear the VR headset and engage in a series of tasks that involve maintaining focus on moving targets, following dynamic patterns, and responding to visual cues that change based on their gaze direction. The eye-tracking sensors continuously monitor the user's eye movements, while the gaze-contingent displays adjust in real-time to ensure the visual stimuli remain in sync with the user's gaze.

Optionally, the VR system can be equipped with a range of tasks such as tracking a moving dot that changes speed and direction, keeping focus on a central point while peripheral objects change, and interacting with objects that react to the user's gaze. These tasks are designed to challenge the user's ability to maintain stable and accurate eye tracking. The software processes the data in real-time, using advanced algorithms to evaluate parameters such as fixation stability, saccadic latency, and tracking accuracy. The results are compiled into a comprehensive report that highlights the user's eye tracking performance, identifying any deficiencies that could indicate conditions such as nystagmus, oculomotor dysfunction, or other eye movement disorders. This method offers a dynamic, precise, and interactive approach to evaluating the stability and effectiveness of eye tracking in a controlled virtual environment.

To create the VR tear film examination system, begin with a high-quality VR headset, such as the Oculus Quest 2, integrated with high-precision eye-tracking technology. The eye-tracking sensors should include infrared cameras capable of capturing detailed eye movements with high accuracy and minimal latency. The software development involves creating a library of gaze-contingent visual tasks designed to test different aspects of eye tracking stability and effectiveness. These tasks include scenarios where visual stimuli move in response to the user's gaze, requiring them to maintain focus and track objects accurately.

Once assembled, the VR system undergoes rigorous calibration and testing using a control group of individuals with known eye tracking profiles to establish baseline performance metrics and validate the accuracy of the assessment algorithms. Users can then operate the system by wearing the VR headset and participating in the guided gaze-contingent tasks within the virtual environments. The eye-tracking sensors monitor the users' eye movements and responses to the dynamic visual stimuli, while the software records and analyzes the data in real-time. The users receive detailed reports outlining their eye tracking performance, highlighting any deviations from normal patterns, and providing recommendations for further medical consultation if necessary. This approach offers a precise, non-invasive, and user-friendly method for assessing the stability and effectiveness of eye tracking, representing a significant advancement over traditional testing techniques and providing substantial benefits for both clinical and research applications.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures:

FIGS. 9A-9C include three diagrams of example graphical user interfaces rendered to determine a nearsighted or farsighted power in a virtual environment created by a headset device, in accordance with some embodiments.

FIGS. 16A-16C illustrate a shape with variations of a grid pattern which can be used to assess and improve the patient's eye-tracking stability and effectiveness, in accordance with some embodiments.

FIGS. 16D-16F illustrate a shape with an optotype displayed in various orientations, positions, and sizes relative to a grid pattern, in accordance with some embodiments.

DETAILED DESCRIPTION

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

Figure 1:
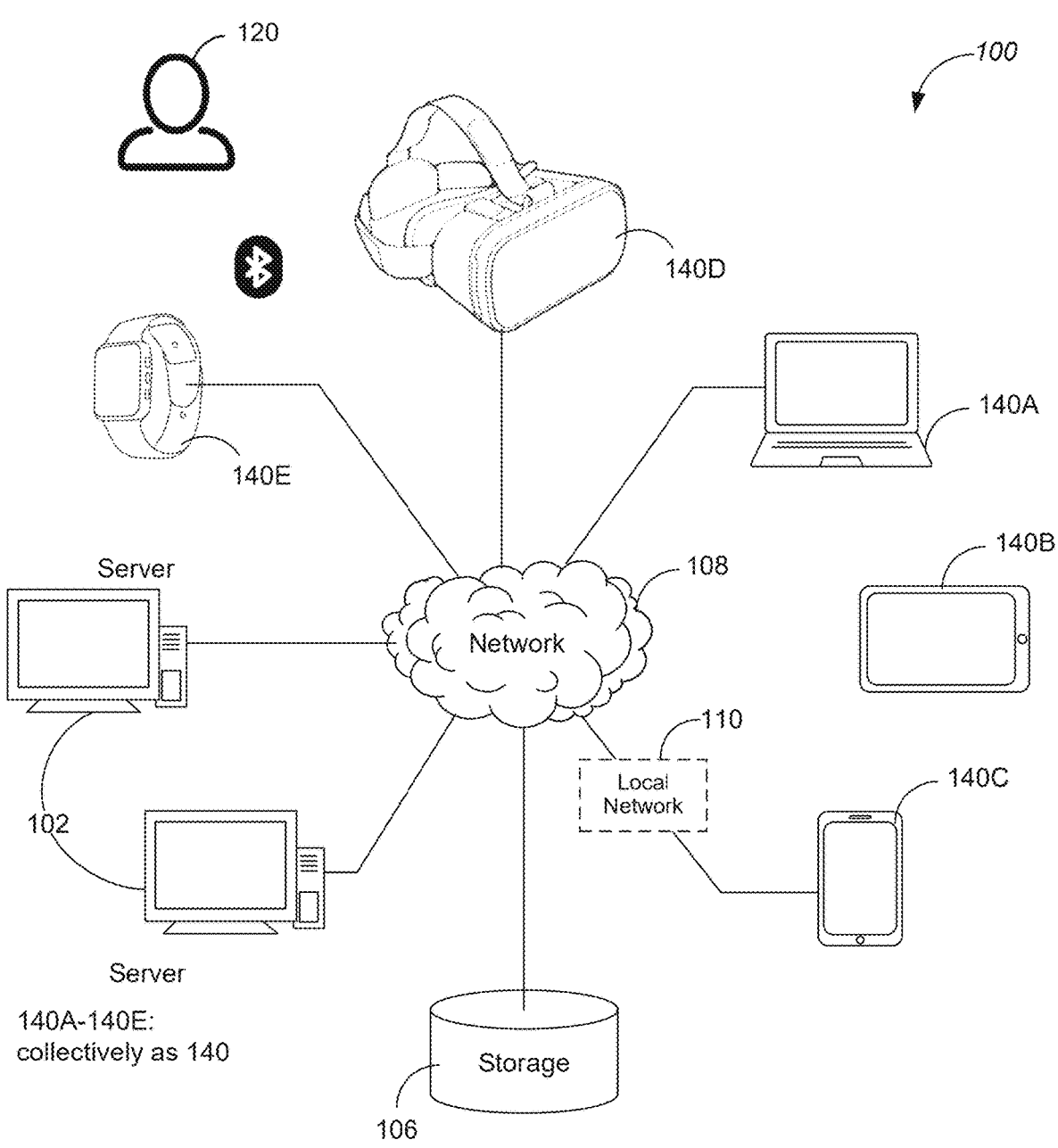
FIG. 1 is an example data processing environment having one or more servers communicatively coupled to one or more computer devices, in accordance with some embodiments.

Referring now to the figures, FIG. 1 is an example data processing environment 100 having one or more servers 102 communicatively coupled to one or more computer devices 140 (e.g., a headset device 140D), in accordance with some embodiments. The one or more computer devices 140 are electronic devices having computational capabilities, and may be, for example, desktop computers 140A, tablet computers 140B, mobile phones 140C, or intelligent, multi-sensing, network-connected home devices (e.g., a depth camera, a visible light camera).

In some implementations, the one or more computer devices 140 can include a headset device 140D (also called a head-mounted display (HMD) device 140D) configured to render extended reality content. In some implementations, the one or more computer devices 140 can include a wireless wearable device 140E (e.g., a smart watch, a fitness band) configured to track health data (e.g., heart rate, quality of sleep) and activity data (e.g., steps walked, stairs climbed) of a user wearing the device 140E. Each computer device 140 can collect data or user inputs, executes user applications, and present outputs on its user interface. The collected data or user inputs can be processed locally at the computer device 140 and/or remotely by the server(s) 102. The one or more servers 102 can provide system data (e.g., boot files, operating system images, and user applications) to the computer devices 140, and in some embodiments, processes the data and user inputs received from the computer device (s) 140 when the user applications are executed on the computer devices 140. In some embodiments, the data processing environment 100 can further include a storage 106 for storing data related to the servers 102, computer devices 140, and applications executed on the computer devices 140. For example, storage 106 may store video content, static visual content, and/or audio data.

The one or more servers 102 can enable real-time data communication with the computer devices 140 that can be remote from each other or from the one or more servers 102. Further, in some embodiments, the one or more servers 102 can implement data processing tasks that are not completed locally by the computer devices 140. For example, the computer devices 140 can include a game console (e.g., the headset device 140D) that executes an interactive online gaming application (e.g., for visual assessment or eyewear fitting). The game console receives a user instruction and sends it to a server 102 with user data. The server 102 generates a stream of video data based on the user instruction and user data and provides the stream of video data for display on the game console and other computer devices that can be engaged in the same session with the game console.

The one or more servers 102, one or more computer devices 140, and storage 106 can be communicatively coupled to each other via one or more communication networks 108, which are the medium used to provide communications links between these devices and computers connected together within the data processing environment 100. The one or more communication networks 108 may include connections, such as wire, wireless communication links, or fiber optic cables. Examples of the one or more communication networks 108 include local area networks (LAN), wide area networks (WAN) such as the Internet, or a combination thereof. The one or more communication networks 108 are, optionally, implemented using any known network protocol includes various wired or wireless protocols, such as Ethernet, Universal Serial Bus (USB), FIRE-WIRE, Long Term Evolution (LTE), Global System for Mobile Communications (GSM), Enhanced Data GSM Environment (EDGE), code division multiple access (CDMA), time division multiple access (TDMA), Bluetooth, Wi-Fi, voice over Internet Protocol (VOIP), Wi-MAX, or any other suitable communication protocol. A connection to the one or more communication networks 108 may be established either directly (e.g., using 1G/4G connectivity to a wireless carrier), or through a network interface 110 (e.g., using a router, switch, gateway, hub, or an intelligent, dedicated whole-home control node), or through any combination thereof. As such, the one or more communication networks 108 can represent the Internet of a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other electronic systems that route data and messages.

In some embodiments, the headset device 140D can be communicatively coupled to a data processing environment 100. The headset device 140D includes one or more cameras (e.g., a visible light camera, a depth camera), a microphone, a speaker, one or more inertial sensors (e.g., gyroscope, accelerometer), and a display. In some embodiments, the camera may capture hand gestures of a user wearing the headset device 140D. In some embodiments, the microphone records ambient sound includes user's voice commands.

In some embodiments, the headset device 140D may be communicatively coupled to one or more servers 102 and enables a centralized vision test management platform with the one or more servers 102. This vision test management platform may aggregate data (e.g., visual stimuli 338, sensor data 342, vision test results 344) from a plurality of user accounts associated with a plurality of users, analyze the aggregated data, and track vision health trends for individual users or user groups. In some embodiments, data may be communicated between a headset device 140D and a server 102 in an encrypted format. In some embodiments, the vision test management platform is coupled to a global health database storing epidemiological data. The vision test management platform can be configured to cross-reference the data collected from its user accounts with the epidemiological data to identify an emerging pattern and a public health concern. For example, a teenager's vision data may be collected and analyzed during an extended duration of time (e.g., 10 years) to identify an individual vision development trend and was cross-referenced with an average vision development trend extracted from the global health database. A doctor can rely on a cross-referencing result to determine whether the individual vision development trend is normal or whether the teenager's eyesight drops faster than average teenagers. As such, various embodiments of the vision test management platform may integrate biometric data and global health analytics and provides a secure, personalized, and interactive environment for vision testing, which can improve precision and user experience of vision assessments and contributes to broader public health monitoring and research initiatives.

Figure 2:
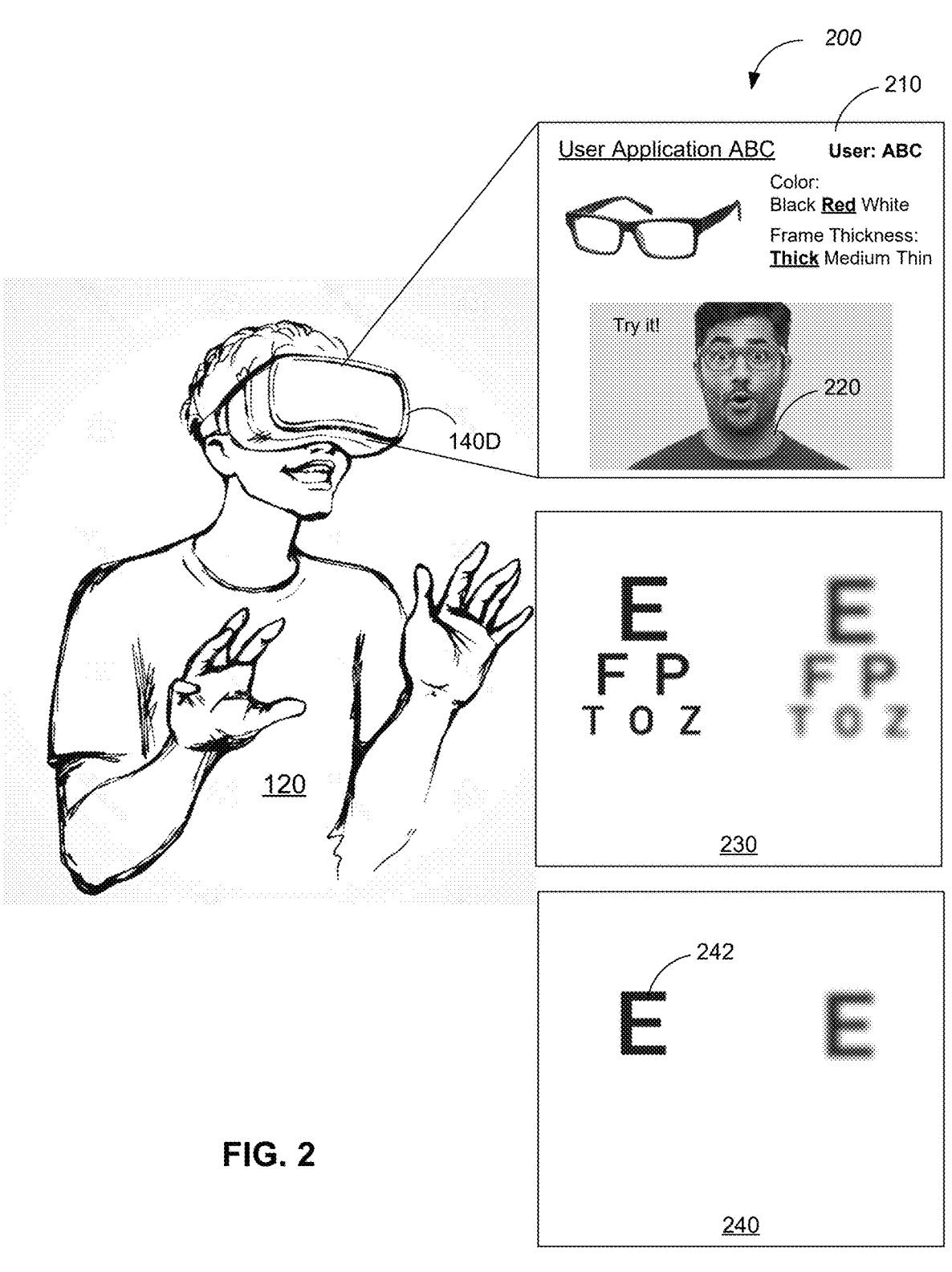
FIG. 2 is an environment in which a computer device is applied to facilitate visual assessment or eyewear fitting, in accordance with some embodiments.

FIG. 2 is an environment 200 in which a computer device 140 (e.g., a headset device 140D) is applied to facilitate visual assessment or eyewear fitting, in accordance with some embodiments. The XR headset device 140D may be communicatively coupled within the data processing environment 100. The XR headset device 140D may include one or more cameras (e.g., a visible light camera, a depth camera), a microphone, a speaker, one or more inertial sensors (e.g., gyroscope, accelerometer), and a display. In some embodiments, the camera may capture hand gestures of a user wearing the XR headset device 140D. In some embodiments, the microphone may record ambient sound includes user's voice commands. The XR headset device 140D may execute a client-side eyewear fitting application 326 or a client-side visual assessment application 328 (FIG. 3) via a user account associated with a user 120 (e.g., an optometrist user, an optician user, a patient user). In some implementations, a computer device 140 (e.g., a mobile phone 140C) distinct from the XR headset device 140D can be used to implement the client-side eyewear fitting application 326 or visual assessment application 328 (FIG. 3).

In some embodiments, a first user interface 210 can be displayed on a computer device 140 (e.g., the headset device 140D) associated with the user 120. In some embodiments, an eyewear can be tried on or displayed as being worn by a 2D or 3D image 220 of the user 120. The server 102 or computer device 140 may receive, from the first user interface 210, a user feedback message indicating an issue, requesting further improvement, or confirming a fit. In some embodiments, a second user interface 230 can be displayed on a computer device 140 associated with the user 120. The second user interface 230 may include a plurality of optotypes (e.g., six optotypes E, F, P, T, O, and Z) having different sizes. In some embodiments, a third user interface 240 can be displayed on a computer device 140 associated with the user 120. The second user interface 230 can display a temporal sequence of optotypes having respective sizes. Each optotype of a corresponding size can be displayed at one time.

Figure 3:
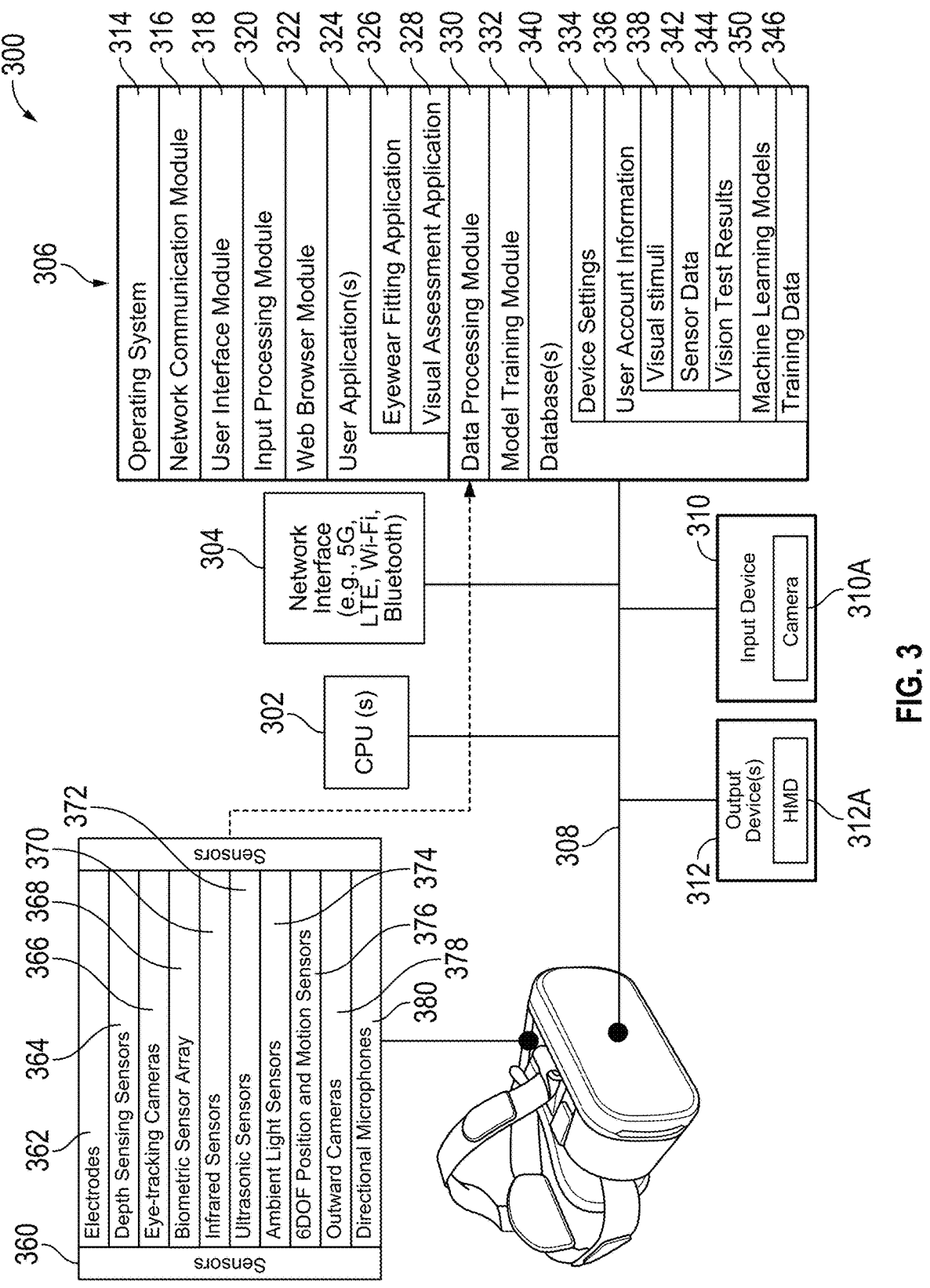
FIG. 3 is a block diagram of a computer system configured to implement vision assessment or eyewear fitting, in accordance with some embodiments.

FIG. 3 is a block diagram of a computer system 300 (e.g., including a headset device 140D, a server, or a combination thereof) configured to implement vision assessment or eyewear fitting, in accordance with some embodiments. The computer system 300 can include one or more processing units (CPUs) 302, one or more network interfaces 304, memory 306, and one or more communication buses 308 for interconnecting these components (sometimes called a chipset). The computer system 300 may include one or more input devices 310 that facilitate user input, such as a keyboard, a mouse, a voice-command input unit or microphone, a touch screen display, a touch-sensitive input pad, a gesture capturing camera, or other input buttons or controls. Furthermore, in some embodiments, the computer device 140 of the computer system 300 may use a microphone for voice recognition or an eye tracking camera 366 for tracking eyeball movement. In some implementations, the computer device 140 may include one or more optical cameras (e.g., an RGB camera), scanners, or photo sensor units for capturing images. The computer system 300 may also include one or more output devices 312 that enable presentation of user interfaces 210 and media content. The one or more output devices 312 may include one or more speakers and/or one or more visual displays.

The computer system 300 may include one or more sensors 360, which further may include one or more of: a plurality of electrodes 362, one or more depth sensing sensors 364, one or more eye tracking cameras 366, a biometric sensor array 368, one or more infrared sensors 370, one or more ultrasonic sensors 372, one or more ambient sensors 374, one or more motion sensors (e.g., six degree of freedom (6DOF) position and motion sensors 376), one or more outward camera 378, and one or more directional microphones 380. It is noted that the one or more sensors 360 can also be included in the input device 310 and used to collect data to the computer system 300.

Memory 306 may include high-speed random-access memory, such as DRAM, SRAM, DDR RAM, or other random-access solid state memory devices; and, optionally, may include non-volatile memory, such as one or more magnetic disk storage devices, one or more optical disk storage devices, one or more flash memory devices, or one or more other non-volatile solid state storage devices. Memory 306, optionally, may include one or more storage devices remotely located from one or more processing units 302. Memory 306, or alternatively the non-volatile memory within memory 306, may include a non-transitory computer readable storage medium. In some implementations, memory 306, or the non-transitory computer readable storage medium of memory 306, may store the following programs, modules, and data structures, or a subset or superset thereof:

Operating system 314 including procedures for handling various basic system services and for performing hardware dependent tasks;

Network communication module 316 for connecting each server 102 or computer device 140 to other devices (e.g., server 102, computer device 140, or storage 106) via one or more network interfaces 304 (wired or wireless) and one or more communication networks 108, such as the Internet, other wide area networks, local area networks, metropolitan area networks, and so on;

User interface module 318 for enabling presentation of information (e.g., a graphical user interface for application(s) 324, widgets, websites and web pages thereof, and/or games, audio and/or video content, text, etc.) at each computer device 140 via one or more output devices 312 (e.g., displays, speakers, etc.);

Input processing module 320 for detecting one or more user inputs or interactions from one of the one or more input devices 310 and interpreting the detected input or interaction;

Web browser module 322 for navigating, requesting (e.g., via HTTP), and displaying websites and web pages thereof may include a web interface for logging into a user account associated with a computer device 140 or another electronic device, controlling the computer device if associated with the user account, and editing and reviewing settings and data that are associated with the user account;

One or more user applications 324 for execution by the computer system 300 (e.g., games, social network applications, smart home applications, extended reality application, and/or other web or non-web-based applications for controlling another electronic device and reviewing data captured by such devices), where in some embodiments, an eyewear fitting application 326 can be executed to implement eyewear fitting, and has a plurality of user accounts associated with a plurality of users 120 (e.g., technician users and eyewear users), and in some embodiments, a visual assessment application 328 can be executed to evaluate eyesight of a patient user, and has a plurality of user accounts associated with a plurality of users 120 (e.g., an optometrist user, a patient user);

Data processing module 330 for processing data associated with the user applications 324, e.g., using machine learning models 350;

Model training Module 332 for obtaining training data 346 and training machine learning models 350; and One or more databases 340 for storing at least data including one or more of:

Device settings 334 including common device settings (e.g., service tier, device model, storage capacity, processing capabilities, communication capabilities, etc.) of the computer system 300;

User account information 336 for the one or more user applications 324, e.g., user names, security questions, account history data, user preferences, and predefined account settings, where in some embodiments, the user account information 336 may include facial measurements and one or more virtual fitting parameters associated with associated with a user account of an eye fitting application 326, and in some embodiments, the user account information 336 may include visual stimuli 338, sensor data 342, and vision test results 344 associated with a user account of a visual assessment application 328; and Machine learning models 350 including parameters (e.g., weights, biases) used to implement vision test or select eyewear for eyewear users.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, modules or data structures, and thus various subsets of these modules may be combined or otherwise re-arranged in some embodiments. In some embodiments, memory 306, optionally, stores a subset of the modules and data structures identified above. Furthermore, memory 306, optionally, stores additional modules and data structures not described above.

Figure 4:
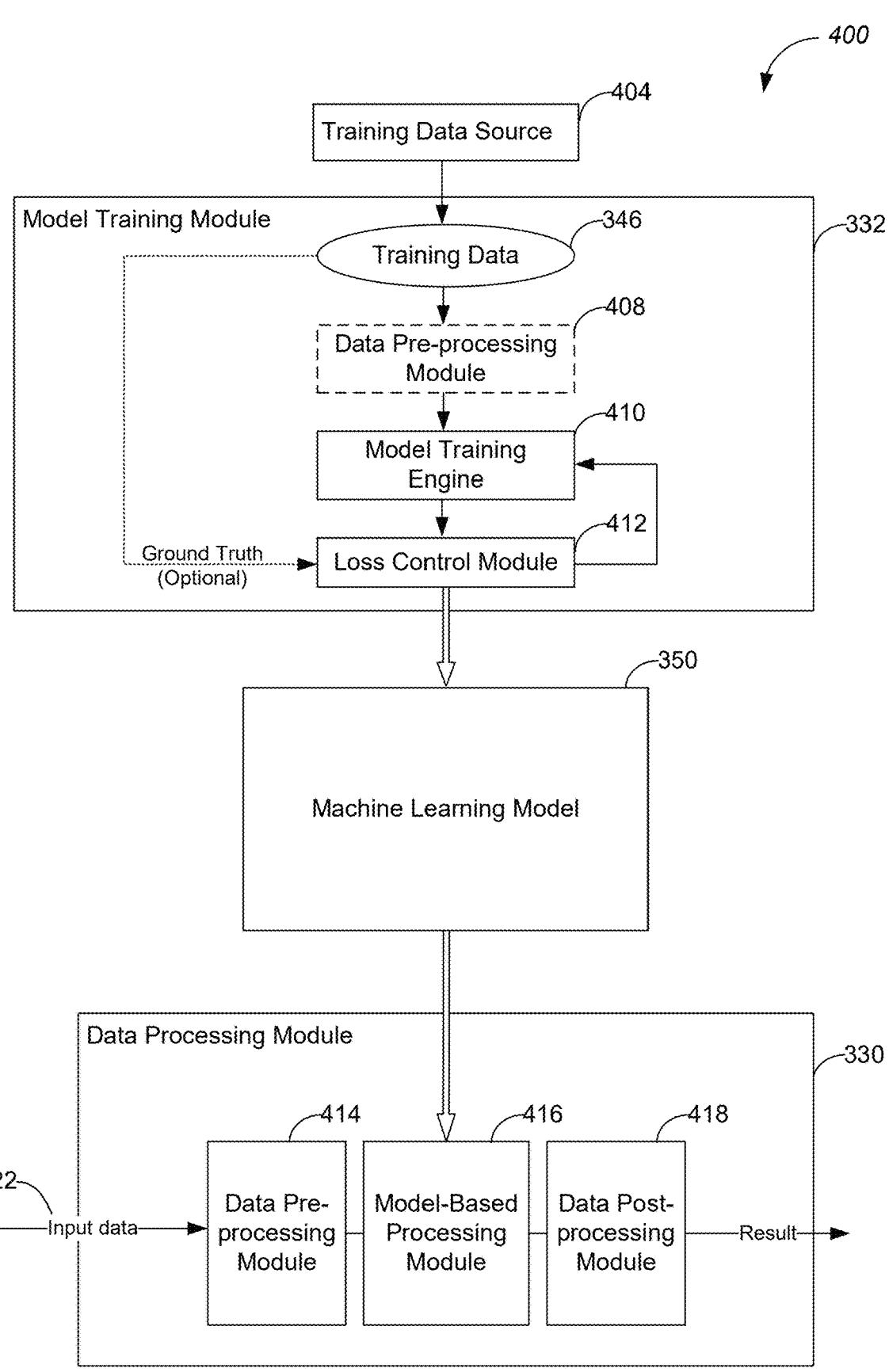
FIG. 4 is a block diagram of a machine learning system for training and applying machine learning models, in accordance with some embodiments.

FIG. 4 is a block diagram of a machine learning system 400 for training and applying machine learning models 350 (e.g., for glass making), in accordance with some embodiments. The machine learning system 400 may include a model training module 332 establishing one or more machine learning models 350 and a data processing module 330 for processing input data 422 using the machine learning model 350. In some embodiments, both the model training module 332 and the data processing module 330 may be located within a computer device 140 (e.g., a VR headset), while a training data source 404 provides training data 346 to the computer device 140. In some embodiments, the training data source 404 may include the data obtained from the computer device 140 itself, from a server 102, from storage 106, or from another electronic device or computer device 140. Alternatively, in some embodiments, the model training module 332 may be located at a server 102, and the data processing module 330 may be located in a computer device 140. The server 102 can train the machine learning model 350 and provide the trained models 350 to the computer device 140 to process real-time input data 422 detected by the computer device 140. In some embodiments, the training data 346 provided by the training data source 404 may include a standard dataset widely used to train machine learning models 350. The input data 422 further may include sensor data. Further, in some embodiments, a subset of the training data 346 may be modified to augment the training data 346. The subset of modified training data may be used in place of or jointly with the subset of training data 346 to train the machine learning models 350.

In some embodiments, the model training module 332 may include a model training engine 410, and a loss control module 412. Each machine learning model 350 may be trained by the model training engine 410 to process corresponding input data 422 and implement a respective task. Specifically, the model training engine 410 may receive the training data 346 corresponding to a machine learning model 350 to be trained and process the training data to build the machine learning model 350. In some embodiments, during this process, the loss control module 412 can monitor a loss function comparing the output associated with the respective training data item to a ground truth of the respective training data item. In these embodiments, the model training engine 410 may modify the machine learning models 350 to reduce the loss, until the loss function satisfies a loss criterion (e.g., a comparison result of the loss function is minimized or reduced below a loss threshold). The machine learning models 350 may thereby be trained and provided to the data processing module 330 of a computer device 140 to process real-time input data 422 from the computer device 140.

In some embodiments, the model training module 402 may further include a data pre-processing module 408 configured to pre-process the training data 346 before the training data 346 is used by the model training engine 410 to train a machine learning model 350. For example, an image pre-processing module 408 is configured to format patients' eye images in the training data 346 into a predefined image format. For example, the preprocessing module 408 may normalize the images to a fixed size, resolution, or contrast level. In another example, an image pre-processing module 408 extracts a region of interest (ROI) corresponding to an eye area.

In some embodiments, the model training module 332 can use supervised learning in which the training data 346 may be labelled and include a desired output for each training data item (also called the ground truth, in some embodiments). In some embodiments, the desirable output may be labelled manually by people or automatically by the model training model 332 before training. In some embodiments, the model training module 332 may use unsupervised learning in which the training data 346 is not labelled. The model training module 332 is configured to identify previously undetected patterns in the training data 346 without pre-existing labels and with little or no human supervision. Additionally, in some embodiments, the model training module 332 may use partially supervised learning in which the training data is partially labelled.

In some embodiments, the data processing module 330 may include a data pre-processing module 414, a model-based processing module 416, and a data post-processing module 418. The data pre-processing modules 414 may pre-process input data 422 based on the type of the input data 422. In some embodiments, functions of the data pre-processing modules 414 are consistent with those of the pre-processing module 408. The data pre-processing modules 414 can convert the input data 422 into a predefined data format that is suitable for the inputs of the model-based processing module 416. The model-based processing module 416 may apply the trained machine learning model 350 provided by the model training module 332 to process the pre-processed input data 422. In some embodiments, the model-based processing module 416 can also monitor an error indicator to determine whether the input data 422 has been properly processed in the machine learning model 350. In some embodiments, the processed input data may be further processed by the data post-processing module 418 to create a preferred format or to provide additional information that can be derived from the processed input data. The data processing module 330 may use the processed input data to make eyewear glasses for a patient user.

Figures 5A, 5B:
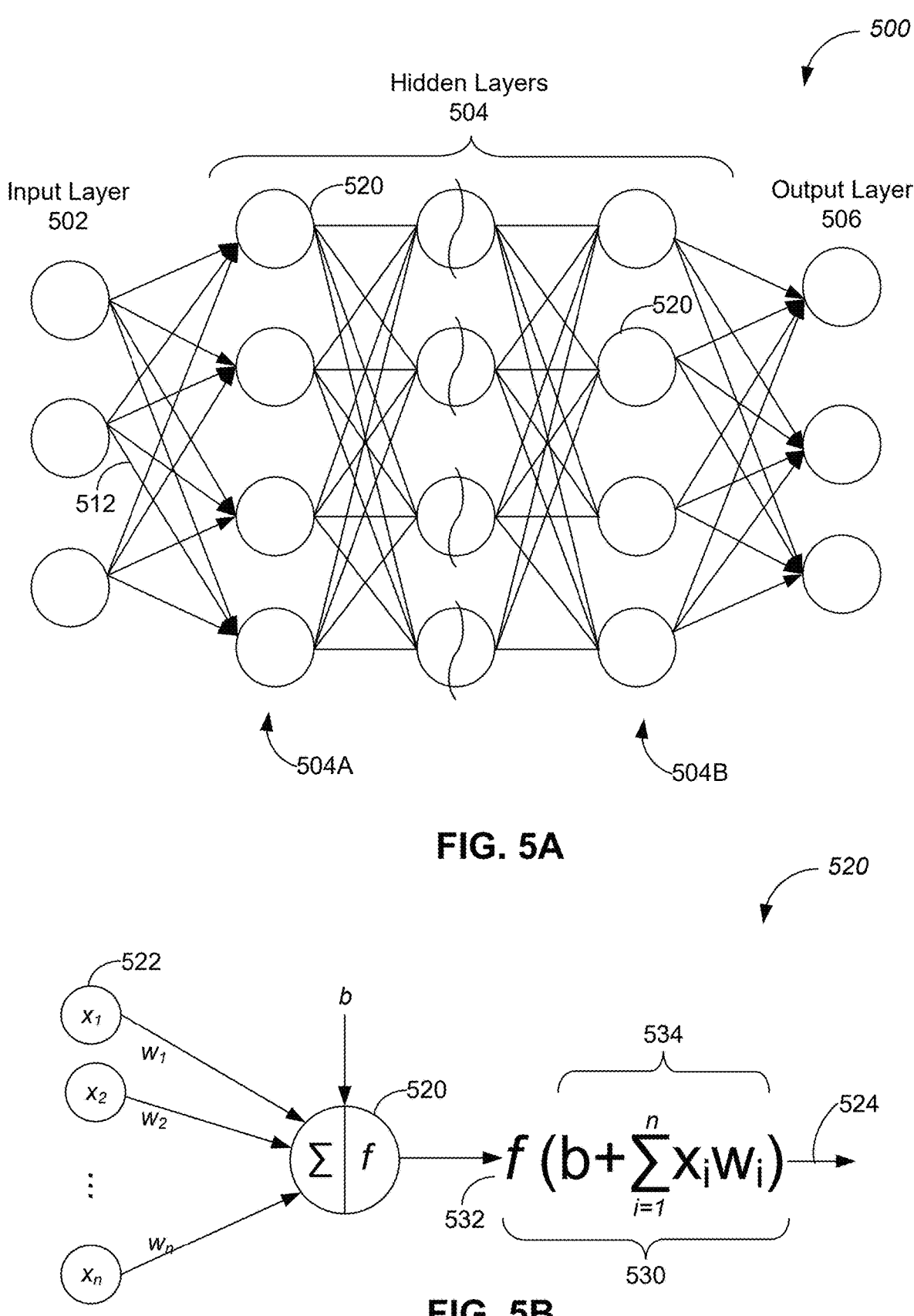
FIG. 5A is a structural diagram of an example neural network applied to process input data in a machine learning model, in accordance with some embodiments.
FIG. 5B is an example node in the neural network, in accordance with some embodiments.

FIG. 5A is a structural diagram of an example neural network 500 applied to process input data in a machine learning model 350, in accordance with some embodiments.

Further, FIG. 5B is an example node 520 in the neural network 500, in accordance with some embodiments. It should be noted that this description is used as an example only, and other types or configurations may be used to implement the embodiments described herein. The machine learning model 350 may be established based on the neural network 500. A corresponding model-based processing module 416 may apply the machine learning model 350 including the neural network 500 to process input data 422 that has been converted to a predefined data format. The neural network 500 may include a collection of nodes 520 that may be connected by links 512. Each node 520 may receive one or more node inputs 522 and applies a propagation function 530 to generate a node output 524 from the one or more node inputs. As the node output 524 is provided via one or more links 512 to one or more other nodes 520, a weight w associated with each link 512 may be applied to the node output 524. Likewise, the one or more node inputs 522 may be combined based on corresponding weights $w_1$, $w_2$, $w_3$, and $w_4$ according to the propagation function 530. In an example, the propagation function 530 is computed by applying a non-linear activation function 532 to a linear weighted combination 534 of the one or more node inputs 522.

The collection of nodes 520 may be organized into layers in the neural network 500. In general, the layers may include an input layer 502 for receiving inputs, an output layer 506 for providing outputs, and one or more hidden layers 504 (e.g., layers 504A and 504B) between the input layer 502 and the output layer 506. A deep neural network has more than one hidden layer 504 between the input layer 502 and the output layer 506. In the neural network 500, each layer may only be connected with its immediately preceding and/or immediately following layer. In some embodiments, a layer may be a "fully connected" layer because each node in the layer is connected to every node in its immediately following layer. In some embodiments, a hidden layer 504 may include two or more nodes that may be connected to the same node in its immediately following layer for down sampling or pooling the two or more nodes. In particular, max pooling may use a maximum value of the two or more nodes in the layer for generating the node of the immediately following layer.

In some embodiments, a convolutional neural network (CNN) may be applied in a machine learning model 350 to process input data. The CNN employs convolution operations and belongs to a class of deep neural networks. The hidden layers 504 of the CNN include convolutional layers. Each node in a convolutional layer may receive inputs from a receptive area associated with a previous layer (e.g., nine nodes). Each convolution layer may use a kernel to combine pixels in a respective area to generate outputs. For example, the kernel may be to a 3×3 matrix including weights applied to combine the pixels in the respective area surrounding each pixel. Video or image data can be pre-processed to a predefined video/image format corresponding to the inputs of the CNN. In some embodiments, the pre-processed video or image data may be abstracted by the CNN layers to form a respective feature map. In this way, video and image data can be processed by the CNN for video and image recognition or object detection.

In some embodiments, a recurrent neural network (RNN) is applied in the machine learning model 350 to process input data 422. Nodes in successive layers of the RNN follow a temporal sequence, such that the RNN exhibits a temporal dynamic behavior. In an example, each node 520 of the RNN has a time-varying real-valued activation. It is noted that in some embodiments, two or more types of input data may be processed by the data processing module 330, and two or more types of neural networks (e.g., both a CNN and an RNN) may be applied in the same machine learning model 350 to process the input data jointly.

The training process is a process for calibrating all of the weights $w_i$ for each layer of the neural network 500 using training data 346 that is provided in the input layer 502. The training process typically may include two steps, forward propagation and backward propagation, which may be repeated multiple times until a predefined convergence condition is satisfied. In the forward propagation, the set of weights for different layers may be applied to the input data and intermediate results from the previous layers. In the backward propagation, a margin of error of the output (e.g., a loss function) is measured (e.g., by a loss control module 412), and the weights may be adjusted accordingly to decrease the error. The activation function 532 can be linear, rectified linear, sigmoidal, hyperbolic tangent, or other types. In some embodiments, a network bias term b may be added to the sum of the weighted outputs 534 from the previous layer before the activation function 532 is applied. The network bias b may provide a perturbation that helps the neural network 500 avoid over fitting the training data. In some embodiments, the result of the training may include a network bias parameter b for each layer.

Figure 6A:
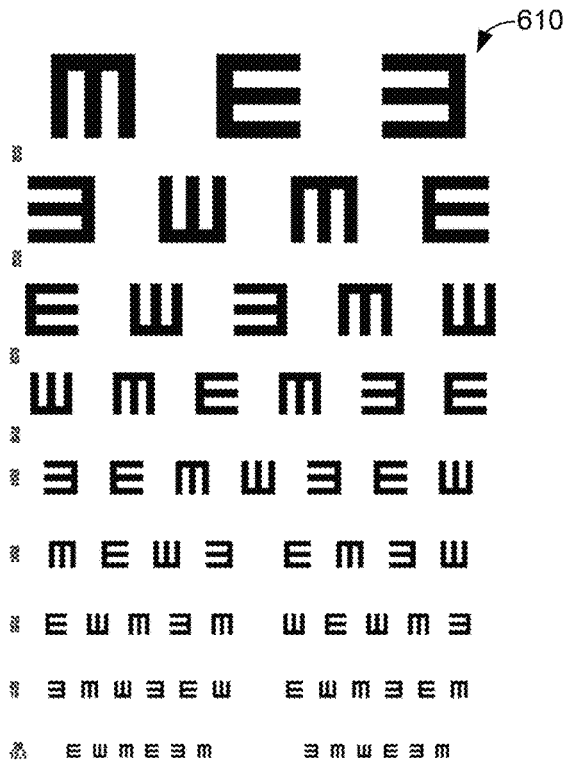
FIG. 6A is an example "tumbling E" chart applied in a visual acuity test, in accordance with some embodiments.
Figure 6B:
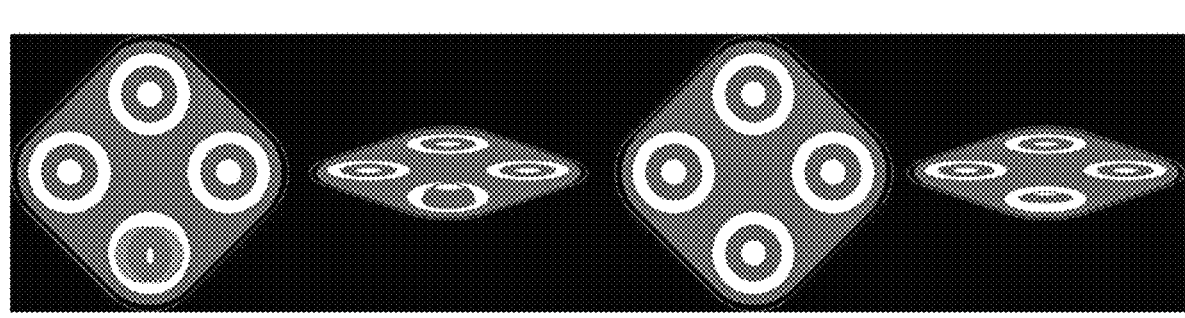
FIGS. 6B, 6C, 6D, and 6E are example patterns applied in an astigmatism test, a stereopsis test, a visual field test, and a color blindness test, in accordance with some embodiments.
Figure 6C:
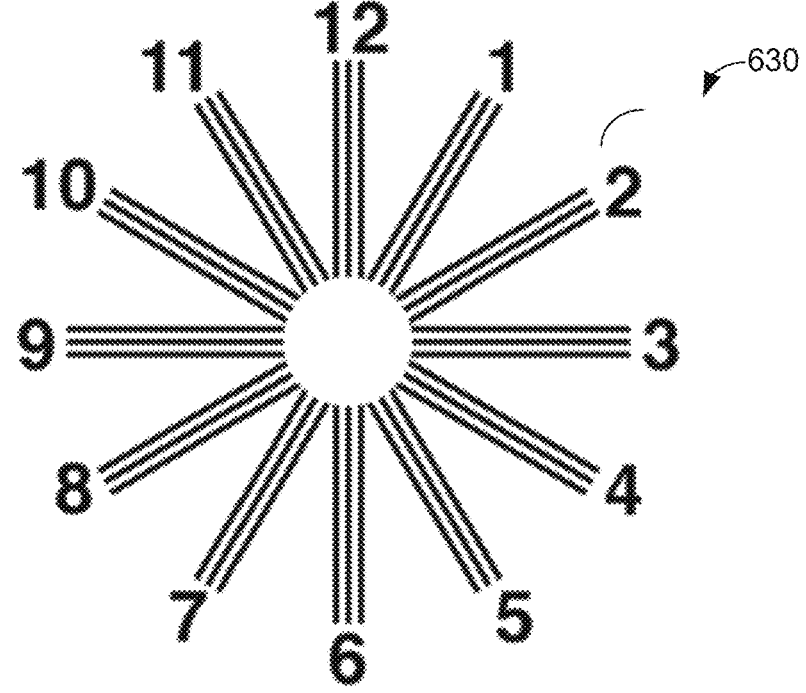
Figure 6D:
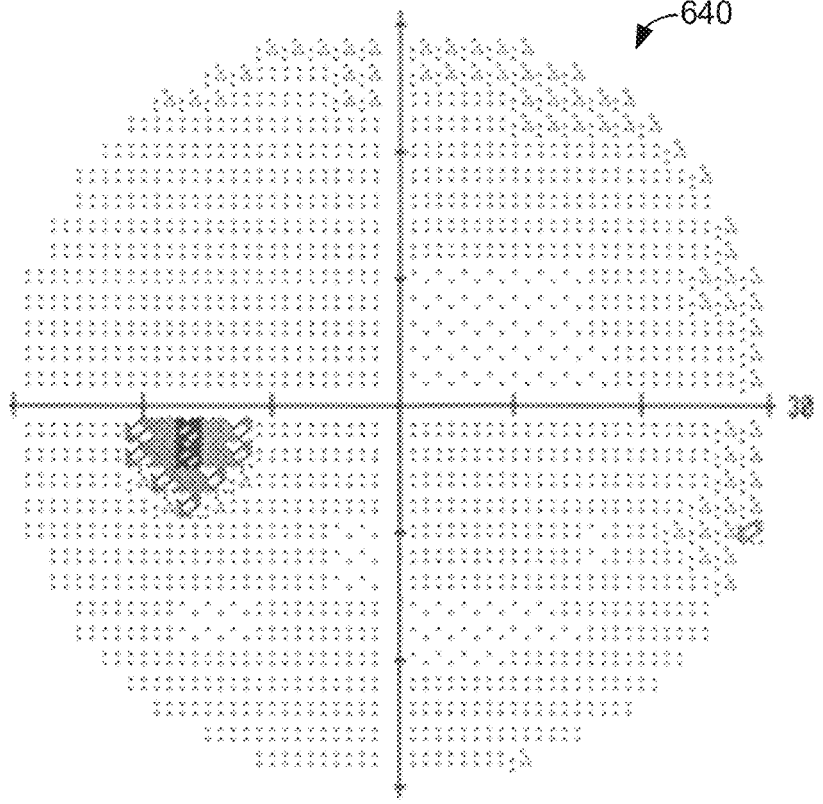
Figure 6E:
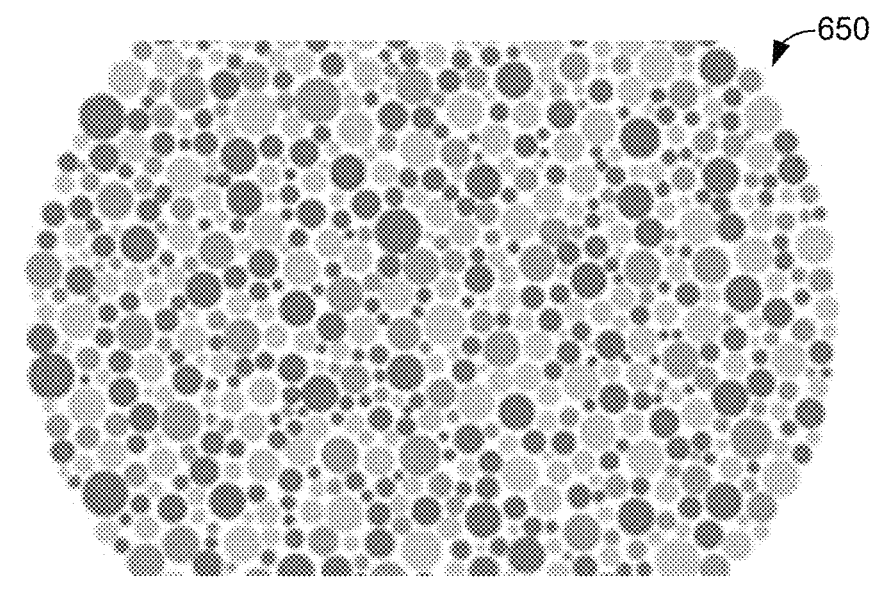

In some embodiments of the present disclosure, a vision test is implemented in a headset device 140D configured to display a user interface creating a three-dimensional (3D) virtual environment. Examples of a vision test implemented in the 3D virtual environment include, but are not limited to a visual acuity test, a visual field test, a visual depth test, a color blindness test, a retinoscopy, a test for stereopsis, a refraction test, an astigmatism test, and a contact lens exam. FIG. 6A is an example "tumbling E" chart 610 applied in a visual acuity test, in accordance with some embodiments. FIGS. 6B, 6C, 6D, and 6E are example patterns 620, 630, 640, and 650 applied in an astigmatism test, a stereopsis test, a visual field test, and a color blindness test, in accordance with some embodiments.

Figure 7:
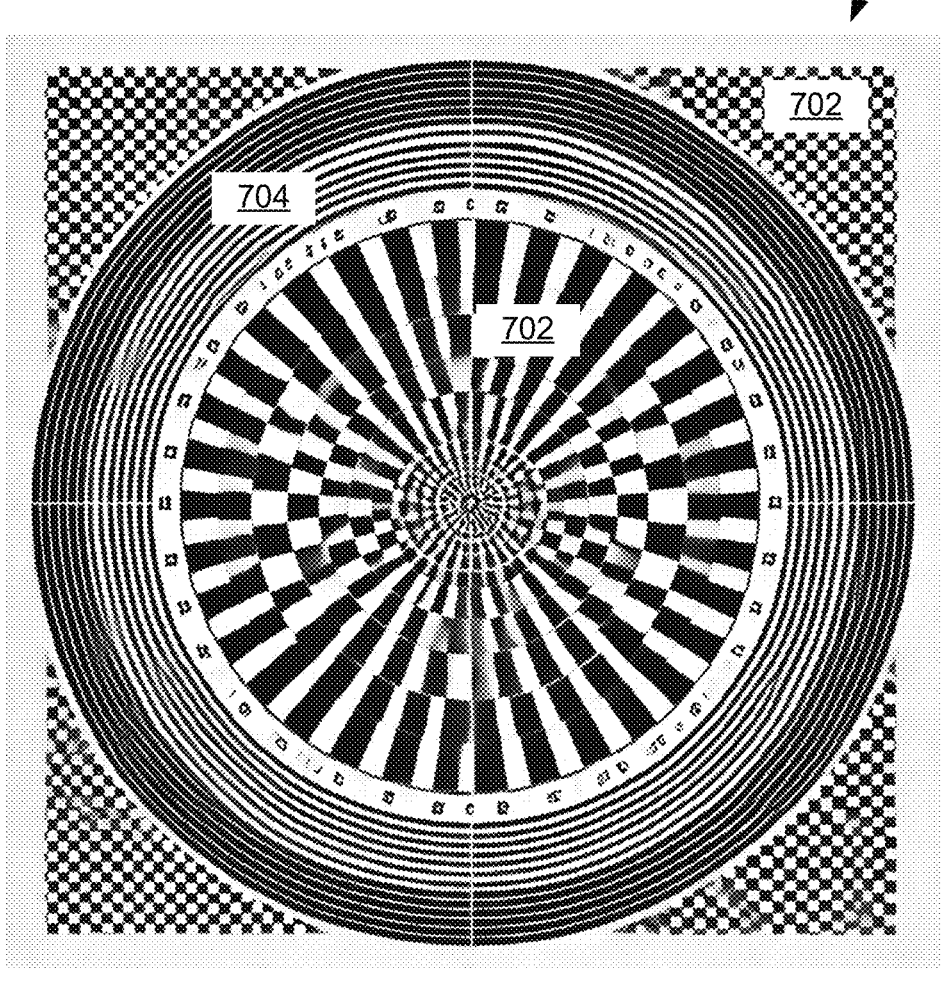
FIG. 7 is another example visual pattern applied to test visual acuity and astigmatism, in accordance with some embodiments.
Figure 8A:
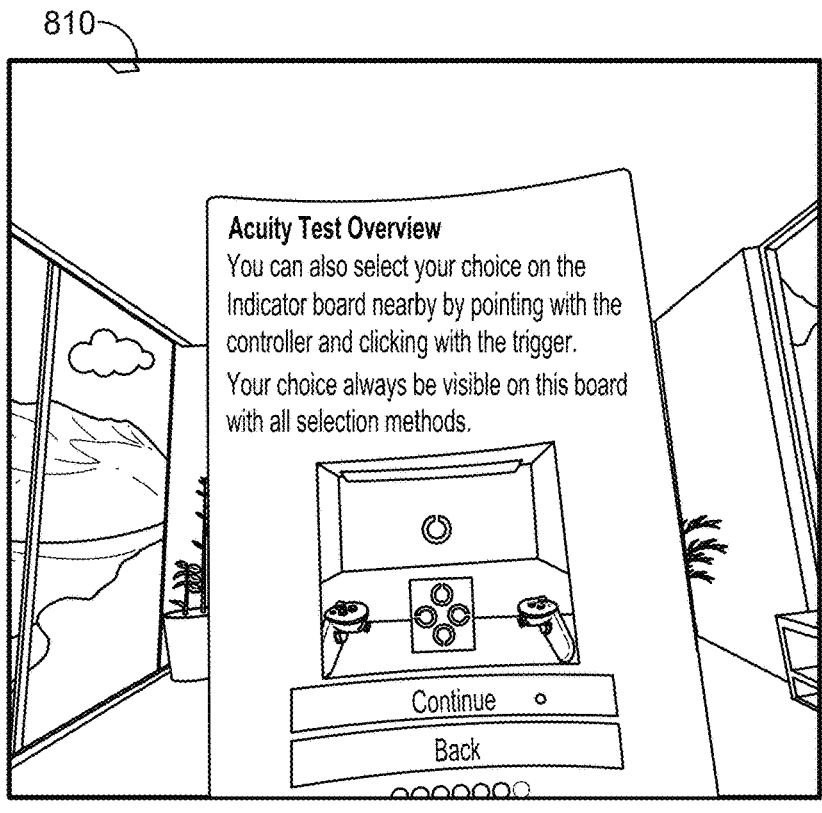
FIGS. 8A-8D include four diagrams of example graphical user interfaces rendered to determine a visual acuity score in a virtual environment created by a headset device, in accordance with some embodiments.
Figure 8B:
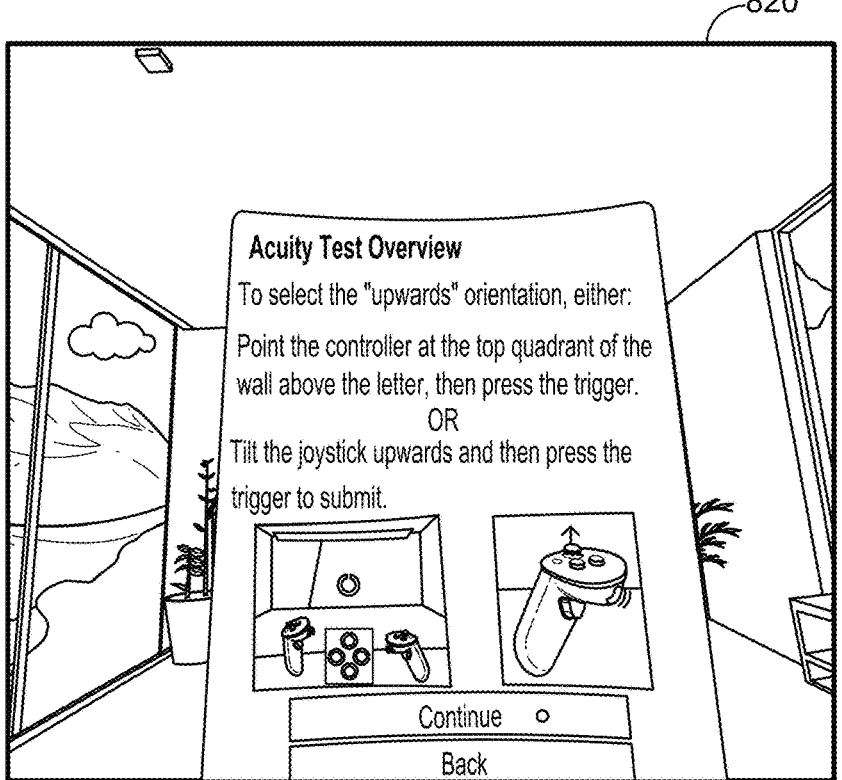
Figure 8C:
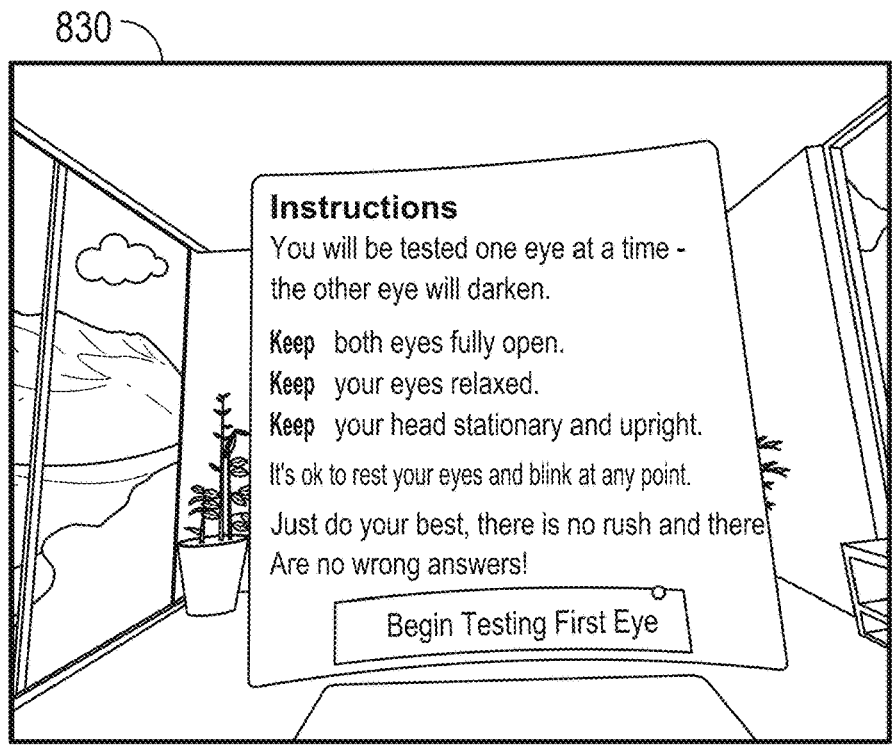
Figure 8D:
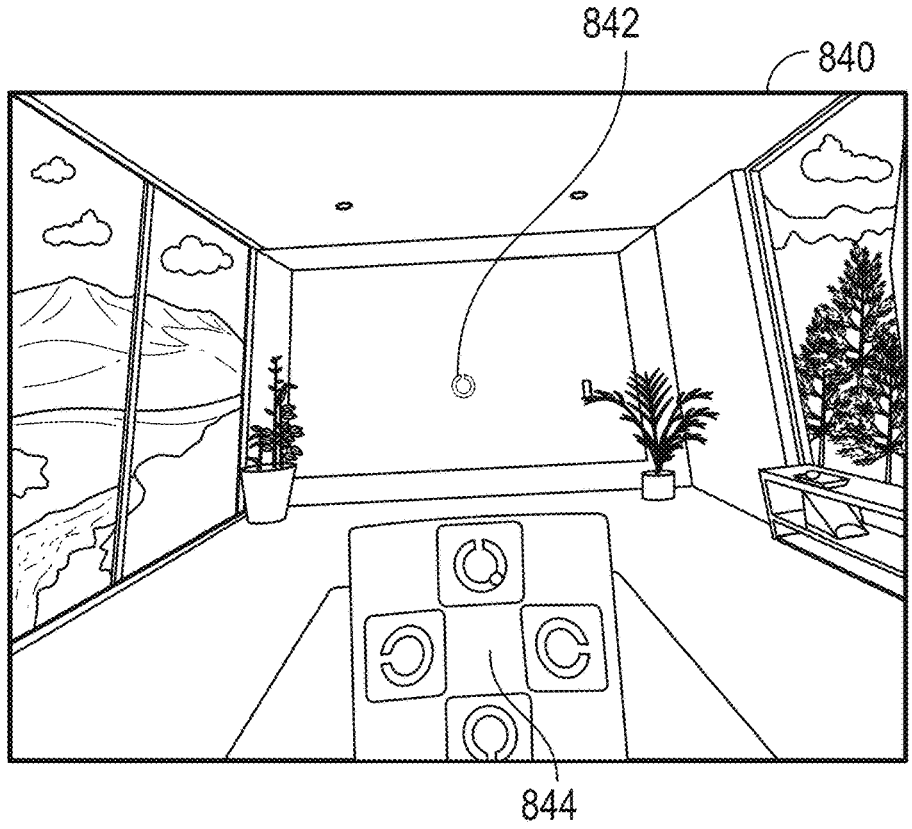

FIG. 7 is another example visual pattern 700 applied to test visual acuity and astigmatism, in accordance with some embodiments. The visual pattern 700 integrates a grid pattern 702 and concentric rings 704. The grid pattern 702 may include evenly spaced horizontal and vertical lines, creating a checkerboard pattern. The grid pattern 702 may be configured to identify distortions in straight lines, which can indicate issues with visual acuity and astigmatism. The concentric rings 704 may expand outward from a center of the visual pattern 700 and can assist in detecting radial distortions, which are common indicators of astigmatism. The visual pattern 700 may be depicted in high-contrast black and white, which ensures maximum clarity and reduces the potential for color-related distortions, making it easier to detect any visual impairment or defect.

FIGS. 8A-8D include four diagrams of example graphical user interfaces 810, 820, 830, and 840 rendered to determine a visual acuity score in a virtual environment created by a headset device 140D, in accordance with some embodiments. The user interface 810 may display an information page including instructions on controlling a headset device 140D to select one of a plurality of optotype candidates to match a target optotype displayed in the virtual environment. The user interface 820 may display an information page including two optional ways of using the controller to select the one of the plurality of optotype candidates. The user interface 830 may display an information page including general guidelines on a visual acuity assessment process. The user interface 840 may display an optotype 842 that is projected on a screen that has a first distance L1 from a user's position in the virtual environment. In a second distance L2 near the user, a selection panel 844 including a plurality of optotype candidates may be displayed, prompting the user to select one of the optotype candidates that matches the optotype 842. In some embodiments, in response to a user selection of the one of the optotype candidates, the optotype 842 displayed in the first distance L1 may be updated with a new optotype 842. Further, in some embodiments, the new optotype 842 may spin at a fast rate for a shortened duration of time (e.g., 2 seconds), before it settles in place of the original optotype 842. In an example, the optotype 842 may spin and gradually shrink in size during the shortened duration of time.

Figure 9C:
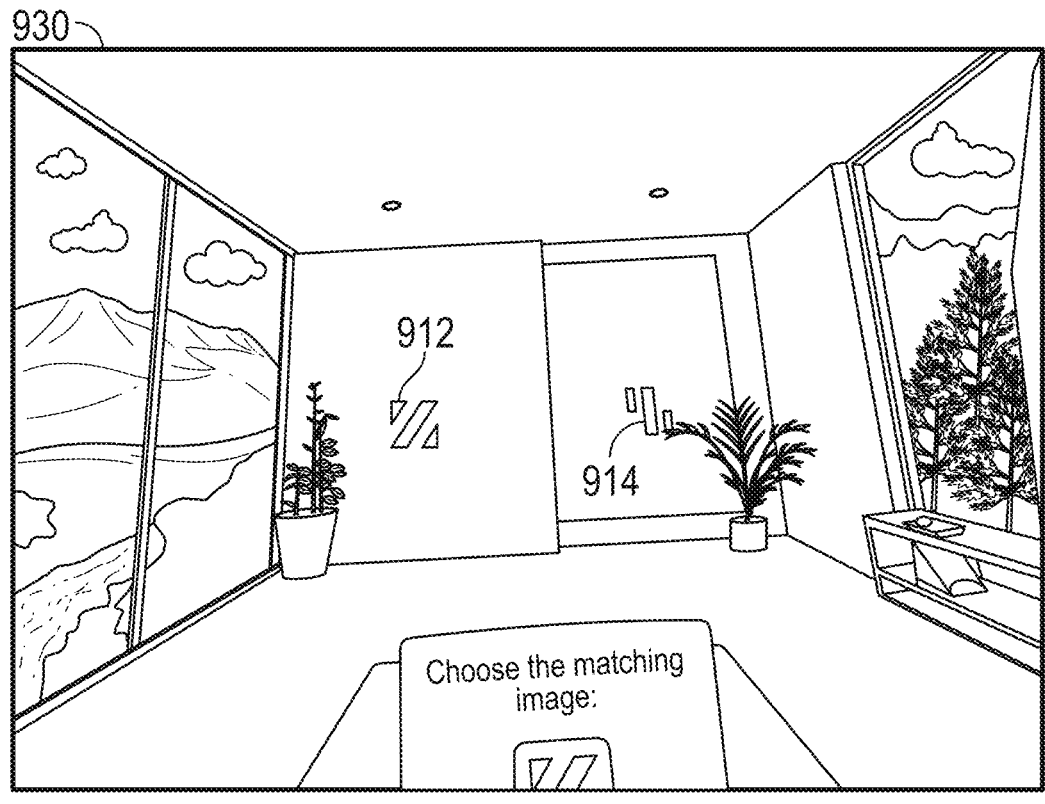

FIGS. 9A-9C include three diagrams of example graphical user interfaces 910, 920, and 930 rendered to determine a nearsighted or farsighted power in a virtual environment created by a headset device 140D, in accordance with some embodiments. The user interface 910 may display an information page explaining that two target optotypes 912 and 914 may be displayed in the virtual environment. The user interface 920 may display an information page including two optional ways of using the controller to select one of the two target optotypes 912 and 914. The user interface 930 may display two target optotypes 912 and 914 that may be projected on a screen that has a first distance L1 from a user's position in the virtual environment. In this example, the target optotype 912 located on the left is highlighted (e.g., by being displayed in a colored background). In a second distance L2 near the user, a confirmation panel 932 may be displayed, prompting the user to select one of the two target optotypes 912 and 914. In some embodiments, in response to a user selection of the one of the two target optotypes 912 and 914, the two target optotypes 912 and 914 displayed in the first distance L1 may be updated with a new pair of two target optotypes 912 and 914. Further, in some embodiments, each optotype 912 or 914 may spin at a fast rate for a shortened duration of time (e.g., 2 seconds), before it settles in place of the original optotype 912 or 914. In an example, the optotype 912 or 914 may spin and gradually shrink in size during the shortened duration of time.

FIGS. 10A-10F include six diagrams of example graphical user interfaces 1010, 1020, 1030, 1040, 1050, and 1060 rendered to determine eye stigmatism in a virtual environment created by a headset device 140D, in accordance with some embodiments. The user interface 1010 may display an information page explaining that a clock diagram of converging numbered lines 1012 (which is a type of optotype) is displayed in the virtual environment. For example, the user interface 1010 may include a message, e.g., "You will be presented with a clock diagram of converging numbered lines." The user interface 1020 may display an information page explaining what is selected on the clock diagram of converging numbered lines 1012 displayed in the virtual environment. For example, the user interface 1010 may include a message, e.g., "Your task is to identify if any of these sets of lines appear clearer, crisper, or darker than other." The user interface 1030 may display an information page including two optional ways of using the controller to select lines on the clock diagram of converging numbered lines 1012. For example, the user interface 1010 may include a message, e.g., "Make a selection by either pointing the controller at the lines on the clock, then pressing the trigger" and "Rotating the joystick to move the indicator arrows around the clock." The user interface 1040 may display an information page illustrating an embodiment having equally clear lines on the clock diagram of converging numbered lines 1012. For example, the user interface 1010 may include a message, e.g., "If two sets of neighboring lines seem to both stand out as equally clear, you can move the indicator arrows to a halfway point between those lines."

Figure 10A:
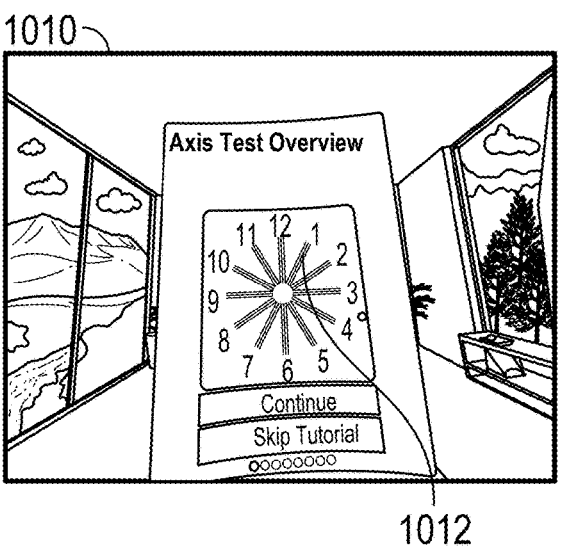
FIGS. 10A-10F include six diagrams of example graphical user interfaces rendered to determine eye stigmatism in a virtual environment created by a headset device, in accordance with some embodiments.
Figure 10B:
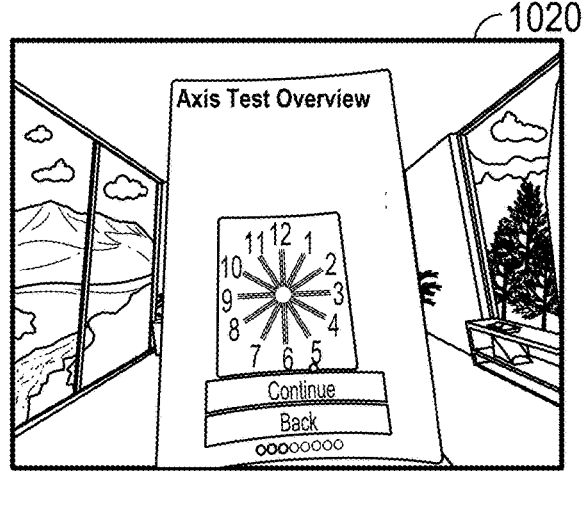
Figure 10C:
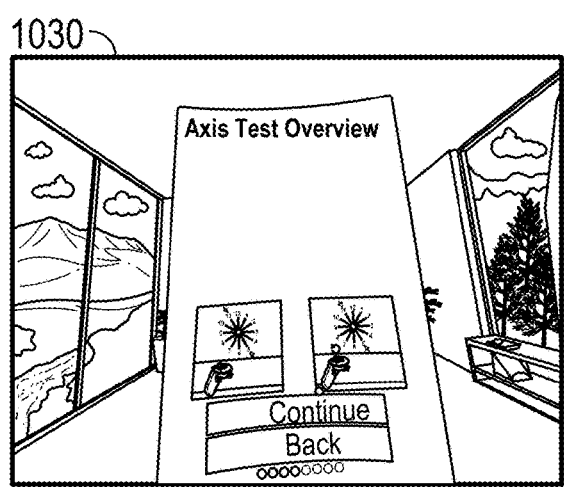
Figure 10D:
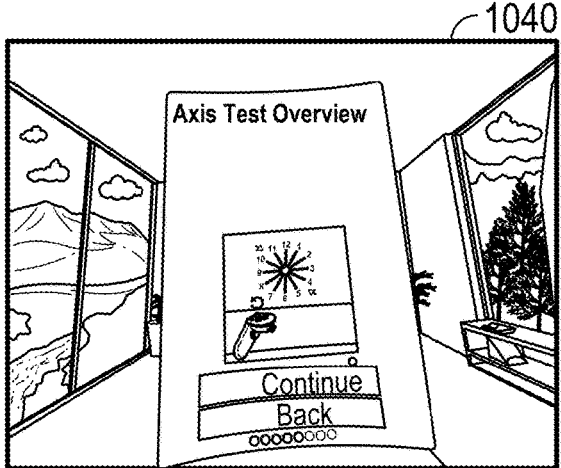
Figure 10E:
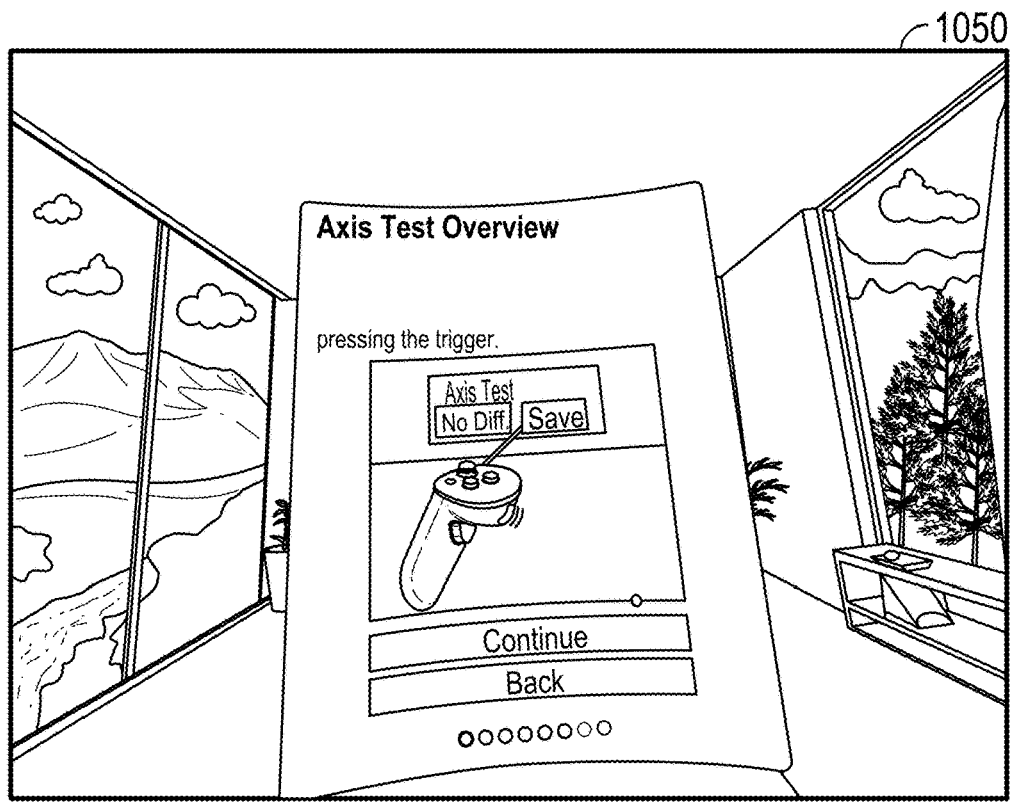
Figure 10F:
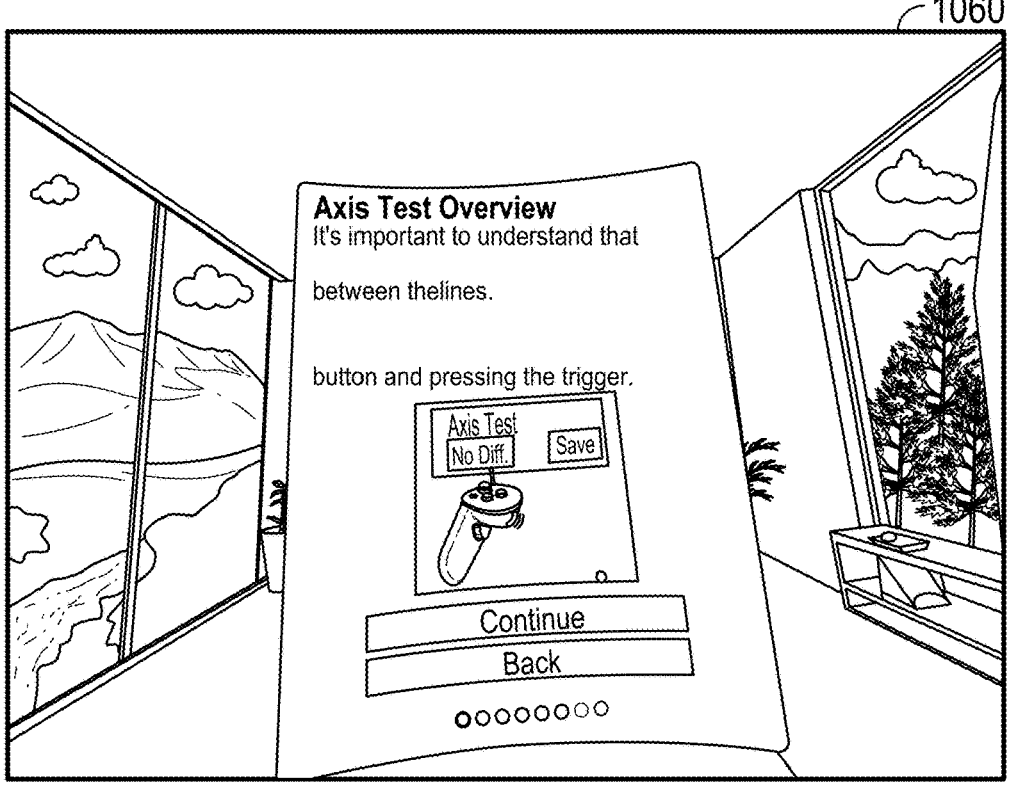

Referring to FIG. 10E, the user interface 1050 may display an information page including an instruction using the controller to submit a selection. For example, the user interface 1010 may include a message, e.g., "After selecting a set of lines, submit your choice with the 'Done' button below by pointing to the controller at the button and pressing the trigger." Further, referring to FIG. 10F, the user interface 1060 may display an information page including an instruction using the controller to indicate that no difference is observed on the clock diagram of converging numbered lines 1012. For example, the user interface 1010 may include a message, e.g., "It's important to understand that not everybody will see a difference between the lines" and "In this case, simply select 'No Difference' below, by positioning the controller at the button and pressing the trigger."

Evaluating Eye Movement Disorders Through Eye-Tracking Exercises

A person must use different eye muscles to move her eyes in different directions. Specifically, the superior rectus (SR) is a muscle on top of the eye that moves the eye upward; the inferior rectus (IR) is a muscle on the bottom of the eye that moves the eye downward; the medial rectus (MR) is a muscle on the portion of the eye that is near the nose and moves the eye inward (toward the nose); the lateral rectus (LR) is a muscle on the portion of the eye that is near the ear and moves the eye outward (toward the ear); the superior oblique (SO) is a muscle that starts at the back of the eye socket, passes by the nose, and attaches to the top of the eye to rotate the eye inward, move the eye downward, and move the eye outward; and the inferior oblique (IO) is a muscle that starts at the front of the eye socket near the nose and attaches to the bottom of the eye to rotate the eye outward, move the eye upward, and move the eye outward. Because each of these muscles is innervated by a different optical or cranial nerve and is responsible for a different type of eye movement, the way a person's eye or eyes move in different quadrants of the eyes can provide valuable information that can help physicians identify problems with the person's optic and cranial nerves. Consequently, by assessing a person's eye movements, a physician can identify compressed nerves, diabetic retinopathy, and tumorous growths around the eye—to name a few.

Traditionally, physicians assess a patient's eye movements through a subjective observation. A physician might ask a patient to look between two objects on a screen or two lights in a room. As the patient's eye or eyes move from one object to the other, the physician observes the patient's pursuit and saccadic eye movements. However, while the physician can identify in which direction the patient is looking, the physician has no means of quantifying the patient's eye movements, which leads to a subjective and inaccurate assessment. Moreover, this traditional method is limiting in that it is very difficult for a physician to rearrange the objects in the room that the patient must look at, which means that the physician cannot observe a wide range of eye movements from the patient. By using a VR assessment to observe the patient's eye movements, a physician can collect objective and comprehensive data about the patient's eye movements, which results in accurate evaluations for eye movement disorders.

A VR system for administering eye-tracking exercises in order to evaluate eye movement disorders includes a VR headset in electronic communication with a computing device. The VR headset is worn by the patient being evaluated and includes screens, eye-tracking sensors, and eye-tracking cameras. The screens are configured to display the virtual environments and virtual objects that the patient views and interacts with during the eye-tracking exercises. The eye-tracking sensors and eye-tracking cameras are configured to collect information about the eye movements of the patient as the patient participates in the eye-tracking exercises. In particular, the eye-tracking sensors and eye-tracking cameras are configured to collect data about the accuracy, speed, and coordination of the patient's eye movements. In some embodiments, the eye-tracking sensors are configured to collect the eye movement data in real-time and communicate the eye movement data to the computing device in real-time. Optionally, the eye-tracking sensors and cameras are infrared sensors and cameras. Optionally, there is at least one eye-tracking camera pointed at each pupil of the patient when the patient wears the VR headset.

In some embodiments, a handheld device (e.g., a controller or a VR handset) is in electronic communication with the VR headset and the computing device. The patient can use the handheld device to interact with the eye-tracking exercises administered on the screens of the VR headset. For example, the patient can press a button to confirm that she is perceiving an object on the screen, use a controller to type in or select a brief description of the object, or even click on the object in the virtual environment.

The computing device of the VR system is configured to cause one or more virtual objects and optotypes to be displayed at various positions in a virtual environment. In some embodiments, the characteristics (e.g., brightness, contrast, size, color, shape, etc.) of the virtual objects and optotypes, the various positions of the virtual objects and optotypes in the virtual environment, the characteristics (e.g., brightness, contrast, saturation, amount of movement, type of scenery, etc.) of the virtual environment, and other aspects of the eye-tracking exercises are determined by an algorithm. For example, the algorithm might change various of the aforementioned elements to increase the difficulty of the eye-tracking exercises if the patient is easily completing the exercises. Optionally, the algorithm might position the virtual objects and optotypes in the upper right corner of the patient's field of vision if it recognizes that she is struggling in that area. This would help the VR system gather more information about the patient's problem areas, which would lead to a narrower and more tailored evaluation.

The computing device is also configured to receive the eye movement data from the VR headset and inputs from the handheld device. Upon receipt of the data and the inputs, the computing device processes the data and the inputs to identify eye movement patterns of the patient. In some embodiments, an algorithm processes the eye movement data and the inputs to identify eye movement patterns of the patient. Optionally, the algorithm compares the patient's eye movement patterns to a database of eye movement patterns from individuals with known ocular motor statuses to determine whether the patient has healthy eye movements. In some embodiments, the computing device generates a report summarizing the patient's eye movement patterns, diagnosing eye movement disorders, listing treatment and evaluation recommendations, and predicting future eye movement disorders. This report can be accessed by a physician, the patient, or the patient's caretaker at a user interface in the computing device.

To begin the eye movement evaluation, the patient dons the VR headset. The computing device causes a virtual environment to be displayed on the screens of the VR headset. The computing device also causes an object to be displayed in the virtual environment at a first position, which is demonstrated in FIG. 11A.

Figure 11A:
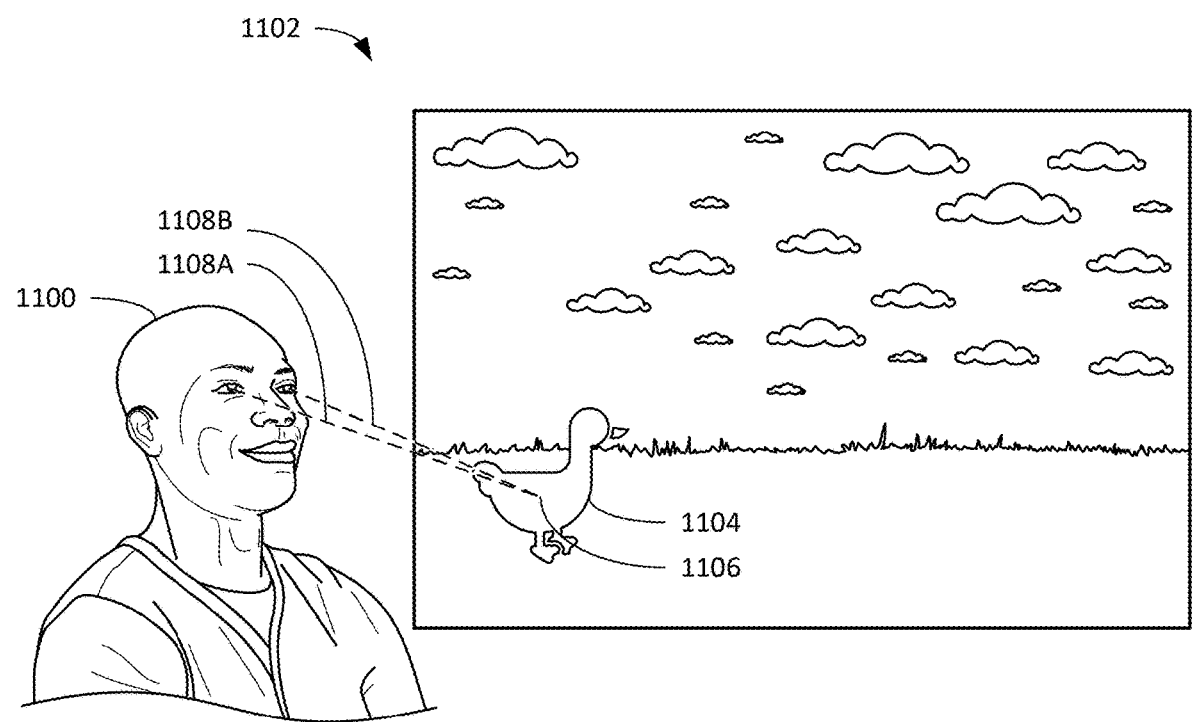
FIG. 11A illustrates a patient visually tracking an object at a first position in a virtual environment as part of an eye-tracking exercise, in accordance with some embodiments.

FIG. 11A illustrates a patient visually tracking an object at a first position in a virtual environment as part of an eye-tracking exercise, in accordance with some embodiments. As shown, the patient 1100 is viewing a virtual environment 1102, which can be displayed on screens of a VR headset (not shown). The virtual environment 1102 includes a virtual object 1104 (in this example, a virtual duck) at a first position 1106. In some embodiments, the virtual environment 1102 includes multiple virtual objects 1104.

When the virtual object 1104 is displayed at the first position 1106, the patient 1100 moves his eyes to the first position 1106 to look at the object 1104. This is indicated in FIG. 11A by dashed lines 1108A and 1108B, which correspond with the gaze point of the patient's right and left eyes, respectively. The VR headset (in particular, the sensors and cameras positioned on the VR headset) monitors the eye movements of the patient 1100—including the gaze points 1108A, 1108B—as the patient 1100 looks at the object 1104 in the first position 1106 to gather a first input. The first input comprises the accuracy and speed of the patient's eye movements as the patient's eye or eyes move to look at the object 1104 in the first position 1106. The first input also comprises the coordination between the patient's left and right eyes as the patient tries to look at the object 1104 in the first position 1106. The accuracy and coordination of the patient's eye movements are discussed in greater detail below with respect to FIGS. 12A-12C.

In addition to the sensors and cameras of the VR headset being configured to identify the exact point of the patient's gaze (indicated by dashed lines 1108A and 1108B in FIG. 11A), some embodiments include receiving subjective input from the patient that confirms when the patient is looking at the object 1104 in the first position 1106. For example, the screens of the VR headset might show a prompt asking the patient 1100 to verbally confirm that he is looking at the object 1104 in the first position 1106, or the patient might be asked to use a handheld device to click on the object 1104 in the first position 1106. Incorporation of the patient's subjective input can be used to identify discrepancies between what the patient 1100 is seeing and how the patient's eyes are moving, which can be used to predict or diagnose eye movement disorders.

After monitoring the eye movements of the patient and receiving the first input and/or the subjective input, the object 1104 is displayed in a second position of the virtual environment. This is shown in FIG. 11B, which is described in greater detail below.

Figure 11B:
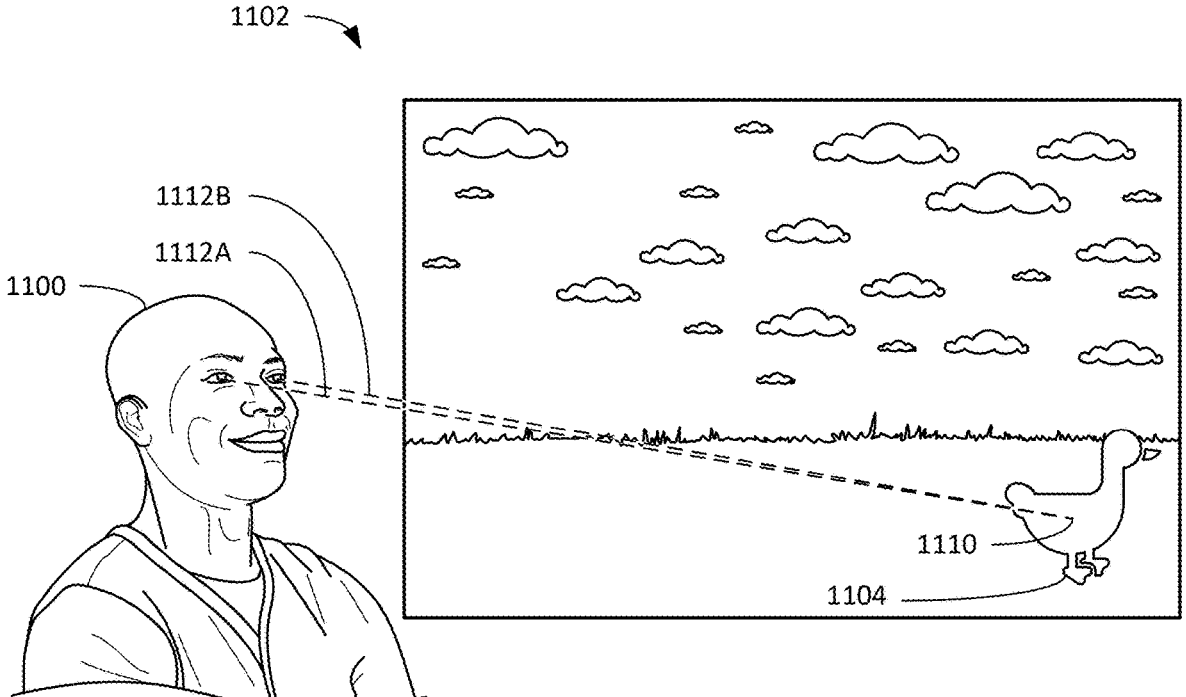
FIG. 11B illustrates a patient visually tracking an object at a second position in a virtual environment as part of an eye-tracking exercise, in accordance with some embodiments.

FIG. 11B illustrates a patient visually tracking an object at a second position in a virtual environment as part of an eye-tracking exercise, in accordance with some embodiments. In FIG. 11B, the virtual object 1104 is now displayed at a second position 1110, and the patient's gaze points 1112A and 1112B (which correspond to the gaze points of the patient's right and left eyes, respectively) have moved to view the object 1104 at the second position 1110. Similar to the process described above with respect to the first position 1108 in FIG. 11A, the VR headset monitors the patient's eye movements as the patient 1100 looks at the object 1104 in the second position 1110 to gather a second input. second first input comprises the accuracy and speed of the patient's eye movements as the patient's eye or eyes move to look at the object 1104 in the second position 1110. The second input also comprises the coordination between the patient's left and right eyes as the patient tries to look at the object 1104 in the second position 1110.

In some embodiments, the VR method for assessing eye movement disorders also includes receiving subjective input from the patient that confirms when the patient is looking at the object 1104 in the second position 1110, as described above with respect to the first position 1106.

There are several ways in which the object 1104 can be displayed in the virtual environment 1102 and moved between the first position 1106 and the second position 1110. In some embodiments, the object 1104 instantly appears in the first position 1106, the object 1104 instantly disappears from the first position 1106, the object 1104 instantly appears in the second position 1110, and the object 1104 instantly disappears from the second position 1110. In other embodiments, the object 1104 is faded into the first position 1106, faded out of the first position 1106, faded into the second position 1110, and faded out of the second position 1110. Optionally, the object 1104 can be displayed in the virtual environment 1102 using a combination of instantly appearing/disappearing and fading. This display of the object 1104 can be described as static and is useful for evaluating saccadic movements of the patient's eyes.

In some embodiments, the object 1104 remains visible in the virtual environment 1102 while the object 1104 is transported from the first position 1106 to the second position 1110. For example, the object 1104 might travel along a continuous path between the first position 1106 and the second position 1110. This path might be a straight line, a curved path, a smooth path, jagged path, or a randomized path. When the display of the object 1104 is dynamic in this manner, the patient 1100 engages different parts of his retina and engages in pursuit movements. Optionally, the object 1104 can travel at different speeds. For example, the object 1104 can be shown to travel at faster speeds to make tracking the object 1104 more difficult, which is useful for evaluating the outer limits of the patient's pursuit movement capabilities.

In other embodiments, the first and second positions 1106, 1110 of the object 1104 are changed incrementally to gather detailed information about the specific parts of the patient's field of vision at which the patient's eye movements change. Incremental changes can also be used to tracks changes in saccades and smooth pursuits as the eye movements get more challenging. For example, the object 1104 might be displayed five degrees left of a center point in the virtual environment, then five degrees right of the center point, 10 degrees left of the center point, 10 degrees right of the center point, etc. These increments can be any number of degrees, above and below the center point, radially around the center point, etc. In some embodiments, the increments can be above or below an X-axis of the virtual environment 1102. Optionally, the increments can be to the left or right of a Y-axis of the virtual environment 1102.

Figure 11C:
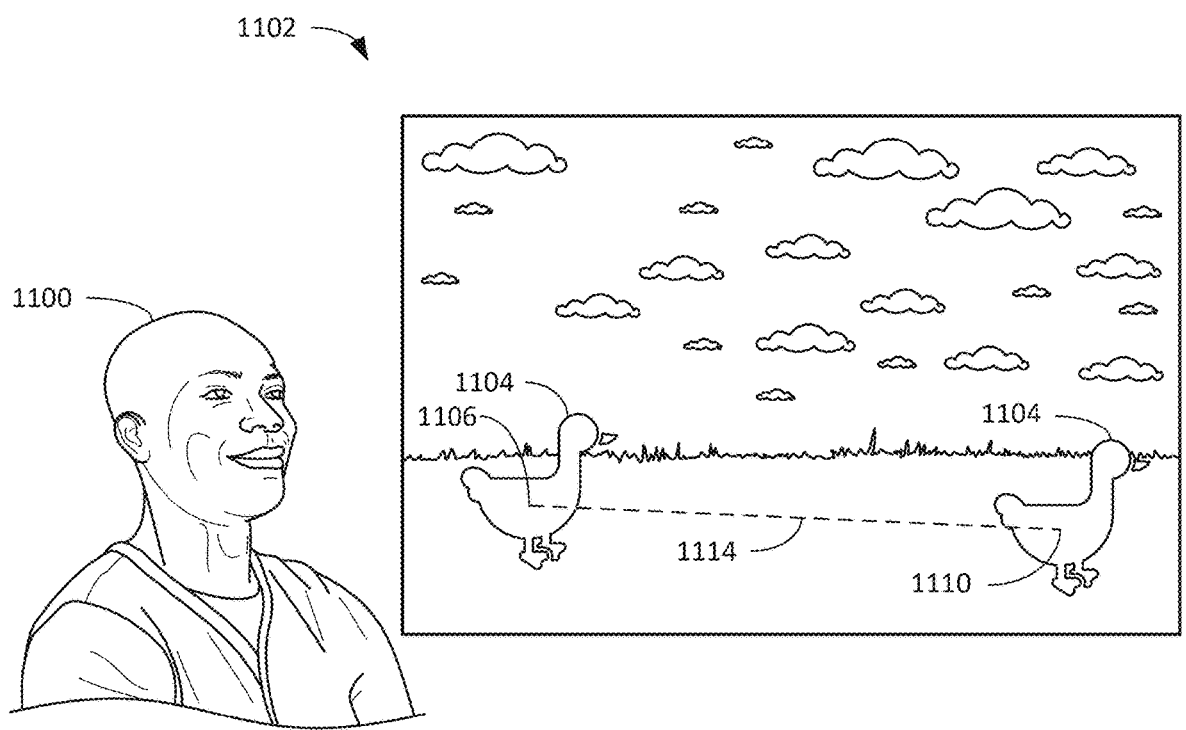
FIGS. 11C-11D illustrate a patient visually tracking an object as it moves between a first position and a second position in a virtual environment as part of an eye-tracking exercise, in accordance with some embodiments.
Figure 11D:
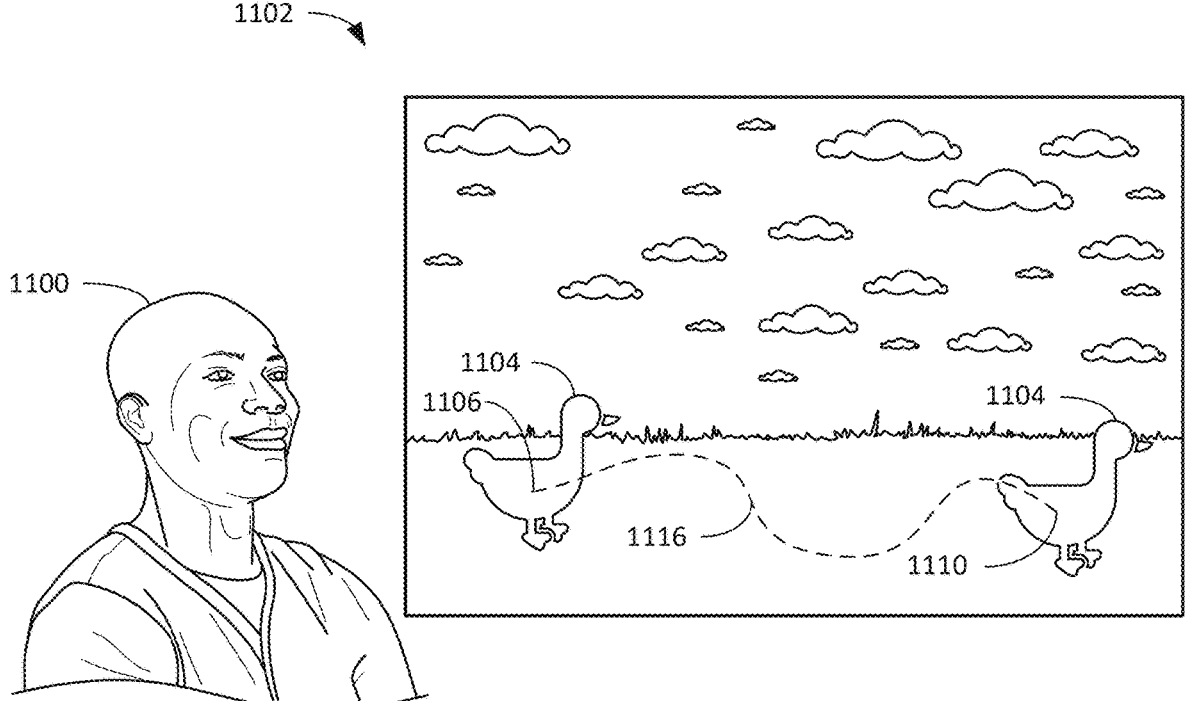

FIGS. 11C-11D illustrate a patient visually tracking an object as it moves between a first position and a second position in a virtual environment as part of an eye-tracking exercise, in accordance with some embodiments. As shown the object 1104 is moved from a first position 1106 to a second position 1110 in a virtual environment 1102. The patient 1100 views the object 1104 as it is moved, and the path of the patient's eye movements is indicated by dashed lines 1114 (in FIG. 11C) and 1116 (in FIG. 11D).

In some embodiments of the VR evaluation method, the patient's eye movements might be continuously monitored by the VR headset, which means that the VR headset can track the patient's eyes as he switches from looking at the object 1104 at the first position 1106 to looking at the object 1104 at the second position 1110. By continuously monitoring the patient's eye movements throughout the duration of the evaluation, the VR headset can identify whether the patient 1100 moves his eyes from the first position 1106 to the second position 1110 via a direct path 1114 (as shown in FIG. 11C) or an indirect path 1116 (as shown in FIG. 11D). The patient's 1100 use of an indirect path 1116 can be indicative of problems with the patient's eye muscles (e.g., the eye muscles hinder the patient from moving his eyes directly to the right, so the eyes have to move towards the right in a roundabout manner) and can also inform the patient 1100 when he is overexerting his eye muscles by moving his eyes more than necessary.

Continuously monitoring the patient's eye movements is also useful for identifying a delay between the time at which the object 1104 is displayed at the first or second positions 1106, 1110 and the time at which the patient's eyes reach the first or second positions 1106, 1110. Most people have a delay of 1 second or less, so if a patient has a delay that is greater than 1 second, this might indicate a weakness in the patient's eye muscles and, thus, problems with the optic or cranial nerves.

Figure 12A:
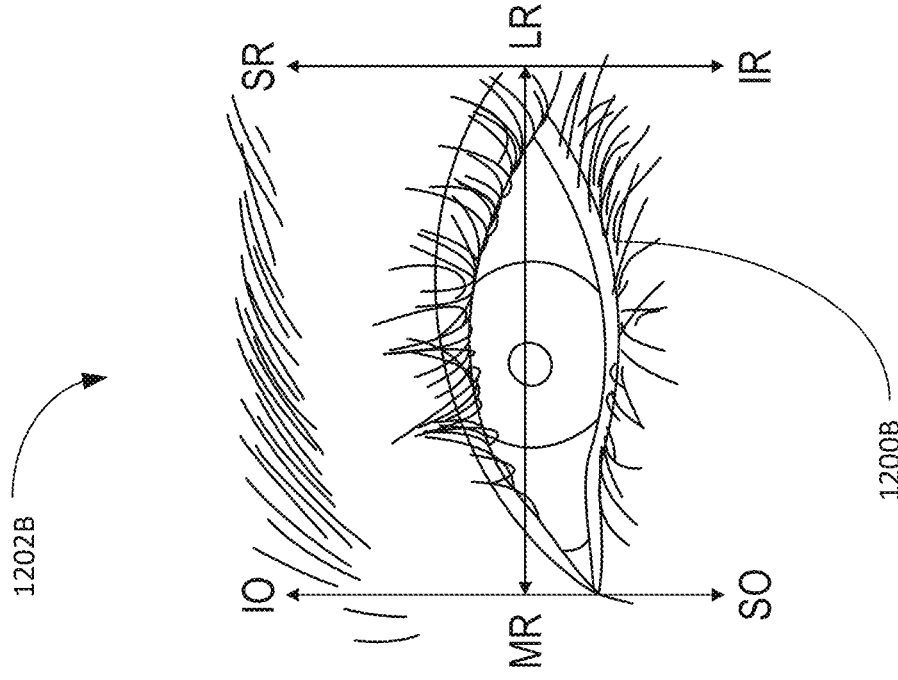
FIG. 12A illustrates a chart of the cardinal gaze positions labeled with the extraocular muscles that correspond with the gaze positions, accordance with some embodiments.
Figure 12A:
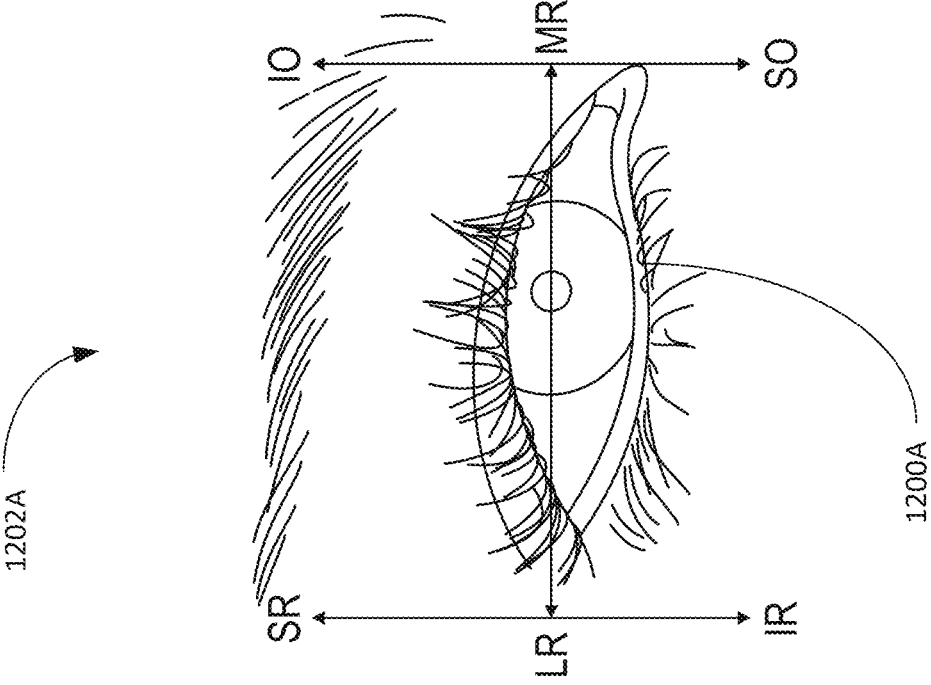

Some methods of the VR method for evaluating eye movements include quantifying deviation angles of the patient's eye movements. FIG. 12A illustrates a chart of the cardinal gaze positions labeled with the extraocular muscles that correspond with the gaze positions, accordance with some embodiments. FIG. 12A shows charts 1202A and 1202B over the right eye 1200A and the left eye 1200B, respectively. The charts 1202A, 1202B are an "H" diagram of the different directions in which the eyes 1200A, 1200B can look, and the charts 1202A, 1202B are labeled with the extraocular muscles that correspond with those directions.

Figure 12B:
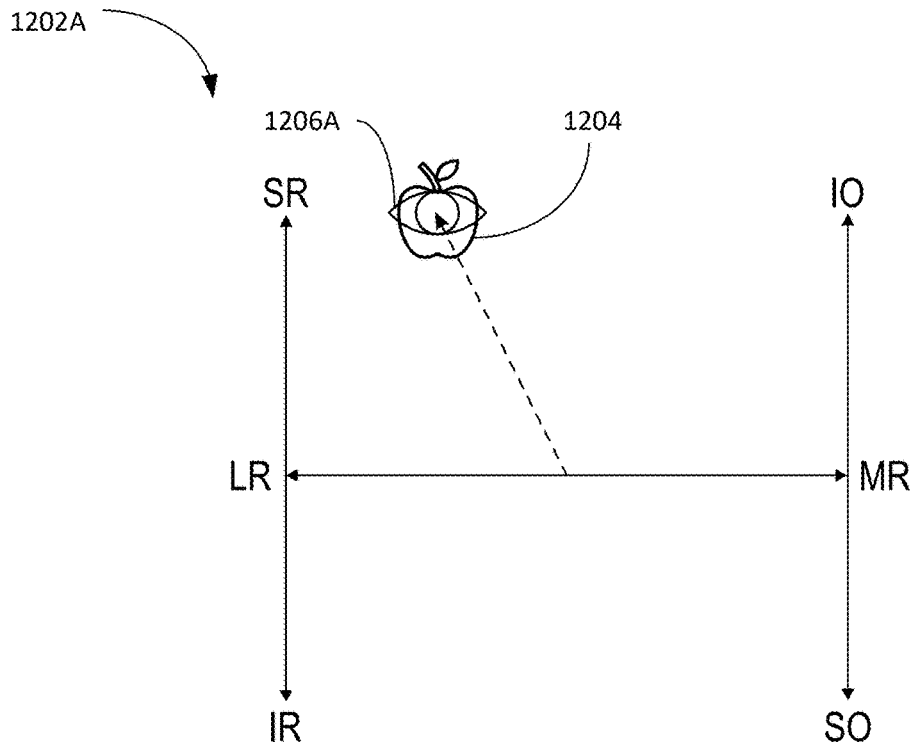
FIG. 12B illustrates a deviation angle of zero between the gaze point of the patient's right eye and the virtual object, in accordance with some embodiments.

FIG. 12B illustrates a deviation angle of zero between the gaze point of the patient's right eye and the virtual object, in accordance with some embodiments. When the patient is shown a virtual object at a certain position in a virtual environment (e.g., the virtual object 1104 in the first position 1106 of the virtual environment 1102 in FIG. 11A), the patient must move his eyes around the virtual environment (to different gaze positions) to locate the virtual object. The certain position of the virtual object (e.g., the first position 1106 of the virtual object 1104 in FIG. 11A) can be referred to as the target gaze position, and the actual gaze position of the patient (which is indicated by the dashed lines 1108A, 1108B in FIG. 11A) can be referred to as the patient's right and left gaze positions. In FIG. 12B, the target gaze position 1204 is represented by an apple symbol, and the patient's right gaze position 1206A is represented by an eye symbol.

The target gaze position 1204 and the patient's right gaze position 1206A are shown in the context of the chart 1202A (which is a diagram of the different directions in which the right eye 1200A can move) because the target gaze position 1204 and the patient's right gaze position 1206A correspond with the direction indicated on the chart 1202A. Specifically, in FIG. 12A, the patient's right gaze position is in upper right portion of the patient's field of vision, which largely requires use of the SR, in addition to the LR and IO.

The deviation angle represents the discrepancy between the target gaze position 1204 and the patient's right gaze position 1206A (as well as the patient's left gaze position). In FIG. 12B, the target gaze position 1204 and the patient's right gaze position 1206A are aligned, which results in a deviation angle of 0°. This would suggest that the patient's eye coordination in the upper right portion of his field of vision is very accurate. The deviation angle can vary as the target gaze position 1204 is moved around the chart 1202A. For example, while the patient has a deviation angle of 0° in the upper right portion of his field of vision, he might have a deviation angle of 1.5° in the upper left portion of his field of vision (which is still considered good) and a deviation angle of 6° in the lower left portion of his field of vision (which is considered unhealthy). A deviation angle greater than 5° can indicate problems with the extraocular muscles (in this particular example, the SO, IR, or MR might be improperly formed), which can indicate problems with the optical or cranial nerves. The deviation angle can also differ between each of the patient's eyes, as demonstrated in FIG. 12C.

Figure 12C:
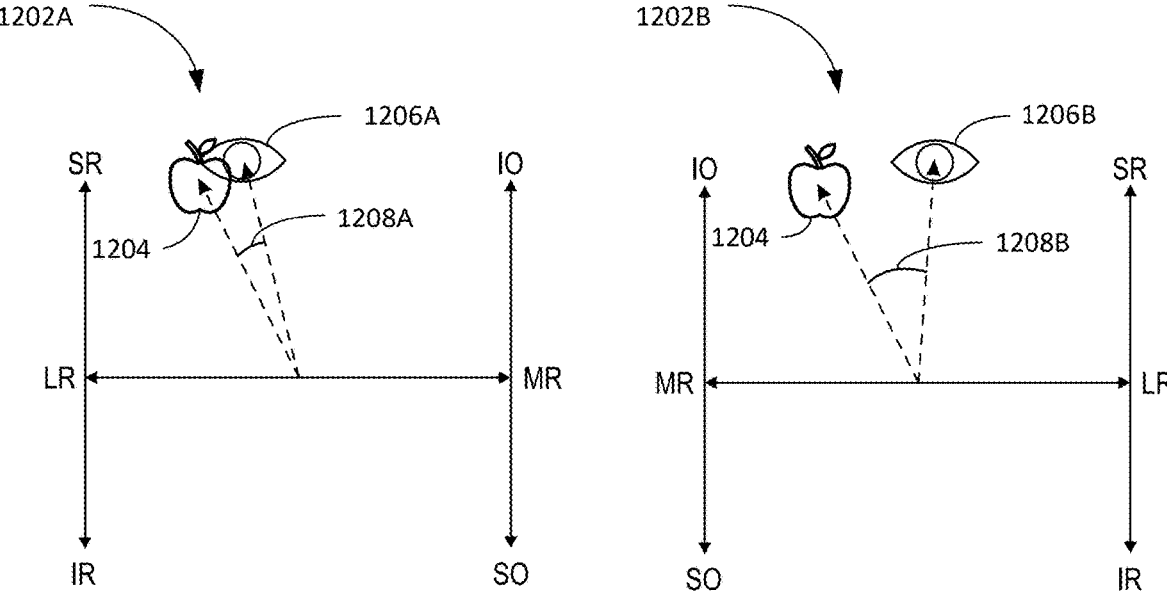
FIG. 12C illustrates the deviation angles between the gaze points of the patient's right and left eyes and the virtual object, in accordance with some embodiments.

FIG. 12C illustrates the deviation angles between the gaze points of the patient's right and left eyes and the virtual object, in accordance with some embodiments. The chart 1202A for the patient's right eye shows a deviation angle 1208A between the target gaze position 1204 and the patient's right gaze position 1206A. The chart 1202B for the patient's left eye shows a deviation angle 1208B between the target gaze position 1204 and the patient's left gaze position 1206B. (Please note that the deviation angles 1208A and 1208B are exaggerated for clarity of the figures.) As shown, the deviation angle 1208A of the patient's right eye is smaller than the deviation angle 1208B of the patient's left eye, which indicates that the patient has greater eye tracking accuracy in his right eye (at least in the upper right portion of his field of vision).

In some embodiments, the method also includes calculating an amount of deviation reduction between the patient's right and left eyes, which is the difference in the deviation angle between the patient's right and left eyes. Traditionally, this is measured using prism diopters, which is a subjective and inaccurate means of estimating deviation reduction. Because this VR method facilitates the exact quantification of the deviation angle in each of the patient's eyes, this VR method also facilitates the exact quantification of deviation reduction. For example, we can quantify deviation reduction as a ratio or percentage of the angle of deviation in one eye versus the angle of deviation in the other eye. Optionally, the method includes recommending that the patient seek further ocular examinations of the deviation reduction is 30% or more. High ratios or percentages of deviation reduction can be indicative of eye movement disorders such as nystagmus, strabismus, amblyopia, etc. Optionally, the method includes recommending that the patient seek further ocular examinations of the deviation reduction is 25% or more. Optionally, the method includes recommending that the patient seek further ocular examinations of the deviation reduction is 20% or more.

In some embodiments, the method includes comparing the eye movement information collected during the evaluation to a database of eye movement data from individuals with known ocular statuses (e.g., known to have strabismus, known to have healthy eye movements, etc.) in order to determine whether the patient has one or more eye movement disorders. Optionally, the comparison can be used to determine a severity of one or more eye movement disorders. In some embodiments, the comparison is conducted in real-time as the patient tracks the virtual object as it moves throughout the virtual environment.

In other embodiments, the method includes generating a report that summarizes the patient's eye movement patterns as well as abnormalities in the patient's eye movement patterns. Physicians can use this report to diagnose eye movement disorders and monitor progression of eye movement disorders. In home-care settings, patients can also use this report to monitor the progression of their eye movement disorders.

Optionally, the method includes recommending treatment for one or more eye movement disorders. Optionally, the method includes recommending further evaluation for eye movement disorders.

Testing Reaction Time in Virtual Space

On average, people have a reaction time of approximately 250 milliseconds. In some careers (e.g., professional sports, the military, and pilots), people must have shorter reaction times to perform their jobs properly and safely. Traditionally, reaction time is measured using a board with an array of pegs that can light up. A person must press or pull on the different pegs as they light up, and the board measures her reaction time based on the difference between the time at which the pegs lit up and the time at which the person pressed the pegs. However, this traditional method of measuring reaction time is subject to inaccuracies due to the physical nature of the measuring tool. For example, the person has to physically press or pull the different pegs, which means the reaction time measurement is hindered by the person's hand-eye coordination. Moreover, the physical mobility of the person might interfere with the person's ability to interact with the board, which would hinder the reaction time measurement.

By using VR to measure reaction time, a patient's reaction time can be measured without hindrances due to hand-eye coordination and physical mobility. Additionally, using VR to measure reaction time makes it possible to measure how a patient's reaction times change when she reacts to objects located in different portions of her visual field.

A VR system for displaying fast-moving objects in a virtual environment to measure the patient's visual reaction time includes a VR headset in electronic communication with a computing device. The VR headset is worn by the patient whose visual processing speed is being evaluated. The VR headset includes screens, eye-tracking sensors, and eye-tracking cameras. The screens are configured to display the virtual environments and virtual objects and/or optotypes that the patient views and interacts with during the evaluation. The eye-tracking sensors and eye-tracking cameras are configured to collect information about the eye movements of the patient as the patient responds to the virtual objects and/or optotypes being displayed at various positions in the virtual environment. In particular, the eye-tracking sensors and eye-tracking cameras are configured to collect data about the eye movements and reaction times of the patient. In some embodiments, the eye-tracking sensors are configured to collect the eye movement data in real-time and communicate the eye movement data to the computing device in real-time. Optionally, the eye-tracking sensors and cameras are infrared sensors and cameras.

In some embodiments, a handheld device (e.g., a controller or a VR handset) is in electronic communication with the VR headset and the computing device. The patient can use the handheld device to interact with the virtual environment displayed and the optotypes on the screens of the VR headset. For example, the patient can press a button to confirm that she is perceiving an optotype on the screen, use a controller to type in or select a brief description of the optotype, or even click on the optotype in the virtual environment.

The computing device of the VR system is configured to cause one or more virtual objects and/or optotypes to be displayed at various positions in a virtual environment. In some embodiments, the characteristics (e.g., brightness, contrast, size, color, shape, etc.) of the virtual objects and/or optotypes, the speeds at which the virtual objects and/or optotypes move through the virtual environment, the characteristics (e.g., brightness, contrast, saturation, amount of movement, type of scenery, etc.) of the virtual environment, etc. are determined by an algorithm. For example, the algorithm might increase the speed at which optotypes move across the virtual environment if the patient has an exceptional reaction time to test the outer limits of the patient's reaction time. Optionally, the algorithm might position the virtual objects and optotypes in the upper right corner of the patient's field of vision if the algorithm recognizes that she has a longer reaction time in that area. This would help the VR system gather more information about the patient's problem areas, which could help identify the reasons for the longer reaction time. This might make it possible to train the patient to improve her reaction time in her problem areas.

The computing device is also configured to receive the eye movement data from the VR headset and inputs from the handheld device. Upon receipt of the data and the inputs, the computing device processes the data and the inputs to identify the visual processing speed of the patient. In some embodiments, an algorithm processes the eye movement data and the inputs to identify the visual processing speed of the patient. Optionally, the algorithm compares the patient's visual processing speed to a database of visual processing speeds from individuals in different careers to determine whether the patient has an adequate visual processing speed for her field of work. In some embodiments, the computing device generates a report summarizing the patient's visual processing speed patterns and suggests exercises or lifestyle changes for improving visual processing speeds. This report can be accessed by a physician, the patient, or the patient's caretaker at a user interface in the computing device.

To begin the visual processing speed evaluation, the patient dons the VR headset. The computing device causes a virtual environment to be displayed on the screens of the VR headset. The VR headset (in particular, the sensors and cameras of the VR headset) identifies an initial position of the patient's eyes within the virtual environment. Next, the computing device causes an optotype to be displayed at a first position in the virtual environment. In some embodiments, multiple optotypes are displayed at or around the first position in the virtual environment. In other embodiments, one or more objects are displayed at the first position in the virtual environment.

There are multiple ways in which the optotype can be displayed in the virtual environment. In one embodiment, the optotype instantly appears in the virtual environment. In another embodiment, the optotype fades into the virtual environment.

In some embodiments, the computing device changes the characteristics of the optotype at one or more times during the evaluation. Optionally, the computing device continuously changes the characteristics of the optotype during the evaluation. The characteristics of the optotype include one or more of a shape, size, color, brightness, or contrast of the optotype.

When the optotype is displayed at the first position, the VR headset tracks a first movement of the patient's eyes as the patient's eye or eyes move from the initial position to the first position while trying to locate the optotype. In some embodiments, the VR headset tracks the first movement in real-time as the patient tries to locate the optotype. Optionally, the VR headset prompts the patient to locate the optotype (e.g., with visual or audio cues).

The VR headset tracks the first movement of the patient's eyes and shares information about the first movement with the computing device. The computing device processes the first movement information to calculate a first reaction time of the patient. The computing device can calculate the first reaction time of the patient because the computing device knows the time at which the optotype appeared in the virtual environment at the first position and knows the time at which the patient's eyes reached the first position and located the optotype. In some embodiments, the first reaction time is the amount of time taken by the patient's eyes to move from the initial position to the first position. In other embodiments, the first reaction time is the time at which the patient's eyes reach the first position.

Once the patient's eyes reach the first position, the computing device causes the optotype to be removed from the first position. In some embodiments, removing the optotype comprises instantly removing the optotype from the virtual environment. In other embodiments, removing the optotype comprises fading the optotype out of the virtual environment.

Next, the computing device causes the optotype to be displayed at a second position in the virtual environment. The second position is different from the first position. In some embodiments, the second position is closer to the edges of the patient's field of vision than the first position. Incrementally broadening the portions of the field of vision in which the optotype is displayed can help gather data about the outer limits of the patient's eye movement and visual processing speed capabilities. Broadening the field of vision used for the evaluation is most useful when paired with one or more optotypes fading in and out of the virtual environment.

In some embodiments, the frequency at which the optotype is displayed in the virtual environment can be changed. For example, there might be a 5 second gap between the time when the optotype is removed from the first position and the time when the optotype is displayed at the second position. This gap can be lengthened to accommodate a patient with a long reaction time. Similarly, this gap can be shortened to challenge a patient with a short reaction time. Challenging a patient with a short reaction time can be beneficial for identifying the outer limits of the patient's reaction time. Identifying the absolute limits of a patient's reaction time can be beneficial for people pursuing high intensity or dangerous careers (e.g., professional athletes or police officers).

In other embodiments, the optotype remains in the virtual environment and travels from the first position to the second position. Optionally, the optotype moves continuously from the first position, through the second position, and to a third position. Optionally, the optotype pauses briefly at each of the first, second, and third positions. The pauses can be any length of time. In some embodiments, the pauses are 5 seconds long. In other embodiments, the pauses are 1 second long. Optionally, the pauses are less than 1 second long. Shorter pauses correlate with a more challenging evaluation, which facilitates the collection of data about the outer limits of the patient's visual processing speed.

In some embodiments, where the optotype travels between the different positions instead of being displayed and removed from the virtual environment, the computing device changes the speed at which the optotype travels through the virtual environment between the various positions. For example, the speed at which the optotype travels between the different positions can be decreased if the patient is struggling to keep up with the movement of the optotype. It is also possible to increase the speed at which the optotype travels between the different positions to challenge a patient who is easily keeping up with the optotype as it travels across the virtual environment. Incrementally increasing the speed at which the optotype travels can be used to evaluate the outer limits of the patient's visual processing speed. Testing the outer limit and identifying the absolute limit is useful if the patient is pursuing a high intensity or dangerous career.

Optionally, where the optotype travels between the different positions instead of being displayed and removed from the virtual environment, the computing device changes the trajectory of the optotype's path as the optotype travels through the virtual environment between the various positions. For example, the optotype might leave the first position with a northwestern trajectory and leave the second position with a southern trajectory. This forces the patient to move her eyes at different angles, which facilitates the collection of a comprehensive eye movement dataset. With this information, the computing device can identify variations in the patient's visual processing speeds (and other visual processing capabilities) at different eye movement angles. Identifying variations can lead to identifying weak spots, which is crucial if the patient works in a high intensity or dangerous career where her visual processing capabilities must be operating at top capacity at all times.

In some embodiments, where the optotype travels between the different positions instead of being displayed and removed from the virtual environment, the optotype travels through the virtual environment along a randomized path. That is, instead of a smooth, predictable path, the optotype might travel in an irregular or unpredictable manner. Using a randomized path facilitates a more accurate visual processing speed evaluation as compared to using a smooth, repetitive, or otherwise predictable path because with a randomized path, the patient cannot predict the path of the optotype and use that to her advantage.

When the optotype is transported or travels from the first position to the second position, the VR headset tracks a second movement of the patient's eyes as the patient's eye or eyes move from the first position to the second position while trying to locate the optotype. In some embodiments, the VR headset (specifically, the sensors and cameras of the VR headset) tracks the second movement in real-time as the patient tries to locate the optotype.

The VR headset tracks the second movement of the patient's eyes and shares information about the second movement with the computing device. The computing device processes the second movement information to calculate a second reaction time of the patient. The computing device can calculate the second reaction time of the patient because the computing device knows the time at which the optotype appeared in the virtual environment at the second position and knows the time at which the patient's eyes reached the second position and located the optotype. In some embodiments, the second reaction time is the amount of time taken by the patient's eyes to move from the first position to the second position. In other embodiments, the second reaction time is the time at which the patient's eyes reach the second position.

In some embodiments, the VR method for assessing visual processing speed also includes calculating the speed at which the patient's eye or eyes move between the different positions of the optotype (i.e., between the initial position and the first position, between the first position and the second position, between the second position and a third position, etc.). Optionally, where the optotype travels between the different positions instead of being displayed and removed from the virtual environment, the VR method includes calculating the speed at which the patient's eyes follow the optotype. This can be used to calculate the how much slower the patient's eye or eyes move as compared to the optotype because the computing device knows the speed of the optotype. Optionally, the computing device calculates the speed of the patient's eye movements in real-time as the patient tries to locate or follow the optotype.

Optionally, the VR system can receive inputs from the patient that confirm or deny whether the patient is actually perceiving the optotype at any given position. The input can comprise verbal confirmations received at a microphone of the VR headset or tactile confirmations (e.g., pressing a button) received at a handheld device in electronic communication with the VR headset and the computing device, which would also test the patient's hand-eye coordination. Optionally, the computing device processes these inputs to identify the amount of time taken by the patient to provide the input, which is another means by which the computing device measures the patient's reaction time.

When the computing device receives the first and second movement information from the VR headset, the computing device processes the first and second movement information. This can include comparing the first and/or second movement information with a database of visual processing profiles from individuals in different careers to determine whether the patient has an adequate visual processing capabilities for her field of work. In some embodiments, this comparison occurs in real-time as the patient visually follows the optotype around the virtual environment.

Similarly, when the computing device calculates the first and second reaction times, the computing device processes the first and second reaction times. This can include comparing the first and/or second reaction times with a database of reaction times (or visual processing speeds) from individuals in different careers to determine whether the patient has an adequate visual processing speed for her field of work. In some embodiments, this comparison occurs in real-time as the computing device calculates the reaction times. Optionally, the computing device determines whether the patient satisfies the visual processing requirements for her field of work.

Optionally, the method includes generating a report that summarizes the patient's visual processing patterns and suggests exercises or lifestyle changes for improving visual processing speeds.

Assessing Eye Coordination Through Eye-Tracking Exercises

Each of a person's eyes perceives a somewhat different variation of the environment in front of the person. The brain receives both variations and fuses them together so that the person views the environment in three dimensions. The person's ability to properly see the world around him is dependent on this fusion and, thus, on the coordination between his eyes. If the person cannot properly fuse the variations (or images) perceived by each of his eyes, then he will likely see the world in double vision.

Traditionally, a physician asks a patient to look at an object in the room. When the patient looks at the object, the physician observes the patient's eyes to determine whether the patient's eyes are moving together. The physician might also ask the patient what he sees to confirm that the patient can properly fuse the two images perceived by each of his eyes. However, the comprehensiveness of this evaluation is very limited because the physician can only conduct this evaluation with a small and finite number of static objects in the room. Moreover, this evaluation is inaccurate because it is reliant on subjective observations from the physician.

By using a VR system, a comprehensive and accurate assessment of the patient's eye coordination can be performed. Not only can a VR system collect data about the patient's eye coordination with respect to objects positioned in various portions of the patient's field of vision to evaluate the effectiveness of the patient's fusing abilities at different parts of the patient's field of vision, but the VR system can also collect data bout the patient's eye coordination with respect to dynamic objects to evaluate the degree to which the patient can maintain fusion as the eye or eyes move. Moreover, with a VR system, it is possible to quantify the movements of each of the patient's eyes and calculate the coordination between the eyes.

A VR system for assessing eye coordination includes a VR headset in electronic communication with a computing device. The VR headset is worn by the patient whose eye coordination is being evaluated. The VR headset includes screens, eye-tracking sensors, and eye-tracking cameras. The screens are configured to display the virtual environments and virtual objects and/or optotypes that the patient views and interacts with during the evaluation. The eye-tracking sensors and eye-tracking cameras are configured to collect information about the eye movements of the patient as the patient responds to the virtual objects and/or optotypes being displayed at various positions in the virtual environment. In particular, the eye-tracking sensors and eye-tracking cameras are configured to collect data about the angle of eye movement, the speed of eye movement, reaction times, and fusing ability. In some embodiments, the eye-tracking sensors are configured to collect the eye movement data in real-time and communicate the eye movement data to the computing device in real-time. Optionally, the eye-tracking sensors and cameras are infrared sensors and cameras.

In some embodiments, a handheld device (e.g., a controller or a VR handset) is in electronic communication with the VR headset and the computing device. The patient can use the handheld device to interact with the virtual environment displayed and the optotypes on the screens of the VR headset. For example, the patient can press a button to confirm that she is perceiving an optotype on the screen, use a controller to type in or select a brief description of the optotype, or even click on the optotype in the virtual environment.

The computing device of the VR system is configured to cause one or more virtual objects and/or optotypes to be displayed at various positions in a virtual environment. In some embodiments, the characteristics (e.g., brightness, contrast, size, color, shape, etc.) of the virtual objects and/or optotypes, the speeds at which the virtual objects and/or optotypes move through the virtual environment, the characteristics (e.g., brightness, contrast, saturation, amount of movement, type of scenery, etc.) of the virtual environment, etc. are determined by an algorithm.

The computing device is also configured to receive the eye movement data from the VR headset and inputs from the handheld device. Upon receipt of the data and the inputs, the computing device processes the data and the inputs to evaluate the eye coordination of the patient. In some embodiments, an algorithm processes the eye movement data and the inputs to identify patterns in the patient's eye coordination that might be indicative of future misalignment issues. In some embodiments, the computing device generates a report with information about the patient's eye coordination capabilities and suggests exercises or lifestyle changes for improving eye coordination. The report can also suggest treatment or further ocular examinations. This report can be accessed by a physician, the patient, or the patient's caretaker at a user interface in the computing device.

To begin the visual processing speed evaluation, the patient dons the VR headset. The computing device causes a virtual environment to be displayed on the screens of the VR headset. The VR headset (in particular, the sensors and cameras of the VR headset) identifies an initial position of the patient's eyes within the virtual environment. Next, the computing device causes an object to be displayed at a first position in the virtual environment.

In some embodiments, multiple objects are displayed so that the patient must track multiple objects at once, which engages different eye muscles as compared to when the patient only tracks one object. For instance, when the patient tracks one object, he primarily uses his maculae. However, when the patient tries to track multiple objects, the patient must force his eyes to use other areas of the retinas in addition to the maculae. As a result, the VR method facilitates assessment of the fusing ability of lesser-used areas of the retinas. In some embodiments, multiple objects are displayed at or around the first position in the virtual environment. In other embodiments, multiple objects are displayed simultaneously at a variety of positions in the virtual environment.

Optionally, the computing device changes the characteristics of the optotype at one or more times during the evaluation. Optionally, the computing device continuously changes the characteristics of the optotype during the evaluation. The characteristics of the optotype include one or more of a shape, size, color, brightness, or contrast of the optotype.

As the object is displayed in the first position, the VR headset (in particular, the sensors and cameras of the VR headset) tracks the patient's eyes as the patient's eye or eyes move from their initial position to the first position of the object. This can be referred to as the first eye movement. Specifically, the VR headset tracks the individual movements of each of the patient's eyes. These can be referred to as the first right eye movement and the first left eye movement. In some embodiments, the VR headset continuously tracks the movements of the patient's eyes. In other embodiments, the VR headset tracks the movements of the patient's eyes in real-time as the patient moves his eyes from the initial position to the first position.

The VR headset shares the first eye movement information of each of the patient's eyes with the computing device, and the computing device processes the first eye movement information to determine a first coordination between the patient's right and left eyes. For example, the eye movement information might suggest that the right and/or left eyes move together but ultimately land on different gaze points (which is demonstrated in FIG. 12C, where the gaze position 1206A of the right eye has a deviation angle 1208A from the target gaze position 1204 while the gaze position 1206B of the left eye has a deviation angle 1208B from the target gaze position 1204, with 1208A being smaller than 1208B). Another possibility is that the right and left eyes do not move together but manage to land on the same gaze point. This would be problematic as the objects that the patient has to track increase in speed. In some embodiments, the computing device processes the eye movement information and determines the coordination between the eyes in real-time as the patient tracks the object.

Next, the computing device causes the optotype to be displayed at a second position in the virtual environment. The second position is different from the first position. The object travels through the virtual environment from the first position to the second position. In some embodiments, the object travels along a straight path. In other embodiments, the object travels along a smooth or curved path. Optionally, the object travels along a jagged, incongruent path. Optionally, the object travels along a randomized path. Displaying the object as it travels along a path with a trajectory that is difficult to predict (e.g., a jagged or randomized path) facilitates a more accurate eye coordination evaluation as compared to using a smooth, repetitive, or otherwise predictable path because with a randomized path, the patient cannot predict the path of the object and use that to his advantage. Specifically, displaying the object as it travels along an unpredictable path at least doubles the accuracy of the eye coordination evaluation.

Optionally, the computing device changes the speed at which the object travels through the virtual environment between the various positions. For example, the speed at which the object travels between the different positions can be decreased if the patient is struggling to keep up with the movement of the object. It is also possible to increase the speed at which the object travels between the different positions to challenge a patient who is easily keeping up with the object as it travels across the virtual environment. Incrementally increasing the speed at which the object travels can be used to evaluate the outer limits of the patient's eye coordination capabilities. Testing the outer limit and identifying the absolute limit is useful if the patient is pursuing a high intensity or dangerous career.

In other embodiments, the second position is closer to the edges of the patient's field of vision than the first position. Incrementally broadening the portions of the field of vision in which the optotype is displayed can help gather data about the outer limits of the patient's eye coordination capabilities.

In some embodiments, when the first coordination is compared to a specific threshold. The threshold can be an average or healthy eye coordination. The threshold can also be a required level of eye coordination for the patient's field of work. When the first coordination is below a specific threshold, the object is displayed at a second position that is near the first position. This serves the purpose of gathering more data so that the computing device or the physician can determine why the patient's eye coordination is inadequate near the first position. A similar repetitive display can be used when the patient's eye coordination fails to meet the threshold when the object moves at a certain speed or if the patient's eye coordination fails to meet the threshold when the object has a certain appearance. In other embodiments, focusing the evaluation near the first position to gather more information about the patient's eye coordination near the first position can also include displaying the object away from the first position and then near the first position so that the patient's eyes must constantly move around while ultimately returning to the area near the first position.

The VR headset can track the movement of one or both the patient's right and/or left eyes as the patient's eye or eyes move from the first position to the second position. This can be referred to as the second eye movement or the second right eye movement and the second left eye movement. In some embodiments, the VR headset continuously tracks the movements of the patient's eyes. In other embodiments, the VR headset tracks the movements of the patient's eyes in real-time as the patient moves his eyes from the first position to the second position.

The VR headset shares the second eye movement information of each of the patient's eyes with the computing device, and the computing device processes the second eye movement information to determine a second coordination between the patient's right and left eyes-akin to the first coordination described above. In some embodiments, the computing device processes the eye movement information and determines the second coordination between the eyes in real-time as the patient tracks the object.

In some embodiments, the method includes quantifying deviation angles of the left and right eyes (in accordance with the method described above with respect to FIGS. 12A-12C) when the patient is viewing the object at the first and second positions. In other embodiments, the method also includes calculating an amount of deviation reduction between the patient's right and left eyes, which is the difference in the deviation angle between the patient's right and left eyes.

Optionally, the VR system can receive inputs from the patient that confirm or deny whether the patient is actually perceiving the object at any given position in the virtual environment. The input can comprise verbal confirmations received at a microphone of the VR headset or tactile confirmations (e.g., pressing a button) received at a hand-held device in electronic communication with the VR headset and the computing device, which would also test the patient's hand-eye coordination. In some embodiments, the input comprises the patient's interaction with the virtual environment. Some examples of this interactions might include translating or rotating the object, changing the color or size of the object, etc. The VR system might prompt the patient to, for example, rotate the object to make it face forward every time it stops moving. As a result, the VR system collects data about the patient's hand-eye coordination to evaluate along with the eye coordination data.

When the computing device receives some or all of the aforementioned data (i.e., the first and second eye movements, the first and second eye coordination, the deviation angles, the deviation reduction, the inputs, the hand-eye coordination information, etc.), the computing device processes this data by comparing it to a database of eye movement, eye coordination, deviation angle, deviation reduction, hand-eye coordination, etc. from individuals with known eye coordination capabilities. Through this comparison, the computing device determines whether there are any abnormalities in the patient's eye coordination. These abnormalities can be indicative of conditions such as nystagmus, strabismus, amblyopia, etc. In some embodiments, this comparison occurs in real-time as the VR headset collects the data from the patient.

Optionally, the method includes generating a report that summarizes the patient's eye coordination patterns and suggests treatment and further medical evaluations, as necessary. In some embodiments, the method includes indicating whether the patient satisfies eye coordination requirements for his field of work.

Testing Motion Sensitivity Using Virtual Scenes

Motion sensitivity refers to symptoms, most commonly dizziness and nausea, that are provoked by visual stimulation. There are two primary types of visual stimulation that provoke motion sensitivity: asymmetrical optic flow and impaired vestibular inputs. Optic flow refers to a flow of visual motion, such as when a person walks quickly through a stationary environment. As the person walks, objects in the right side of her peripheral vision appear to move to the right, while objects in the left side of her peripheral vision appear to move to the left. Typically, these two sensations cancel each other out and the person hardly notices them. However, when the optic flow is asymmetrical, the right side appears to move to the right, but the left side does not appear to move (or vice versa), which results in the sensation that the stationary environment is rotating. This sensation of rotation can induce dizziness and nausea in the person.

Ordinarily, a person can distinguish the sensation of moving through her environment from the sensation of her environment moving around her because her brain knows when she is moving. However, when the person's vestibular inputs are impaired, her brain cannot effectively make this distinction. As a result, both moving through and environment and standing in an environment that is moving around her will cause the person to experience a swaying sensation while her brain tries to make the distinction. This leads to dizziness and/or nausea in the person.

Asymmetrical optic flow and impaired vestibular inputs are most commonly a result of vestibular disorders. Typically, vestibular disorders can only be detected through physical exams and/or neurological exams, which are very general. As a result, a physician might take a long time conducting physical and neurological exams before diagnosing a patient with a vestibular disorder. Using a VR system, the patient's motion sensitivity can be evaluated, which can lead to a quicker and more accurate vestibular disorder diagnosis.

A VR system for testing motion sensitivity includes a VR headset in electronic communication with a computing device. The VR headset is worn by the patient whose motion sensitivity is being evaluated. The VR headset includes screens, eye-tracking sensors, and eye-tracking cameras. The screens are configured to display the virtual scene that the patient views and interacts with during the evaluation. The eye-tracking sensors and eye-tracking cameras are configured to collect information about the motion sensitivity of the patient as the patient responds to the movement of the virtual scene. In particular, the eye-tracking sensors and eye-tracking cameras are configured to track the eye movements and reaction times of the patient. In some embodiments, the eye-tracking sensors are configured to collect information about the eye movements and reaction times in real-time and communicate that information to the computing device in real-time. Optionally, the eye-tracking sensors and cameras are infrared sensors and cameras.

In some embodiments, one or more handheld devices (e.g., a controller or a VR handset) are in electronic communication with the VR headset and the computing device. The patient can use the handheld device to interact with the virtual scene displayed on the screens of the VR headset and to otherwise respond to the evaluation. For example, the patient can press a button or click on the object to confirm that she is feeling nauseous, indicate a level of motion sickness on a scale, or type in a description of her current motion sensitivity (e.g., dizzy and nauseous, dizzy only, etc.).

In other embodiments, one or more microphones are in electronic communication with the VR headset and the computing device. The microphones are configured to pick up verbal input from the patient. For example, the patient can verbally describe the degree of motion sickness that she is experiencing in response to various virtual scenes (e.g., "mostly dizzy and a little nauseous"; "the cityscape scene with people walking by makes me feel nauseous, but watching the water flow by in the river is fine"; etc.).

The computing device of the VR system is configured to cause a variety of virtual scenes to be displayed on the screens of the VR headset. In some embodiments, the type of virtual scene and the characteristics (e.g., brightness, contrast, pixel direction, speed of movement, type of movement, direction of movement, etc.) of the virtual scene are determined by an algorithm. Optionally, the type and characteristics of the virtual scene are changed in real-time by the algorithm based on the patient's input (e.g., her level of motion sensitivity). For example, if the patient is feeling too sick to engage with the evaluation, the algorithm can decrease amount of movement in the virtual scene to make the patient feel more comfortable. Similarly, if the patient feels completely fine, the algorithm can change the type of movement in the scene to identify what type of motion makes the patient feel motion sick.

The computing device is also configured to receive the motion sensitivity information from the VR headset as well as inputs from the handheld devices and the microphones. Upon receipt of the information and the inputs, the computing device processes the data and the inputs to determine what type of motion triggers the patient's motion sensitivity and the extent to which the patient experiences motion sensitivity. In some embodiments, an algorithm processes the eye movement data and the inputs to determine what type of motion triggers the patient's motion sensitivity and to what extent the patient experiences motion sensitivity. In some embodiments, the computing device generates a report with information about the patient's motion sensitivity patterns, suggestions for situations to be cautious about, or recommendations for further medical evaluations (especially if the patient shows signs of vestibular disorders). This report can be accessed by a physician, the patient, or the patient's caretaker at a user interface in the computing device.

In a preferred embodiment, the VR method for evaluating motion sensitivity includes showing the patient a virtual scene on the screens of the VR headset. Showing the patient the virtual scene largely serves two purposes: (1) testing the patient's ability to perceive an object within the virtual scene to ensure that the patient is engaged and focused on the virtual scene and (2) instigating a reaction from the patient to collect information about the patient's motion sensitivity.

To begin the motion sensitivity evaluation, the patient dons the VR headset. The computing device causes a virtual scene to be displayed on the screens of the VR headset. The virtual scene comprises a collection of continuously moving elements. There are a multitude of ways to display continuously moving elements in a virtual scene. For example, the scene might be of a forest or a nature hike, and the continuously moving elements are tree leaves swaying in a breeze or wildlife walking by (such as the scene 1400 shown in FIG. 14A, described in greater detail below). The scene might also show a body of water, and the continuously moving elements are waves in the ocean or a current of a river. Another example of a virtual scene is a city sidewalk with people walking by or cars driving by (such as the scene 1450 shown in FIG. 14B, described in greater detail below). Other virtual scenes are also possible.

The VR system prompts the patient to provide an input. The input can include the patient's description of the virtual scene, so that the patient can confirm that she is perceiving all the motion in the virtual scene. The input can also include the patient's description of the type and degree of motion sickness she is experiencing in response to the virtual scene.

For example, the input might inform the computing device that when the patient perceives a virtual scene with a lot of motion on her right side and slow movements on her left side, she experiences mild dizziness and no nausea. Another patient's input might inform that computing device that when the patient perceives a virtual scene with elements that move away from her she experiences nausea, but when she perceives a virtual scene with elements that move towards her, she experiences neither dizziness nor nausea. Other combinations are also possible.

In some embodiments, the patient can interact with objects in the scene and/or walk through the scene. Optionally, the VR system prompts the patient to navigate through the virtual scene. Optionally, the VR system prompts the patient to find objects in the virtual scene. Optionally, the VR system prompts the patient to touch or grab objects in the virtual scene.

In some embodiments, the computing device changes the virtual scene. The computing device can change the virtual scene to adjust the type of motion being displayed (e.g., objects in the environment moving as opposed to the environment itself moving as opposed to the patient walking through a stationary environment). The computing device can also change the virtual scene to adjust the direction of the motion or the speed of the motion. The computing device can also change the virtual scene to adjust the size of the continuously moving objects. For example, the virtual scene might originally display small objects moving throughout the environment (e.g., balls bouncing past the patient) and be adjusted to display large objects moving through the environment (e.g., horses running past the patient). Other adjustments to the virtual scene are also possible.

Optionally, when the computing device changes the virtual scene, the VR system prompts the patient to provide an additional input, akin to the input described above.

Optionally, the computing device causes one or more objects and/or optotypes to be displayed in the virtual scene. For example, a bug 1402 or a rat 1404 might be displayed in the forest scene 1400 of FIG. 14A. In another example, a bus stop 1452, flag 1454, or optotype 1456 might be displayed in the city scene 1450 of FIG. 14B. The computing device can prompt the patient to locate and/or interact with the objects and/or optotypes to evaluate the patient's saccadic movements and the patient's motion sensitivity response to performing saccadic movements. In some embodiments, the patient can use a VR handset to click on the optotypes. In other embodiments, the patient can simply look at the optotypes, and the computing device will be able to identify whether the patient is looking at the optotypes by comparing the coordinates of the optotypes with the eye position data received by the sensors and cameras.

Optionally, the objects and/or optotypes are moving through the virtual scene. Optionally, the objects and/or optotypes move rapidly through the virtual scene, which makes the objects and/or optotypes more difficult for the patient to track. The rapid motion can also affect the type and degree of motion sickness experienced by the patient. The computing device can prompt the patient to track, locate, and/or interact with the moving objects and/or optotypes to evaluate the patient's smooth pursuit eye movements and the patient's motion sensitivity response to performing smooth pursuit eye movements. In some embodiments, the patient can use a VR handset to click on the objects and/or optotypes. In other embodiments, the patient can follow the objects and/or optotypes with her eyes, and the computing device will be able to identify whether the patient is looking at the optotypes by comparing the coordinates of the optotypes with the eye position data received by the sensors and cameras.

In some embodiments, where there are objects and/or optotypes in the virtual scene (static or dynamic), the computing device calculates an accuracy with which the patient locates or tracks the objects and/or optotypes (i.e., the accuracy of the patient's eye movements and eye-tracking).

In some embodiments, where there are objects and/or optotypes in the virtual scene (static or dynamic), the computing device prompts the patient to provide an input relating to how her motion sensitivity changes in response to the objects and/or optotypes. This input is similar to the input described above.

The computing device receives the various types of input (e.g., motion sensitivity, eye-tracking, eye movement, etc.) from the VR headset (as well as the handheld devices and the microphones, where applicable) and processes the input. The computing device processes the input to identify patterns in the patient's motion sensitivity to determine the types and degrees of motion that trigger different types and degrees of motion sensitivity in the patient. The computing device can also identify patterns in the patient's eye-tracking and eye movement capabilities (e.g., eye-tracking becomes less effective when the patient is in fast-paced environments, eye movement becomes less accurate when the patient is dizzy but is unchanged when the patient is nauseous, etc.) In some embodiments, the computing device processes the input in real-time as the patient provides the input to the VR headset.

When the computing device receives the aforementioned input, the computing device can further process this input by comparing it to a database of motion sensitivity data from individuals with known motion sensitivity statuses. Through this comparison, the computing device determines whether there are any abnormalities in the patient's motion sensitivity, which can be indicative of visual or neurological conditions such as vestibular disorders and impaired motor perception. In some embodiments, this comparison occurs in real-time as the VR headset collects the input from the patient.

Optionally, the method includes generating a report that summarizes the motion sensitivity information and suggests treatment and further medical evaluations, as necessary.

Evaluating Spatial Awareness Through Motion Tracking and Vision Testing

The motion of a person's head is supposed to be coordinated with the motion of her eyes, and discrepancies between head movements and eye movements can negatively affect the person's vision. The vestibulo-ocular reflex helps stabilize vision by synchronizing the person's eye movements with her head movements. For example, if the person turns her head to the left, the vestibulo-ocular reflex is supposed to move the person's eyes to the right to cancel out the head motion and stabilize the person's vision. An abnormal or unhealthy vestibulo-ocular reflex might delay the compensatory eye movement, overcompensate the eye movement, undercompensate the eye movement, etc. As a result, the person might not fuse images properly, which results in double vision. The person might also have increased reaction times or decreased visual acuity due to discrepancies between her head and eye movements.

These discrepancies can be a result of ocular disorders. For example, the person's eye muscles might have been improperly formed, the person might have strabismus, the person might have misaligned eyes due to phorias or tropias, etc. The discrepancies can also be a result of injured neck muscles or improper bone structure impacting the person's ability to move her head. Using a VR system equipped to track a patient's motion and vision, it is possible to evaluate the patient's spatial awareness, which can help identify whether the patient's vision is impacted by a discrepancy between her head and eye movements and what ocular disorders or other physical ailments cause that discrepancy.

A VR system for evaluating spatial awareness includes a VR headset in electronic communication with a computing device. The VR headset is worn by the patient whose spatial awareness is being evaluated and is configured to collect spatial awareness input from the patient.

The VR headset includes screens, eye-tracking sensors, eye-tracking cameras, and motion-tracking sensors. The screens are configured to display a virtual environment (which can include objects, optotypes, and obstacles) that the patient views and interacts with during the evaluation.

The eye-tracking sensors and eye-tracking cameras are configured to track the patient's gaze direction and visual responses (e.g., blink rates, pupil dilation, etc.) as the patient responds to the virtual environment. In some embodiments, the eye-tracking sensors are configured to track the patient's gaze direction and visual responses in real-time (i.e., as the patient responds to and interacts with the virtual environment) and communicate that information to the computing device in real-time. Optionally, the eye-tracking sensors and cameras are infrared sensors and cameras.

The motion-tracking sensors are configured to track physical movements and a spatial orientation of the patient. The motion-tracking sensors are further configured to track a three-dimensional movement of the head of the patient to identify the translation, pitch, yaw, and roll of the patient's head as she shifts around and participates in the VR evaluation. In some embodiments, the motion-tracking sensors are configured to track physical movements, spatial orientation, and three-dimensional movement in real-time and communicate the corresponding data to the computing device in real-time. Optionally, the motion-tracking sensors are configured to track a speed at which the patient moves her head in different directions. Optionally, the motion-tracking sensors comprise accelerometers and/or gyroscopes. The positions of the motion-tracking sensors on the VR headset are depicted in FIG. 13.

Figure 13:
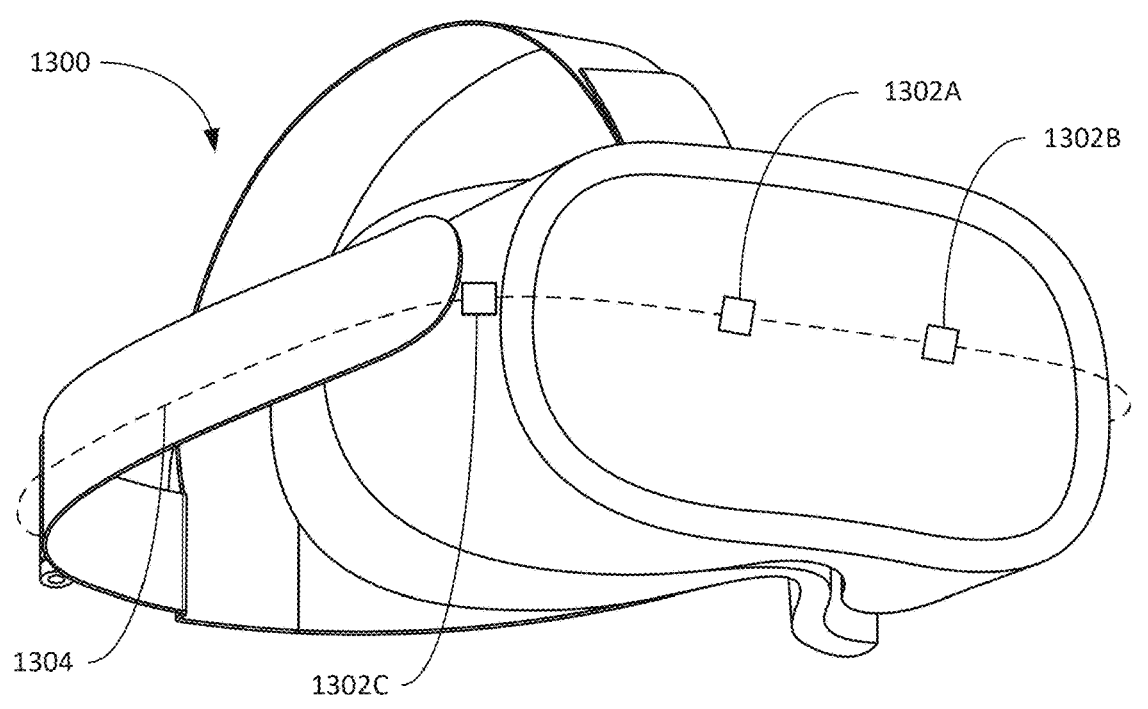
FIG. 13 illustrates a placement of motion-tracking sensors on a VR headset, in accordance with some embodiments.
Figure 13:
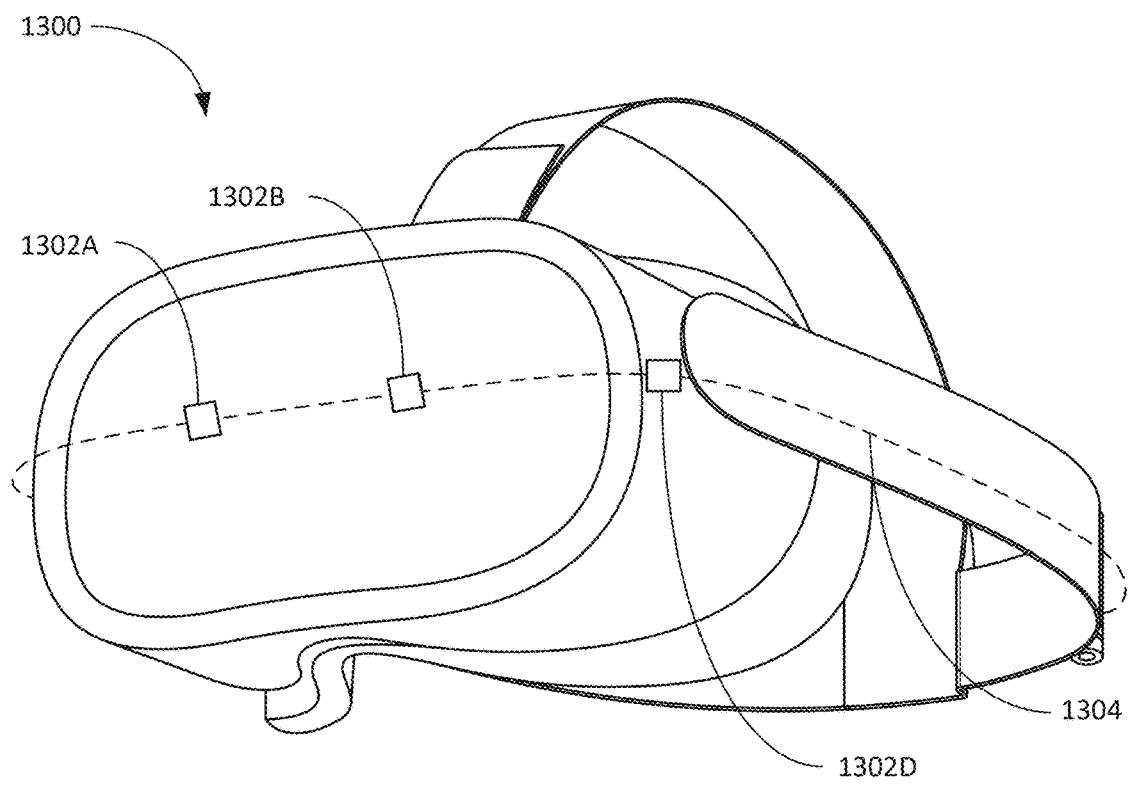

FIG. 13 illustrates a placement of motion-tracking sensors on a VR headset, in accordance with some embodiments. FIG. 13 shows two perspective views of a VR headset 1300 with motion-tracking sensors 1302 (1302A, 1302B, 1302C, and 1302D). Each VR headset 1300 has at least four motion-tracking sensors 1302, with at least two motion-tracking sensors 1302A, 1302B being placed on a front portion of the VR headset 1300, at least one motion-tracking sensor 1302C being placed on a right portion of the VR headset 1300, and at least one motion-tracking sensor 1302D being placed on a left portion of the VR headset 1300. The front portion is the portion of the VR headset 1300 that would be in front of the patient's eyes, the right portion would be near the patient's right ear, and the left portion would be near the patient's left ear. In some embodiments, the motion-tracking sensors 1302 are on the outer exterior of the VR headset 1300 (on the surface of the VR headset 1300 that is away from the patient's face), on the inner exterior of the VR headset 1300 (on the surface of the VR headset 1300 that is adjacent to or in contact with the patient's face), or on the interior of the VR headset 1300. In some embodiments, the placement of the motion-tracking sensors 1302 is asymmetrical around the patient's head.

In some embodiments, the motion-tracking sensors 1302 are positioned along a transverse plane of the VR headset 1300. The transverse plane aligns with the eyeline of the patient when the patient dons the VR headset 1300 and is indicated by dashed line 1304 in FIG. 13.

In some embodiments, one or more handheld devices (e.g., a controller or a VR handset) are in electronic communication with the VR headset and the computing device. The patient can use the handheld device to interact with the virtual environment displayed on the screens of the VR headset and to otherwise respond to the evaluation. For example, the patient can press a button or click on the object to confirm that she has located the object or select the clearing she wants to go through to avoid obstacles.

In some embodiments, the eye-tracking sensors, eye-tracking cameras, motion-tracking sensors, and handheld devices are configured to detect reaction times from the patient that are 500 milliseconds or less. In other embodiments, the eye-tracking sensors, eye-tracking cameras, motion-tracking sensors, and handheld devices are configured to detect reaction times from the patient that are 250 milliseconds or less. the eye-tracking sensors, eye-tracking cameras, motion-tracking sensors, and handheld devices are configured to detect reaction times from the patient that are 100 milliseconds or less.

The computing device of the VR system is configured to cause a virtual environment and virtual tasks to be displayed on the screens of the VR headset. In some embodiments, an algorithm in the computing device determines the characteristics of the virtual environment and the virtual tasks (e.g., brightness, contrast, saturation, characteristic of the objects and/or obstacles, speed at which patient is navigated through environment, etc.) and how those characteristics are changed throughout the duration of the evaluation. Optionally, the characteristics of the virtual environment and the virtual tasks are changed in real-time by the algorithm based on the patient's spatial awareness input.

The computing device is also configured to receive the spatial awareness input from the VR headset as well as inputs from the handheld devices and the microphones. Upon receipt of the inputs, the computing device processes the inputs to evaluate discrepancies between the patient's head movements and eye movements. Optionally, an algorithm processes the data to measure the accuracy of the patient's spatial awareness, spatial orientation, and reaction time. In some embodiments, an algorithm processes the spatial awareness input to suggest ocular disorders and other physical ailments that might cause the discrepancies between the patient's head and eye movements. In some embodiments, the computing device generates a report with information about the patient's head and eye movement discrepancies, suggestions for treatment (e.g., a glasses prescription), or recommendations for further medical evaluations. This report can be accessed by a physician, the patient, or the patient's caretaker at a user interface in the computing device.

There are several VR methods for evaluating a patient's spatial awareness: navigating the patient through a virtual scene, navigating the patient through a virtual obstacle course, and prompting the patient to identify an object from different perspectives.

Evaluating Spatial Awareness by Navigating Through a Virtual Scene

This method begins when the patient dons the VR headset. The computing device causes a virtual environment to be displayed on the screens of the VR headset, such as the virtual environments shown in FIGS. 14A-14B, described in greater detail below.

Figure 14A:
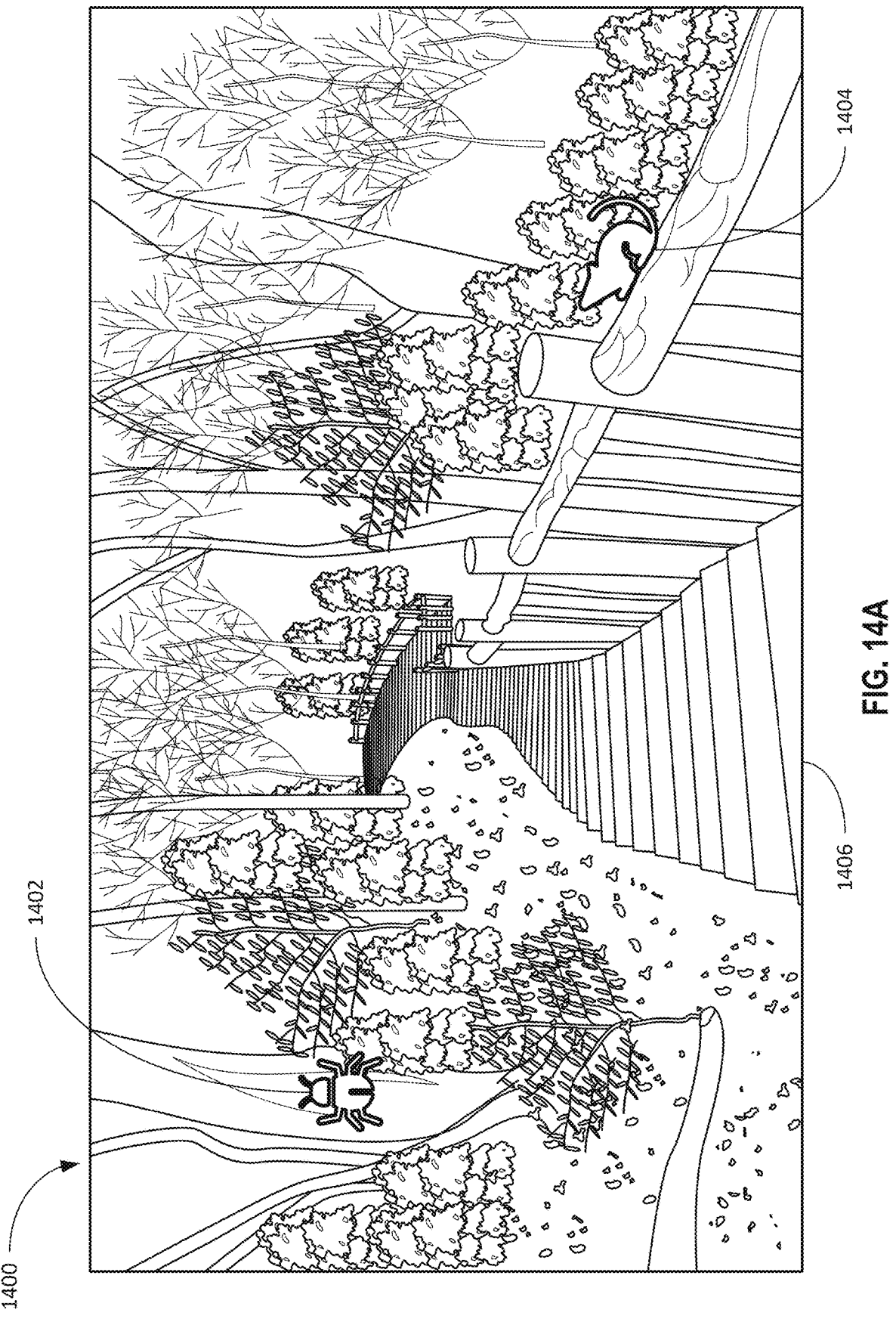
FIG. 14A illustrates a virtual forest with a path along which a patient is navigated to evaluate the patient's spatial awareness, in accordance with some embodiments.
Figure 14B:
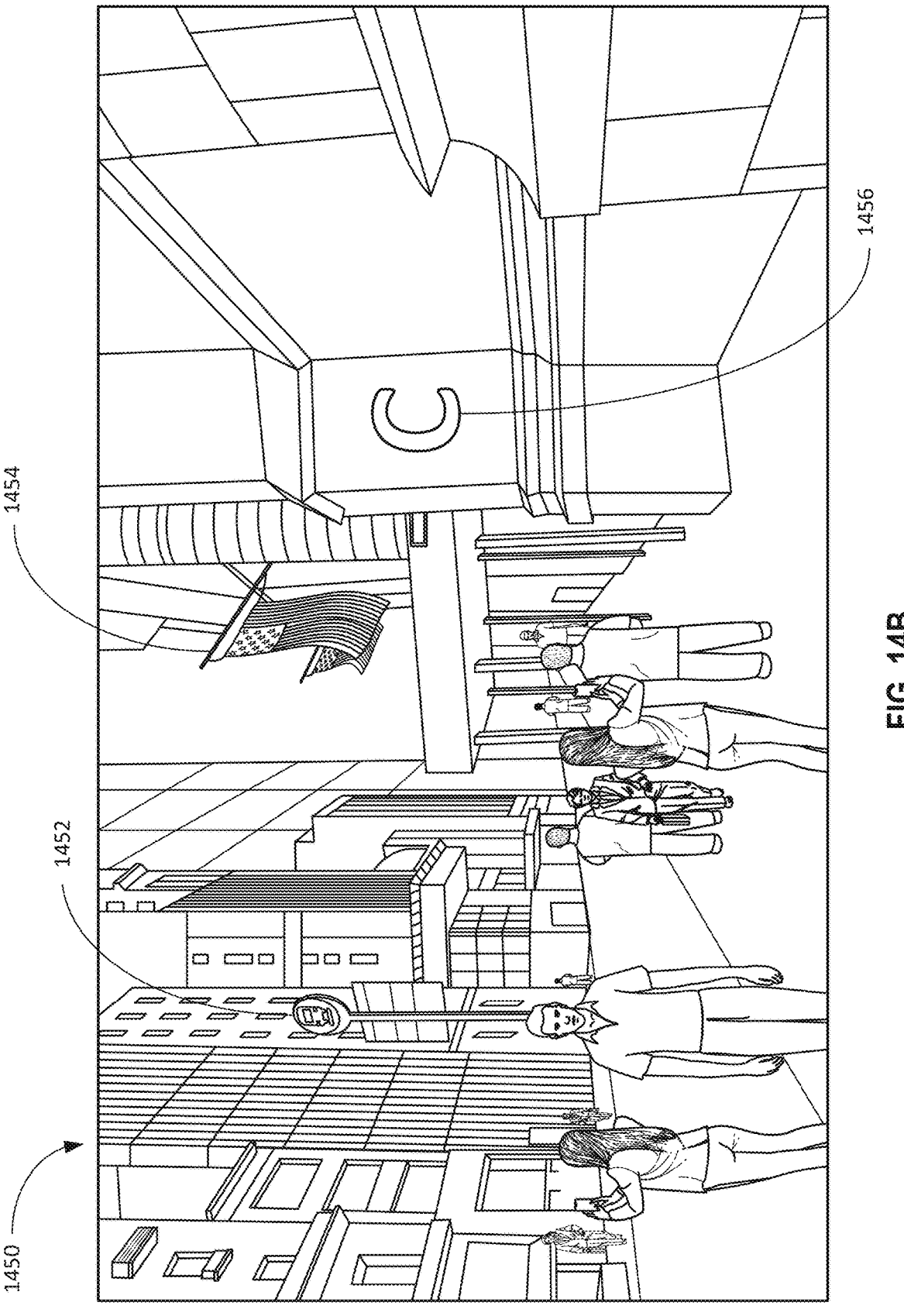
FIG. 14B illustrates a virtual city with a crowd through which the patient is navigated to evaluate the patient's spatial awareness, in accordance with some embodiments.

FIG. 14A illustrates a virtual forest with a path along which a patient is navigated to evaluate the patient's spatial awareness, in accordance with some embodiments. FIG. 14A shows a virtual scene 1400 of a forest with a path 1406. In a forest, larger elements like trees tend to stay still while smaller details like leaves tend to move, so this type of environment is useful for assessing the patient's spatial awareness when faced with minute movements. FIG. 14B illustrates a virtual city with a crowd through which the patient is navigated to evaluate the patient's spatial awareness, in accordance with some embodiments. FIG. 14B shows a virtual scene 1450 of a city with various people walking around. In a city, larger elements like people and cars tend to move in a variety of directions at a variety of speeds, so this type of environment is useful for evaluating the patient's spatial awareness when faced with larger movements.

In some embodiments, a virtual maze is displayed on the screens of the VR headset, and the patient is navigated through the virtual maze past various objects and/or optotypes.

As the patient is led down the path, the virtual environment changes around her in real-time. For example, in FIG. 14A, the trees and objects in the forest change around the patient as she is led down the path 1406. Similarly, as the patient is led down the street in FIG. 14B, the view of the buildings and people around the patient change in coordination with her walking.

During the evaluation, the patient is led down the path at a speed and direction set by the computing device. In some embodiments, the speed and direction tailored to the patient based on the patient's baseline spatial awareness (i.e., based on what is known about the patient's spatial awareness capabilities before the evaluation) and the patient's progress throughout the evaluation. In other embodiments, the direction of the path and the speed at which the patient is led down the path changes throughout the evaluation. Optionally, the changes to the direction of the path and the speed at which the patient is led down the path is tailored to the patient based on the patient's baseline spatial awareness and the patient's progress throughout the evaluation. For example, the path might become more winding, or the speed might increase if the patient is doing well. This would challenge the patient and facilitate the evaluation of the outer limits of her ability to spatially orient herself and identify surrounding objects.

The virtual environment includes one or more objects and/or optotypes that the patient must locate while she is navigated through the virtual environment. For example, in FIG. 14A, the virtual environment 1400 includes a bug 1402 and a rat 1404. As the patient is led down the path 1406, she must locate the bug 1402 and the rat 1404 before she passes them. To accomplish this goal, the patient must turn her head and move her eyes to look around her. Similarly, in FIG. 14B, the virtual environment 1450 includes a bus stop 1452, a flag 1454, and an optotype 1456. The patient cannot control the direction at which she walks through the virtual environment 1450, but she must locate the bus stop 1452, the flag 1454, and the optotype 1456 as she weaves through the crowd. In some embodiments, the computing device changes the speed and/or the direction at which the patient is led through the virtual environment based on the effectiveness with which she identifies objects and/or optotypes. This assesses the patient's spatial awareness: her ability to recognize her surroundings (what her surroundings look like, how far away she is from different objects, etc.) as she moves through an environment. This also assess the patient's ability to scan her surroundings and focus in on an object as her surroundings move.

While the patient attempts to locate the objects and/or optotypes, the VR headset is receiving inputs from the patient. The eye-tracking sensors and eye-tracking cameras track the gaze direction and visual responses of the patient. In some embodiments, the eye-tracking sensors and eye-tracking cameras continuously monitor the gaze direction and visual responses. The motion-tracking sensors track the head movements and spatial orientation of the patient. In some embodiments, the motion-tracking sensors continuously monitor the head movements and spatial orientation. Optionally, the handheld device is receiving inputs as the patient uses the handheld device to point at or click on objects and/or optotypes.

In some embodiments, the computing device calculates an accuracy with which the patient locates the objects and/or optotypes, which is suggestive of the patient's eye movement accuracy. Optionally, the computing device calculates this locating accuracy in real-time as the patient locates the objects and/or optotypes. Optionally, the computing device determines that the patient accurately located an object and/or optotype if the patient's gaze position is within 2° of the target gaze position (i.e., the position of the object and/or optotype).

In some embodiments, the computing device calculates a reaction time of the patient. This reaction time might be the time between when an object appeared in the environment and the patient located the object. This reaction time can also be the time between when the patient was prompted to locate the object and when the patient located the object.

Evaluating Spatial Awareness by Navigating a Virtual Obstacle Course

The VR method for evaluating spatial awareness by navigating the patient through a virtual obstacle course requires the patient to observe both the central and peripheral areas of her field of vision (i.e., the patient must scan her entire field of vision) to observe the obstacles. To navigate the obstacle course, the patient must identify clearings in the environment, which requires that she can home in on a small area immediately after scanning a large area.

This method begins when the patient dons the VR headset. The computing device causes a virtual environment to be displayed on the screens of the VR headset, such as the virtual environments shown in FIGS. 15A-15B, described in greater detail below. The virtual environments include obstacles that the patient must avoid and clearings that the patient must walk through. The patient is navigated through the virtual environment at a speed set by the computing device, which means that the patient must avoid the obstacles and find the clearings at a pace set by the computing device. As described above with respect to the previous method, the pace can change to increase or decrease the difficulty of the obstacle course. Optionally, this difficulty level is tailored to the patient. The computing device forces the patient to continuously move in a generally forward direction, but the patient can move from side to side to avoid the obstacles and enter the clearings. In some embodiments, the computing device leads the patient down a winding path, and the patient must avoid obstacles along the winding path.

Figure 15A:
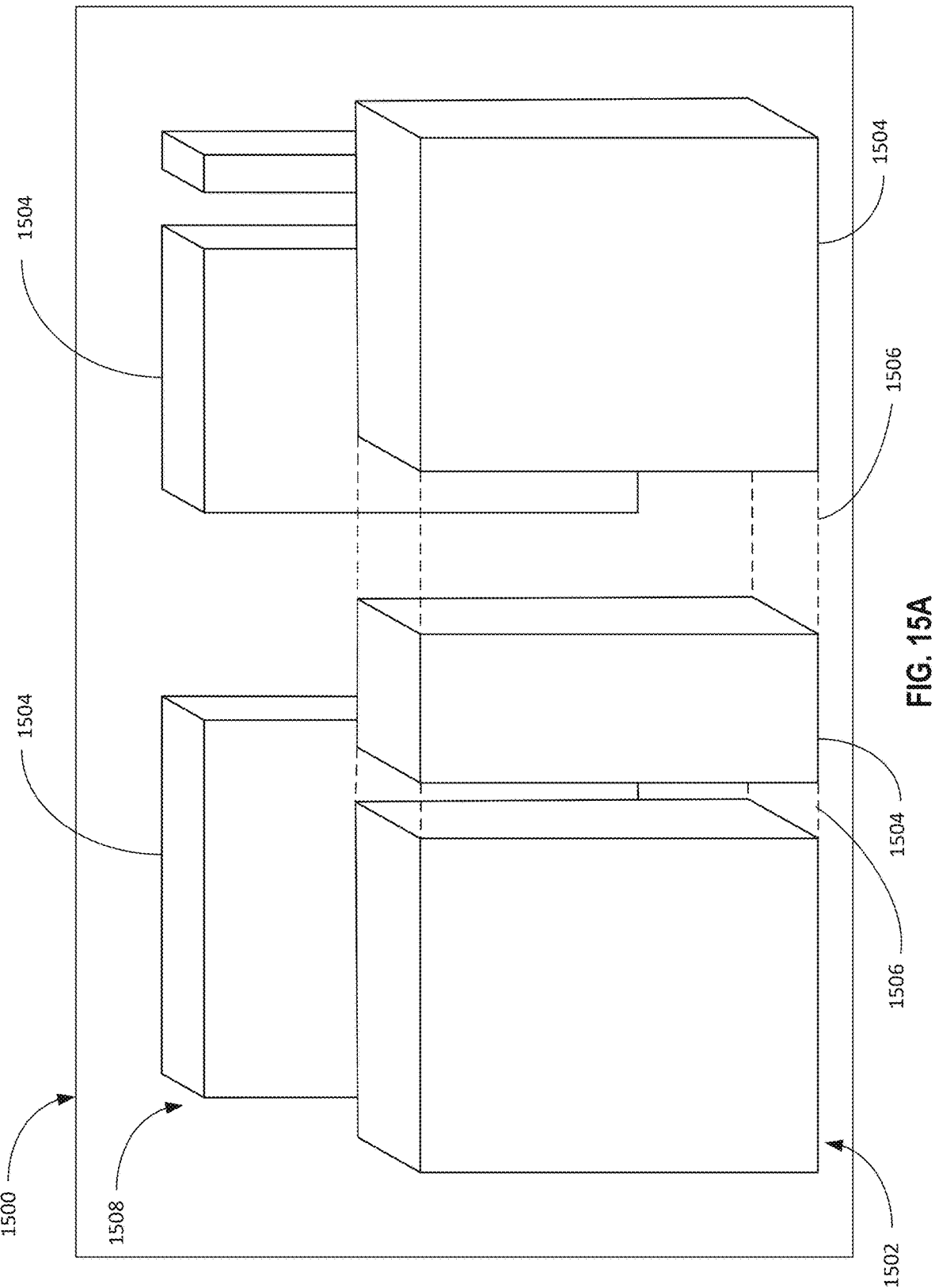
FIG. 15A illustrates a virtual obstacle course for evaluating the patient's spatial awareness, in accordance with some embodiments.

FIG. 15A illustrates a virtual obstacle course for evaluating the patient's spatial awareness, in accordance with some embodiments. The virtual environment 1500 includes a first row 1502 of obstacles 1504 and clearings 1506 and a second row 1508 of obstacles 1504 and clearings 1506. The patient is led towards the first row 1502 at a speed decided by the computing device and must avoid the obstacles 1504 and locate the clearings 1506 so that the patient can walk through one of the clearings 1506 to reach the second row 1504.

The size of the clearings 1506 can change (likewise, the size of the obstacles 1504 can change) throughout the evaluation. In some embodiments, the size of the clearings 1506 is dependent on how successfully the patient is navigating through the obstacle course. For example, if the patient is doing well, the clearings 1506 might decrease in size, which would make them harder to locate. This would challenge the patient and facilitate evaluation of the outer limits of the patient's scanning and focusing abilities, which are related to her ability to spatially orient herself in an environment. In some embodiments, the obstacles 1504 and the clearings 1506 are shaped such that the patient must jump or duck to avoid the obstacles 1504.

Figure 15B:
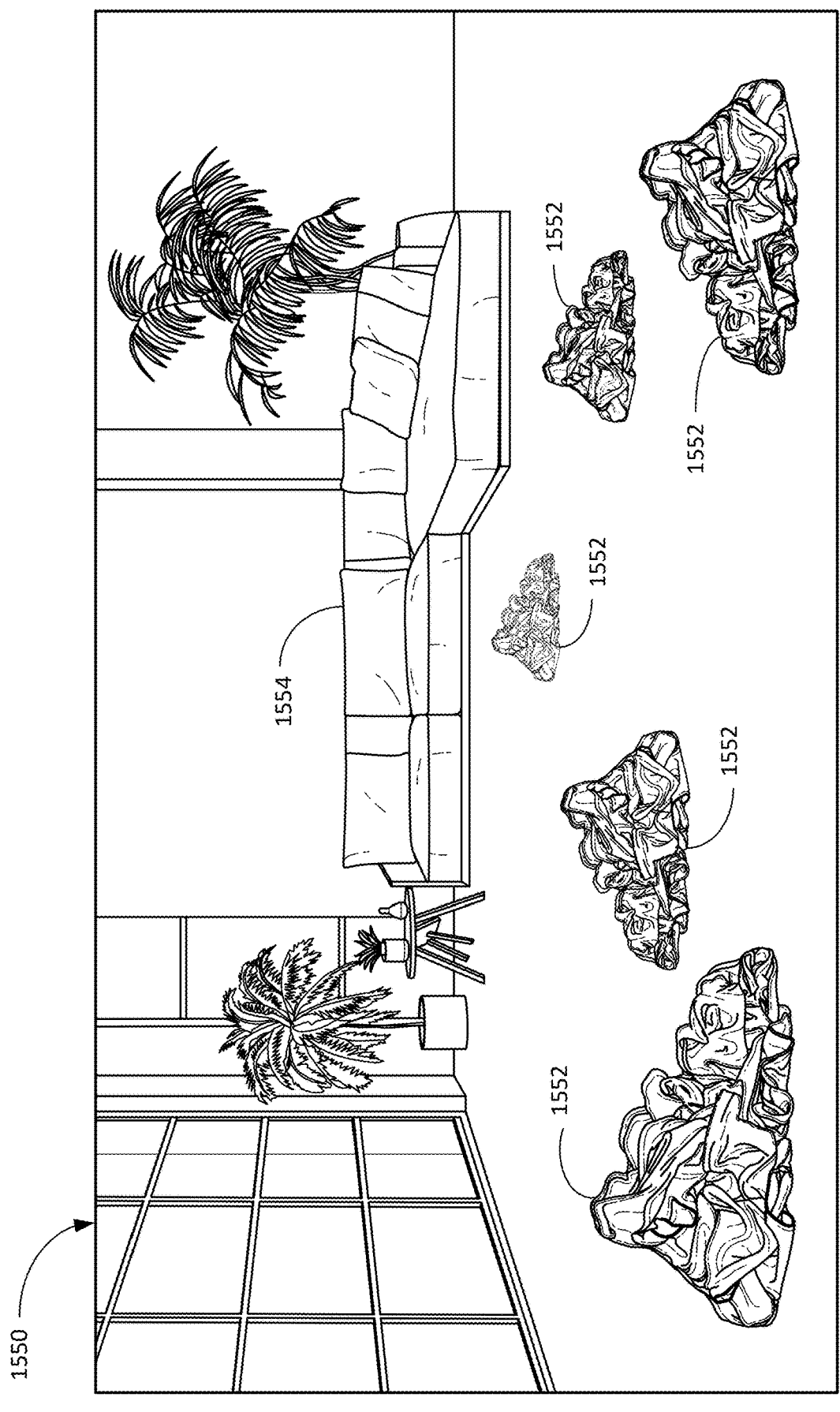
FIG. 15B illustrates a virtual living room that serves as an obstacle course for evaluating the patient's spatial awareness, in accordance with some embodiments.

FIG. 15B illustrates a virtual living room that serves as an obstacle course for evaluating the patient's spatial awareness, in accordance with some embodiments. The virtual environment 1550 depicts a living room with obstacles 1552 in the form of piles of laundry. The patient is led towards the couch 1554 in the back of the living room 1550 at a speed decided by the computing device and must avoid the obstacles 1552 by walking in the spaces between the piles of laundry (i.e., the clearings).

The number and size of the piles can change throughout the evaluation. In some embodiments, additional types of obstacles can be added to the virtual environment 1550 (e.g., static obstacles such as pieces of furniture or dynamic obstacles such as pets roaming around the living room). As described above with respect to FIG. 15A, these adjustments to the obstacle course are dependent on how successfully the patient is locating the clearings and avoiding the obstacles.

While the patient attempts to navigate the obstacle course, the VR headset is receiving inputs from the patient. The eye-tracking sensors and eye-tracking cameras track the gaze direction and visual responses of the patient as she scans the virtual environment to identify obstacles and clearings. In some embodiments, the eye-tracking sensors and eye-tracking cameras continuously monitor the gaze direction and visual responses. The motion-tracking sensors track the head movements and spatial orientation of the patient. In some embodiments, the motion-tracking sensors continuously monitor the head movements and spatial orientation. Optionally, the handheld device is receiving inputs as the patient uses the handheld device to point at or click on clearings that she wants to walk through.

In some embodiments, the computing device calculates an accuracy with which the patient avoids obstacles, which is suggestive of the patient's eye movement accuracy. Similarly, the computing device can calculate an accuracy with which the patient identifies clearings. Optionally, the computing device calculates this locating accuracy in real-time as the patient navigates the obstacle course.

In some embodiments, the computing device calculates a reaction time of the patient. For example, with respect to FIG. 15A, the reaction time might be the time between when the patient enters the first row 1502 and when she locates one of the clearings 1506. The reaction time can also be the time between when a new obstacle appears in the virtual environment (e.g., with respect to FIG. 15B, when a pet roams into the living room) and when the patient locates the new obstacle.

Evaluating Spatial Awareness by Identifying an Object from Different Perspectives The VR method for evaluating spatial awareness by prompting a patient to identify an object from different perspectives requires that the patient broadly observe her environment to pinpoint and zero in on a specific item in the environment.

This method begins when the patient dons the VR headset. The computing device causes a virtual environment to be displayed on the screens of the VR headset. The computing device also causes an object to be displayed in the virtual environment. The object is displayed such that the patient views it from a first perspective.

The patient must identify the object from the first perspective. This can include identifying the orientation and/or perspective of the object as well as distinguishing the object from other aspects of the virtual environment. The VR headset receives a first input from the patient while the patient identifies the object from the first perspective. The first input includes the patient's description of the object and the identification of the object from the first perspective. The first input can also include one or more of head movements of the patient, a spatial orientation of the patient in the virtual environment, a gaze direction of the patient, or visual responses of the patient. The eye-tracking sensors and eye-tracking cameras track the gaze direction and visual responses of the patient as she scans the virtual environment to identify object from the first perspective. In some embodiments, the eye-tracking sensors and eye-tracking cameras continuously monitor the gaze direction and visual responses. The motion-tracking sensors track the head movements and spatial orientation of the patient. In some embodiments, the motion-tracking sensors continuously monitor the head movements and spatial orientation. Optionally, the handheld device is receiving inputs as the patient uses the handheld device to point at or click on the object.

The patient is then navigated around the virtual environment to view and identify the object from a second perspective. In some embodiments, the object is in the same position. In other embodiments, the object is in a different position.

The patient is navigated around the virtual environment at a speed determined by the computing device, which means that the patient must identify the various perspectives of the object at a pace determined by the computing device. As described above with respect to the previous method, the pace can change to challenge or accommodate the patient. Optionally, this difficulty level is tailored to the patient's performance throughout the evaluation.

The VR headset receives a second input from the patient while the patient identifies the object from the second perspective. The second input includes the patient's description of the object and the identification of the object from the second perspective. The second input can also include one or more of head movements of the patient, a spatial orientation of the patient in the virtual environment, a gaze direction of the patient, or visual responses of the patient. The eye-tracking sensors and eye-tracking cameras track the gaze direction and visual responses of the patient as she scans the virtual environment to identify object from the second perspective. In some embodiments, the eye-tracking sensors and eye-tracking cameras continuously monitor the gaze direction and visual responses. The motion-tracking sensors track the head movements and spatial orientation of the patient. In some embodiments, the motion-tracking sensors continuously monitor the head movements and spatial orientation. Optionally, the handheld device is receiving inputs as the patient uses the handheld device to point at or click on the object.

In some embodiments, the evaluation is conducted with different objects or different variations of the same object. The nature, shape, size, color, brightness, and contrast of the object can all be changed throughout the evaluation.

In other embodiments, the computing device calculates an accuracy with which the patient properly identifies the object from the different perspectives, which is suggestive of the patient's spatial awareness. Optionally, the computing device calculates this accuracy in real-time as the patient is navigated through the virtual environment and looks for the object.

In some embodiments, the computing device calculates a reaction time of the patient. The reaction time can refer to the time between when the object appears in patient's field of vision and when the patient properly identifies the perspective from which she is viewing the object. The reaction time can also refer to the time between when the patient is prompted to describe the orientation of the object (e.g., verbally, by clicking on an option, etc.) and when the patient successfully describes the orientation of the object.

Assessing Eye-Tracking Stability and Effectiveness Using Gaze-Contingent Displays Each person has a natural sway to his or her body. While some people can stand very still, others cannot. This shifting or swaying of the body influences eye-tracking effectiveness and stability. Eye-tracking effectiveness refers to a person's ability to view something and quickly fuse the images perceived by each of his eyes into a single, three-dimensional image. Eye-tracking stability refers to a person's ability to hold onto a fused image after initially forming the fused image. People with a greater tendency to shift or sway tend to have worse eye-tracking effectiveness and stability. Evaluating a person's eye-tracking effectiveness and stability while he is sitting and standing provides information about the extent to which his natural sway impacts his vision. This information is useful because a person with a larger sway that negatively impacts his vision can adjust his eye movements to compensate for his sway.

A VR system for assessing eye-tracking stability and effectiveness includes a VR headset in electronic communication with a computing device. The VR headset is worn by the patient whose eye-tracking stability and effectiveness are being evaluated and is configured to collect eye tracking data from the patient.

The VR headset includes screens, eye-tracking sensors, eye-tracking cameras, and motion-tracking sensors. The screens are configured to display one or more objects, optotypes, patterns, and shapes in a virtual environment that the patient views and interacts with during the evaluation.

The eye-tracking sensors and eye-tracking cameras are configured to measure one or more of an angle of eye movements of the patient, a delay in the eye movements of the patient, and a reaction time of the patient as the patient responds to the virtual environment. In some embodiments, the eye-tracking sensors are configured to take these measurements (i.e., as the patient responds to and interacts with the virtual environment) and communicate that information to the computing device in real-time. Optionally, the eye-tracking sensors and cameras are infrared sensors and cameras.

The motion-tracking sensors are configured to track physical movements and a spatial orientation of the patient. The motion-tracking sensors are further configured to track a three-dimensional movement of the head of the patient to identify the translation, pitch, yaw, and roll of the patient's head as she shifts around and participates in the VR evaluation. In some embodiments, the motion-tracking sensors are configured to track physical movements, spatial orientation, and three-dimensional movement in real-time and communicate the corresponding data to the computing device in real-time. Optionally, the motion-tracking sensors are configured to track a speed at which the patient moves her head in different directions. Optionally, the motion-tracking sensors comprise accelerometers and/or gyroscopes. The positions of the motion-tracking sensors on the VR headset are depicted in FIG. 13.

As shown in FIG. 13, each VR headset 1300 has at least four motion-tracking sensors 1302, with at least two motion-tracking sensors 1302A, 1302B being placed on a front portion of the VR headset 1300, at least one motion-tracking sensor 1302C being placed on a right portion of the VR headset 1300, and at least one motion-tracking sensor 1302D being placed on a left portion of the VR headset 1300. In some embodiments, the motion-tracking sensors 1302 are positioned along a transverse plane of the VR headset 1300. The positioning of the motion-tracking sensors 1302 is described in greater detail above with respect to FIG. 13 and the method for evaluating spatial awareness.

In some embodiments, one or more handheld devices (e.g., a controller or a VR handset) are in electronic communication with the VR headset and the computing device. The patient can use the handheld device to interact with the virtual environment displayed on the screens of the VR headset and to otherwise respond to the evaluation. For example, the patient can press a button or click on the object to confirm that she has located a target in the virtual environment.

The computing device of the VR system is configured to cause the visual exercise to be displayed in a virtual environment on the screens of the VR headset. In some embodiments, an algorithm in the computing device determines the characteristics (e.g., brightness, contrast, saturation) of the environment and how those characteristics are changed throughout the duration of the assessment. Optionally, the characteristics of the virtual environment and the virtual tasks are changed in real-time by the algorithm based on the patient's eye tracking data.

The computing device is also configured to receive the eye tracking data from the VR headset as well as inputs from one or more handheld devices. Upon receipt of the data and inputs, the computing device processes the data and inputs to evaluate patient's fixation stability, saccadic latency, and tracking accuracy. Optionally, an algorithm processes the data to evaluate patient's fixation stability, saccadic latency, and tracking accuracy. In some embodiments, the computing device generates a report with information about the differences between the evaluation results when the patient was sitting and when the patient was standing, suggestions for therapy or eye training, or recommendations for further medical evaluations. This report can be accessed by a physician, the patient, or the patient's caretaker at a user interface in the computing device.

The method for assessing and improving eye-tracking stability and effectiveness begins when the patient dons the VR headset. The patient participates in the assessment and the training in both the sitting and standing positions, so the VR headset can gather eye tracking data while the patient is sitting and standing, and the computing device can compare the two sets of eye tracking data. The computing device causes a virtual environment to be displayed on the screens of the VR headset. The virtual environment includes a shape or an object, and a first pattern is displayed on the shape or object. In some embodiments, the first pattern is a grid pattern, such as the one displayed in FIG. 16A. Other patterns are also possible (e.g., stripes, dots, animal prints, triangles, etc.).

FIGS. 16A-16C illustrate a shape with variations of a grid pattern which can be used to assess and improve the patient's eye-tracking stability and effectiveness, in accordance with some embodiments. The shape 1600 includes a grid pattern with squares 1602 of a first size and lines 1604 with a first thickness.

The patient observes the first pattern displayed on the shape or object, and the VR headset (specifically, the eye-tracking sensors and the eye-tracking cameras) monitor the patient's eye movements—referred to as the first eye movements. In some embodiments, the shape or object moves around the virtual environment. In other embodiments, the pattern moves within the shape or object. Optionally, the VR headset continuously monitors the patient's eye movements as the patient observes the moving shape, object, or pattern.

The VR headset communicates the first eye movement data to the computing device, and the computing device processes this data to evaluate the patient's eye-tracking stability and effectiveness. In some embodiments, the computing device processes the data in real-time as the patient observes the first pattern.

Based on the patient's eye-tracking stability and effectiveness upon observance of the first pattern, the computing device adjusts the shape or object in the virtual environment. This can include changing the first pattern into a second pattern. Examples of this adjustment are shown in FIGS. 16B and 16C. In some embodiments, the shape or object is adjusted in real-time as the computing device processes the eye tracking data. In other embodiments, the shape or object is adjusted in real-time as the patient observes the first pattern.

In FIG. 16B, the squares 1602 have been made smaller, but the lines 1604 are the same size. Optionally, the squares become so small that the pattern is more similar to an array of white dots than a grid of black lines. In FIG. 16C, the squares 1602 are the same size, but the lines 1604 have been made thicker. Optionally, the color or brightness of the squares 1602 and the lines 1604 can be adjusted. Optionally, the contrast between the squares 1602 and the lines 1604 can be adjusted.

As described above with respect to the first pattern, the patient observes the second pattern, and the VR headset monitors the patient's second eye movements so that it can communicate the second eye movement data with the computing device. The computing device processes this data to evaluate the patient's eye-tracking stability and effectiveness. In some embodiments, the computing device processes the data in real-time as the patient observes the second pattern.

In some embodiments, a target is placed in the center of the object or shape so that the patient must observe the various patterns while focusing on the target. In other embodiments, a target is placed in different positions on the object or shape while the pattern stays the same, as shown in FIGS. 16D-16F, which are described in greater detail below. Optionally, a target is placed in different positions on the object or shape while the pattern is adjusted throughout the evaluation.

FIGS. 16D-16F illustrate a shape with an optotype displayed in various orientations, positions, and sizes relative to a grid pattern, in accordance with some embodiments. The shape 1600 includes a grid pattern and an optotype 1606. As shown, the optotype 1606 can be placed in different positions on the shape 1600. The optotype 1606 can also change in size. For example, optotype 1606A in FIG. 16D is larger than optotype 1606B in FIG. 16E. Moreover, the optotype can be placed in different orientations, as shown by the tilted optotype 1606C in FIG. 16F. Other variations of the optotype 1606 are also possible.

The patient tracks the optotype 1606 as it moves around the shape 1600, and the VR headset monitors the patient's eye movements to determine whether the patient is accurately and quickly fusing the optotype 1606.

Optionally, the computing device analyzes the eye movement data to determine whether the patient's eye-tracking stability and effectiveness satisfy a certain threshold, which can be determined by an average capability or a minimum health requirement. If the patient's eye-tracking stability or effectiveness are below the threshold when the optotype is at a certain location, in a certain orientation, of a certain size, etc., then the computing device will continue to display the optotype in a similar location, a similar orientation, a similar size, etc. This provides more information about the patient's problem areas, which can help diagnose ocular disorders. For example, if the patient is below a threshold when it comes to focusing on a target, she might have issues with the center of her retina, which oversees foveal fixation. Repeatedly inducing this particular eye movement can give the VR headset time to collect a comprehensive dataset, which can provide information such as the amount of time it takes the center of the retina to track the target and a degree of misalignment between the patient's gaze position and the target gaze position (i.e., the angle of deviation discussed with respect to FIGS. 12B-12C, above).

In some embodiments, the method begins by occluding one of the patient's eyes. This facilitates individual assessment and training of each eye, which is valuable where the eye-tracking stability and effectiveness differs between the patient's eyes.

The computing device receives the first and second sets of eye movement data from the VR headset and processes the data to determine an eye-tracking stability and an eye-tracking effectiveness of the patient. This can include comparing some or all the data to a database of eye-tracking stabilities and effectiveness of individuals with known ocular health statuses. Through this comparison, the computing device, or an algorithm within the computing device, can identify abnormalities in the eye-tracking stability and eye-tracking effectiveness of the patient. These abnormalities can be indicative of conditions such as nystagmus, oculomotor dysfunction, and other eye movement disorders.

Optionally, the method includes generating a report that summarizes the patient's eye-tracking stability and effectiveness and suggest further medical evaluations, as necessary.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A method of evaluating eye movement, the method comprising: displaying a virtual environment on screens of a virtual reality (VR) headset worn by a patient; displaying an object in the virtual environment at a first position; monitoring a first input of the patient, wherein the first input comprises an eye movement of the patient in response to the object being displayed at the first position; displaying the object in the virtual environment at a second position, wherein the second position is different from the first position; monitoring a second input of the patient, wherein the second input comprises the eye movement of the patient in response to the object being displayed at the second position; and comparing one or more of the first and second input to a database.

Clause 2. The method of Clause 1, wherein displaying the object at the first and second positions comprises instantly showing the object in the first position, instantly removing the object from the first position, instantly the object in the second position, and instantly removing the object from the second position.

Clause 3. The method of any of the preceding Clauses, wherein displaying the object at the first and second positions comprises fading the object into the first position, fading the object out of the first position, fading the object into the second position, and fading the object out of the second position.

Clause 4. The method of any of the preceding Clauses, wherein displaying the object at the first and second positions comprises displaying the object as the object travels along a continuous path between the first and second positions.

Clause 5. The method of any of the preceding Clauses, wherein displaying the object at the first and second positions comprises incrementally adjusting a position of the object in the virtual environment.

Clause 6. The method of any of the preceding Clauses, wherein incrementally adjusting the position of the object in the virtual environment comprises: displaying the object at the first position, wherein the first position is five degrees left of a center point in the virtual environment; and displaying the object at the second position, wherein the second position is five degrees right of the center point.

Clause 7. The method of any of the preceding Clauses, wherein monitoring the first and second inputs comprises continuously monitoring the eye movements of the patient.

Clause 8. The method of any of the preceding Clauses, wherein monitoring the first and second inputs comprises identifying a delay between the object being displayed at the first and second positions and the eye movement of the patient in response to the object being displayed at the first and second positions.

Clause 9. The method of any of the preceding Clauses, wherein comparing one or more of the first and second input to the database comprises comparing one or more of the first and second input to the database in real-time as the patient responds to the object being displayed at the first and second positions.

Clause 10. The method of any of the preceding Clauses, further comprising quantifying deviation angles of the eye movements of the patient.

Clause 11. The method of any of the preceding Clauses, further comprising calculating a percent difference in the deviation angles of each eye of the patient.

Clause 12. The method of any of the preceding Clauses, further comprising recommending evaluation for eye movement disorders if the percent difference is 20% or more.

Clause 13. The method of any of the preceding Clauses, further comprising recommending evaluation for eye movement disorders if the percent difference is 25% or more.

Clause 14. The method of any of the preceding Clauses, further comprising recommending evaluation for eye movement disorders if the percent difference is 30% or more.

Clause 15. The method of any of the preceding Clauses, further comprising recommending treatment for eye movement disorders and/or further evaluation for eye movement disorders.

Clause 16. The method of any of the preceding Clauses, further comprising using one or more of the first and second inputs to generate a report that summarizes eye movement patterns and abnormalities in the eye movement patterns.

Clause 17. A system for evaluating eye movement, the system comprising: a virtual reality (VR) headset comprising at least one eye-tracking sensor and at least one eye-tracking camera, the at least one eye-tracking sensor and the at least one camera being configured to collect eye movement data of a patient wearing the VR headset; and a computing device in electronic communication with the VR headset, the computing device being configured to cause an object to be displayed at various positions in a virtual environment and process the eye movement data to identify eye movement patterns of the patient, wherein the eye movement data comprises eye movements of the patient in response to the object being displayed at various positions in the virtual environment.

Clause 18. The system of Clause 17, further comprising a handheld device in electronic communication with the VR headset and the computing device, wherein the patient can use the handheld device to provide input in response to the object being displayed at various positions in the virtual environment.

Clause 19. The system of any of Clauses 17 to 18, wherein the eye movement data collected by the at least one eye-tracking sensor and the at least one eye-tracking camera comprises one or more of an accuracy, speed, and coordination of eye movements of the patient.

Clause 20. The system of any of Clauses 17 to 19, wherein the at least one eye-tracking sensor and the at least one eye-tracking camera are configured collect the eye movement data in real-time and communicate the eye movement data with the computing device in real-time.

Clause 21. The system of any of Clauses 17 to 20, wherein the at least one eye-tracking camera is an infrared camera.

Clause 22. The system of any of Clauses 17 to 21, wherein the at least one eye-tracking camera comprises at least two eye-tracking cameras with an eye-tracking camera pointed at each pupil of the patient.

Clause 23. The system of any of Clauses 17 to 22, wherein the computing devices comprises an algorithm that compares the eye movement patterns of the patient to a database to determine whether the eye movement patterns of the patient deviate from healthy ocular motor behavior.

Clause 24. The system of any of Clauses 17 to 23, wherein the computing device comprises a user interface at which a report summarizing the eye movement patterns of the patient can be accessed.

Clause 25. A virtual reality (VR) headset for evaluating eye movement disorders, the VR headset comprising at least one eye-tracking sensor and at least one eye-tracking camera, the at least one eye-tracking sensor and the at least one camera being configured to collect eye movement data of a patient wearing the VR headset.

Clause 26. The VR headset of Clause 25, wherein the eye movement data collected by the at least one eye-tracking sensor and the at least one eye-tracking camera comprises one or more of an accuracy, speed, and coordination of eye movements of the patient.

Clause 27. The VR headset of any of Clauses 25 to 26, wherein the at least one eye-tracking sensor and the at least one eye-tracking camera are configured collect the eye movement data in real-time and communicate the eye movement data with the computing device in real-time.

Clause 28. The VR headset of any of Clauses 25 to 27, wherein the at least one eye-tracking camera is an infrared camera.

Clause 29. The VR headset of any of Clauses 25 to 28, wherein the at least one eye-tracking camera are pointed at each pupil of the patient.

Clause 30. A method for evaluating visual processing speed using moving optotypes in a virtual reality (VR) environment, the method comprising: displaying a VR environment on screens of a VR headset worn by a patient; identifying an initial position of a patient's eyes; displaying an optotype in the VR environment at a first position; tracking a first movement of the patient's eyes as the patient's eye moves from the initial position to the first position; identifying a first reaction time; removing the optotype from the first position; displaying the optotype in the VR environment at a second position; tracking a second movement of the patient's eyes as the patient's eye moves from the first position to the second position; identifying a second reaction time; and comparing one or more of the first movement, the first reaction time, the second movement, and the second reaction time to a database to evaluate the visual processing speed of the patient.

Clause 31. The method of Clause 30, wherein displaying the optotype in the VR environment comprises fading the optotype into the VR environment and removing the optotype comprise fading the optotype out of the VR environment.

Clause 32. The method of any of Clauses 30 to 31, wherein displaying the optotype in the VR environment comprises instantly displaying the optotype in the VR environment and removing the optotype comprises instantly removing the optotype from the VR environment.

Clause 33. The method of any of Clauses 30 to 32, wherein tracking the first and second movements of the patient's eyes comprises tracking the first and second movements in real-time.

Clause 34. The method of any of Clauses 30 to 33, wherein identifying the first reaction time comprises identifying an amount of time taken by the patient's eyes to move from the initial position to the first position and identifying the second reaction time comprises identifying an amount of time taken by the patient's eyes to move from the first position to the second position.

Clause 35. The method of any of Clauses 30 to 34, wherein identifying the first and second reaction times comprises identifying the time at which the patient's eyes reach the first and second positions, respectively.

Clause 36. The method of any of Clauses 30 to 35, further comprising changing one or more of a shape, size, color, brightness, or contrast of the optotype.

Clause 37. The method of any of Clauses 30 to 36, wherein the optotype is displayed at the first position at a first time and the optotype is displayed at the second position at a second time.

Clause 38. The method of any of Clauses 30 to 37, further comprising changing a number of milliseconds between the first time and the second time.

Clause 39. The method of any of Clauses 30 to 38, wherein displaying the optotype in the VR environment at the first and second positions comprises incrementally increasing a field of vision in which the optotype is displayed.

Clause 40. The method of any of Clauses 30 to 39, further comprising calculating speeds at which the patient's eye moves from the initial position to the first position and from the first position to the second position.

Clause 41. The method of any of Clauses 30 to 40, wherein calculating the speeds at which the patient's eye moves comprises calculating the speeds in real-time as the patient's eye moves.

Clause 42. The method of any of Clauses 30 to 41 wherein comparing one or more of the first movement, the first reaction time, the second movement, and the second reaction time to the database comprises comparing the first movement, the first reaction time, the second movement, and the second reaction time to the database in real-time.

Clause 43. The method of any of Clauses 30 to 42, wherein the database comprises visual processing profiles from individuals with known visual processing speeds.

Clause 44. The method of any of Clauses 30 to 43, further comprising generating a report that summarizes visual processing speed patterns of the patient and deviations in the visual processing speed patterns.

Clause 45. The method of any of Clauses 30 to 44, further comprising indicating whether the patient satisfies visual processing speed requirements for his field of work.

Clause 46. A method for evaluating visual processing speed using rapidly moving objects in a virtual reality (VR) environment, the method comprising: displaying a VR environment on screens of a VR headset worn by a patient; identifying an initial position of a patient's eyes; displaying an optotype in the VR environment at a first position; displaying the optotype in the VR environment as the optotype travels from the first position to a second position; tracking a first movement of the patient's eyes as the patient's eye moves from the first position to the second position; identifying a first reaction time; displaying the optotype in the VR environment as the optotype travels from the second position to a third position; tracking a second movement of the patient's eyes as the patient's eye moves from the second position to the third position; identifying a second reaction time; and comparing one or more of the first movement, the first reaction time, the second movement, and the second reaction time to a database to evaluate the visual processing speed of the patient.

Clause 47. The method of Clause 46, further comprising tracking an initial movement of the patient's eyes as the patient's eye moves from the initial position to the first position.

Clause 48. The method of any of Clauses 46 to 47, wherein displaying the optotype in the VR environment at the first, second, and third positions comprises displaying the optotype moving continuously along a path that includes the first, second, and third positions.

Clause 49. The method of any of Clauses 46 to 48, wherein displaying the optotype in the VR environment at the first and second positions comprises displaying the optotype moving along a path that includes the first, second, and third positions and pausing at the first, second, and third positions.

Clause 50. The method of any of Clauses 46 to 49, further comprising changing a speed at which the optotype travels.

Clause 51. The method of any of Clauses 46 to 50, wherein displaying the optotype in the VR environment at the first, second, and third positions comprises incrementally increasing a field of vision in which the optotype is displayed.

Clause 52. The method of any of Clauses 46 to 51, wherein displaying the optotype in the VR environment as the optotype travels comprises displaying the optotype traveling through the VR environment along a randomized path.

Clause 53. The method of any of Clauses 46 to 52, further comprising changing one or more of a shape, size, color, brightness, or contrast of the optotype.

Clause 54. The method of any of Clauses 46 to 53, wherein tracking the first and second movements of the patient's eyes comprises tracking the first and second movements in real-time.

Clause 55. The method of any of Clauses 46 to 54, wherein identifying the first reaction time comprises identifying an amount of time taken by the patient's eyes to move from the first position to the second position and identifying the second reaction time comprises identifying an amount of time taken by the patient's eyes to move from the second position to the third position.

Clause 56. The method of any of Clauses 46 to 55, wherein identifying the first and second reaction times comprises identifying the time at which the patient's eyes reach the second and third positions, respectively.

Clause 57. The method of any of Clauses 46 to 56, further comprising receiving a first input and a second input from the patient, wherein the first input indicates that the patient perceives the optotype at the second position and the second input indicates that the patient perceives the optotype at the third position.

Clause 58. The method of any of Clauses 46 to 57, further comprising identifying an amount of time taken by the patient to provide the first and second inputs.

Clause 59. The method of any of Clauses 46 to 58, further comprising calculating speeds at which the patient's eye moves from the first position to the second position and from the second position to the third position.

Clause 60. The method of any of Clauses 46 to 59, wherein calculating the speeds at which the patient's eye moves comprises calculating the speeds in real-time as the patient's eye moves.

Clause 61. The method of any of Clauses 46 to 60, wherein comparing one or more of the first movement, the first reaction time, the second movement, and the second reaction time to the database comprises comparing the first movement, the first reaction time, the second movement, and the second reaction time to the database in real-time.

Clause 62. The method of any of Clauses 46 to 61, wherein the database comprises visual processing profiles from individuals with known visual processing speeds.

Clause 63. The method of any of Clauses 46 to 62, further comprising generating a report that summarizes visual processing speed patterns of the patient and deviations in the visual processing speed patterns.

Clause 64. The method of any of Clauses 46 to 63, further comprising indicating whether the patient satisfies visual processing speed requirements for his field of work.

Clause 65. A system for evaluating visual processing speed, the system comprising: a virtual reality (VR) headset comprising at least one eye-tracking sensor and at least one eye-tracking camera, the at least one eye-tracking sensor and the at least one camera being configured to collect eye movement data of a patient wearing the VR headset; and a computing device in electronic communication with the VR headset, the computing device being configured to cause an optotype to be displayed at different positions throughout a virtual environment and process the eye movement data to identify the visual processing speed of the patient, wherein the eye movement data comprises eye movements of the patient in response to the optotype being displayed at different positions in the virtual environment.

Clause 66. The system of Clause 65, further comprising a handheld device in electronic communication with the VR headset and the computing device, wherein the patient can use the handheld device to provide input in response to the object being displayed at various positions in the virtual environment.

Clause 67. The system of any of Clauses 65 to 66, wherein the eye movement data collected by the at least one eye-tracking sensor and the at least one eye-tracking camera comprises eye movements and/or reaction times of the patient.

Clause 68. The system of any of Clauses 65 to 67, wherein the at least one eye-tracking sensor and the at least one eye-tracking camera are configured collect the eye movement data in real-time and communicate the eye movement data with the computing device in real-time.

Clause 69. The system of any of Clauses 65 to 68, wherein the at least one eye-tracking camera is an infrared camera.

Clause 70. The system of any of Clauses 65 to 69, wherein the computing device comprises a user interface at which a report summarizing the eye movement patterns of the patient can be accessed.

Clause 71. A method for assessing eye coordination, the method comprising: displaying a virtual environment on screens of a virtual reality (VR) headset worn by a patient; identifying an initial position of a patient's eyes; displaying an object in the virtual environment at a first position; tracking L1 and R1 as the patient's eye moves from the initial position to the first position, wherein L1 is a first eye movement of a patient's left eye and R1 is a first eye movement of a patient's right eye; processing L1 and R1 to determine a first coordination between the patient's left eye and the patient's right eye; displaying the object in the virtual environment at a second position; tracking L2 and R2 as the patient's eye moves from the first position to the second position, wherein L2 is a second eye movement of the patient's left eye and R2 is a second eye movement of the patient's right eye; processing L2 and R2 to determine a second coordination between the patient's left eye and the patient's right eye; and comparing one or more of the first coordination and the second coordination to a database to evaluate the eye coordination of the patient.

Clause 72. The method of Clause 71, wherein displaying the object in the virtual environment comprises displaying multiple objects in the virtual environment.

Clause 73. The method of any of Clauses 71 to 72, further comprising changing one or more of a nature, shape, size, color, brightness, or contrast of the object.

Clause 74. The method of any of Clauses 71 to 73, wherein displaying the object in the virtual environment at the first and second positions comprises displaying the object traveling through the virtual environment from the first position to the second position along a randomized path.

Clause 75. The method of any of Clauses 71 to 74, wherein displaying the object in the virtual environment at the first and second positions comprises incrementally increasing a field of vision in which the object is displayed.

Clause 76. The method of any of Clauses 71 to 75, wherein tracking L1, R1, L2, and R2 comprises tracking L1, R1, L2, and R2 in real-time.

Clause 77. The method of Clause 71, wherein processing L1, R1, L2, and R2 to determine the first and second coordination comprises processing L1, R1, L2, and R2 in real-time to determine the first and second coordination in real-time.

Clause 78. The method of any of Clauses 71 to 76, further comprising, when the first coordination is below a threshold, displaying the object at multiple areas near the first position and, when the second coordination is below the threshold, displaying the object at multiple areas near the second position.

Clause 79. The method of any of Clauses 71 to 78, further comprising quantifying deviation angles of L1, R1, L2, and R2.

Clause 80. The method of any of Clauses 71 to 79, further comprising calculating a percent difference in the deviation angles of the patient's left eye and the patient's right eye.

Clause 81. The method of any of Clauses 71 to 80, further comprising receiving a first input and a second input from the patient, wherein the first input comprises an interaction with the object at the first position and the second input comprises the interaction with the object at the second position.

Clause 82. The method of any of Clauses 71 to 81, comparing one or more of the first coordination and the second coordination to the database comprises comparing the first coordination and the second coordination to the database in real-time.

Clause 83. The method of any of Clauses 71 to 82, further comprising generating a report that summarizes eye coordination patterns of the patient and deviations in the eye coordination patterns.

Clause 84. The method of any of Clauses 71 to 83, further comprising indicating whether the patient satisfies eye coordination requirements for his field of work.

Clause 85. A system for assessing eye coordination, the system comprising: a virtual reality (VR) headset comprising at least one eye-tracking sensor and at least one eye-tracking camera, the at least one eye-tracking sensor and the at least one camera being configured to collect eye movement data of a patient wearing the VR headset; and a computing device in electronic communication with the VR headset, the computing device being configured to cause an object to be displayed at different positions throughout a virtual environment and process the eye movement data to determine the eye coordination of the patient, wherein the eye movement data comprises eye movements of the patient in response to the object being displayed at different positions in the virtual environment.

Clause 86. The system of Clause 85, further comprising a handheld device in electronic communication with the VR headset and the computing device, wherein the patient can use the handheld device to provide input in response to the object being displayed at various positions in the virtual environment.

Clause 87. The system of any of Clauses 85 to 86, wherein the eye movement data collected by the at least one eye-tracking sensor and the at least one eye-tracking camera comprises one or more of angle of eye movement, speed of eye movement, reaction times, and fusing ability of the patient.

Clause 88. The system of any of Clauses 85 to 87, wherein the at least one eye-tracking sensor and the at least one eye-tracking camera are configured collect the eye movement data in real-time and communicate the eye movement data with the computing device in real-time.

Clause 89. The system of any of Clauses 85 to 88, wherein the at least one eye-tracking camera is an infrared camera.

Clause 90. The system of any of Clauses 85 to 89, wherein the computing device comprises a user interface at which a report summarizing the eye movement patterns of the patient can be accessed.

Clause 91. A virtual reality (VR) headset for assessing eye coordination, the VR headset comprising at least one eye-tracking sensor and at least one eye-tracking camera, the at least one eye-tracking sensor and the at least one camera being configured to collect eye movement data of a patient wearing the VR headset.

Clause 92. The VR headset of Clause 91, wherein the eye movement data collected by the at least one eye-tracking sensor and the at least one eye-tracking camera comprises one or more of angle of eye movement, speed of eye movement, reaction times, and fusing ability of the patient.

Clause 93. The VR headset of any of Clauses 91 to 92, wherein the at least one eye-tracking sensor and the at least one eye-tracking camera are configured collect the eye movement data in real-time and communicate the eye movement data with the computing device in real-time.

Clause 94. The VR headset of any of Clauses 91 to 93, wherein the at least one eye-tracking camera is an infrared camera.

Clause 95. A method for testing motion sensitivity, the method comprising: displaying a virtual scene on screens of a virtual reality (VR) headset worn by a patient, wherein the virtual scene comprises continuously moving elements; prompting the patient to provide an input, wherein the input comprises a degree of motion sickness that the patient experiences in response to viewing the virtual scene; processing the input; and comparing the input to a database, wherein the database comprises inputs from individuals with known motion sensitivity statuses.

Clause 96. The method of Clause 95, further comprising: displaying a different virtual scene, wherein the different virtual scene moves in a manner that is different from the virtual scene; prompting the patient to provide an additional input, wherein the additional input comprises the degree of motion sickness that the patient experiences in response to viewing the different virtual scene; processing the additional input; and comparing the additional input to the database.

Clause 97. The method of any of Clauses 95 to 96, further comprising: changing a pixelation direction of each element of the continuously moving elements to suddenly change the movement of the virtual scene; prompting the patient to provide an additional input, wherein the additional input comprises the degree of motion sickness that the patient experiences in response to viewing the continuously moving elements with the changed pixelation direction; processing the additional input; and comparing the additional input to the database.

Clause 98. The method of any of Clauses 95 to 97, further comprising: increasing a speed at which each element of the continuously moving elements moves; prompting the patient to provide an additional input, wherein the additional input comprises the degree of motion sickness that the patient experiences in response to viewing the continuously moving elements with the increased speed; processing the additional input; and comparing the additional input to the database.

Clause 99. The method of any of Clauses 95 to 98, wherein displaying the virtual scene comprises displaying an interactive scene.

Clause 100. The method of any of Clauses 95 to 99, further comprising prompting the patient to navigate through the virtual scene.

Clause 101. The method of any of Clauses 95 to 100, further comprising prompting the patient to provide an additional input, wherein the additional input comprises a description of what the patient perceives in the virtual scene.

Clause 102. The method of any of Clauses 95 to 101, further comprising: displaying one or more rapidly moving objects in the virtual scene; prompting the patient to track the one or more rapidly moving objects with his eyes; monitoring eye movements of the patient; prompting the patient to provide an additional input, wherein the additional input comprises the degree of motion sickness that the patient experiences in responses to tracking the one or more rapidly moving objects; processing the additional input; and comparing the eye movements of the patient and the additional input to the database, wherein the database further comprises eye movements from individuals with known motion sensitivity statuses.

Clause 103. The method of any of Clauses 95 to 102, further comprising: displaying one or more optotypes in the virtual scene; prompting the patient to locate the one or more optotypes; calculating an accuracy with which the patient locates the one or more optotypes; prompting the patient to provide an additional input, wherein the additional input comprises the degree of motion sickness that the patient experiences in responses to locating the one or more optotypes; processing the additional input; and comparing the accuracy and the additional input to the database, wherein the database further comprises accuracy data from individuals with known motion sensitivity statuses.

Clause 104. The method of any of Clauses 95 to 103, wherein processing the input comprises processing the input in real-time.

Clause 105. The method of any of Clauses 95 to 104, wherein comparing the input to the database comprises comparing the input to the database in real-time.

Clause 106. The method of any of Clauses 95 to 105, further comprising generating a report, wherein the report identifies abnormalities in the motion sensitivity of the patient and indicates underlying visual or neurological conditions.

Clause 107. A system for testing motion sensitivity, the system comprising: a virtual reality (VR) headset comprising screens, at least one eye-tracking sensor, and at least one eye-tracking camera, the VR headset being configured to collect motion sensitivity input from a patient wearing the VR headset; and a computing device in electronic communication with the VR headset, the computing device being configured to (a) cause a virtual scene to be displayed on the screens of the VR headset and (b) process the motion sensitivity input to determine the motion sensitivity of the patient, wherein the motion sensitivity input comprises responses from the patient regarding a degree of motion sickness that the patient experiences in response to viewing the virtual scene. The method of Clause 107, further comprising a handheld device in electronic communication with the VR headset and the computing device, wherein the patient can use the handheld device to provide the motion sensitivity input.

Clause 108. The method of Clause 107, further comprising one or more microphones in electronic communication with the VR headset and the computing device, wherein the patient can use the microphone to provide the motion sensitivity input.

Clause 109. The method of any of Clauses 107 to 108, wherein the at least one eye-tracking sensor and the at least one eye-tracking camera are configured to track eye movements of the patient and identify reaction times of the patient.

Clause 110. The method of any of Clauses 107 to 109, wherein the at least one eye-tracking sensor and the at least one eye-tracking camera are configured track the eye movements and identify the reaction times in real-time and communicate corresponding data with the computing device in real-time.

Clause 111. The method of any of Clauses 107 to 110, wherein the at least one eye-tracking camera is an infrared camera.

Clause 112. The method of any of Clauses 107 to 111, wherein the computing device comprises a user interface at which a report summarizing the eye movement patterns of the patient can be accessed.

Clause 113. A virtual reality (VR) headset for testing motion sensitivity, the VR headset comprising: screens configured to display a virtual scene for a patient wearing the VR headset, wherein the virtual scene comprises continuously moving elements; at least one eye-tracking sensor and at least one eye-tracking camera, the at least one eye-tracking sensor and the at least one eye-tracking camera being configured to track eye movements of the patient and identify reaction times of the patient; and one or more microphones configured to receive motion sensitivity input from the patient, wherein the motion sensitivity input comprises responses from the patient regarding a degree of motion sickness that the patient experiences in response to viewing the virtual scene.

Clause 114. The method of Clause 113, wherein the at least one eye-tracking sensor and the at least one eye-tracking camera are configured track the eye movements and identify the reaction times in real-time and communicate corresponding data with the computing device in real-time.

Clause 115. The method of any of Clauses 113 to 114, wherein the at least one eye-tracking camera is an infrared camera.

Clause 116. A method for evaluating spatial awareness by navigating a patient through a virtual scene, the method comprising: displaying a virtual environment on screens of a virtual reality (VR) headset worn by a patient; navigating the patient through the virtual environment at a speed along a path; displaying one or more objects in the virtual environment; receiving an input from the patient while the patient attempts to locate the one or more objects; and comparing the input to a database to evaluate the spatial awareness of the patient, wherein the database comprises inputs from individuals with known spatial awareness statuses.

Clause 117. The method of Clause 116, wherein displaying the virtual environment comprises displaying a maze, and navigating the patient through the virtual environment at the speed along the path comprises navigating the patient through the maze at the speed along the path.

Clause 118. The method of any of Clauses 116 to 117, wherein navigating the patient through the virtual environment comprises changing the virtual environment in real-time.

Clause 119. The method of any of Clauses 116 to 118, further comprising changing the speed and the path as the patient is navigated through the virtual environment.

Clause 120. The method of any of Clauses 116 to 119, wherein the input comprises one or more of head movements of the patient, a spatial orientation of the patient in the virtual environment, a gaze direction of the patient, or visual responses of the patient.

Clause 121. The method of any of Clauses 116 to 120, further comprising continuously monitoring one or more of head movements of the patient, a spatial orientation of the patient in the virtual environment, a gaze direction of the patient, or visual responses of the patient.

Clause 122. The method of any of Clauses 116 to 121, further comprising calculating a percentage of the one or more objects that the patient correctly located.

Clause 123. The method of any of Clauses 116 to 122, wherein calculating the percentage of the one or more objects that the patient correctly located comprises calculating the percentage in real-time as the patient locates the one or more objects.

Clause 124. The method of any of Clauses 116 to 123, wherein comparing the input to the database comprises comparing the input to the database in real-time.

Clause 125. The method of any of Clauses 116 to 124, further comprising generating a report, wherein the report identifies abnormalities in the spatial awareness of the patient.

Clause 126. A method for evaluating spatial awareness by prompting a patient to avoid virtual obstacles, the method comprising: displaying a virtual environment on screens of a virtual reality (VR) headset worn by a patient; navigating the patient through the virtual environment at a speed along a path; displaying one or more obstacles and one or more clearings in the virtual environment along the path; receiving an input from the patient while the patient attempts to avoid the one or more obstacles and locate the one or more clearings; and comparing the input to a database to evaluate the spatial awareness of the patient, wherein the database comprises inputs from individuals with known spatial awareness statuses.

Clause 127. The method of Clause 126, wherein navigating the patient through the virtual environment comprises changing the virtual environment in real-time.

Clause 128. The method of any of Clauses 126 to 127, further comprising changing the speed and the path as the patient is navigated through the virtual environment.

Clause 129. The method of any of Clauses 126 to 128, wherein the input comprises one or more of head movements of the patient, a spatial orientation of the patient in the virtual environment, a gaze direction of the patient, or visual responses of the patient.

Clause 130. The method of any of Clauses 126 to 129, further comprising continuously monitoring one or more of head movements of the patient, a spatial orientation of the patient in the virtual environment, a gaze direction of the patient, or visual responses of the patient.

Clause 131. The method of any of Clauses 126 to 130, further comprising processing the input to determine a reaction time of the patient.

Clause 132. The method of any of Clauses 126 to 131, further comprising calculating a percentage of the one or more obstacles that the patient correctly avoided.

Clause 133. The method of any of Clauses 126 to 132, wherein calculating the percentage of the one or more obstacles that the patient correctly avoided comprises calculating the percentage in real-time as the patient avoids the one or more obstacles.

Clause 134. The method of any of Clauses 126 to 133, wherein comparing the input to the database comprises comparing the input to the database in real-time.

Clause 135. The method of any of Clauses 126 to 134, further comprising generating a report, wherein the report identifies abnormalities in the spatial awareness of the patient.

Clause 136. A method for evaluating spatial awareness by prompting a patient to identify an object from different perspectives, the method comprising: displaying a virtual environment on screens of a virtual reality (VR) headset worn by a patient; displaying an object in the virtual environment, wherein the patient views the object from a first perspective; receiving a first input from the patient while the patient identifies the object from the first perspective; navigating the patient around the virtual environment at a speed such that the patient views the object from a second perspective; receiving a second input from the patient while the patient identifies the object from the second perspective; and comparing the input to a database to evaluate the spatial awareness of the patient, wherein the database comprises inputs from individuals with known spatial awareness statuses.

Clause 137. The method of Clause 136, further comprising changing the speed at which the patient is navigated around the virtual environment.

Clause 138. The method of any of Clauses 136 to 137, further comprising changing one or more of a nature, shape, size, color, brightness, or contrast of the object.

Clause 139. The method of any of Clauses 136 to 138, wherein the input comprises one or more of head movements of the patient, a spatial orientation of the patient in the virtual environment, a gaze direction of the patient, or visual responses of the patient.

Clause 140. The method of any of Clauses 136 to 139, further comprising continuously monitoring one or more of head movements of the patient, a spatial orientation of the patient in the virtual environment, a gaze direction of patient, or visual responses of the patient.

Clause 141. The method of any of Clauses 136 to 140, further comprising processing the input to determine a reaction time of the patient.

Clause 142. The method of any of Clauses 136 to 141, further comprising calculating a percentage of times that the patient correctly identified the object.

Clause 143. The method of any of Clauses 136 to 142, wherein calculating the percentage of times that the patient correctly identified the object comprises calculating the percentage in real-time.

Clause 144. The method of any of Clauses 136 to 143, wherein comparing the input to the database comprises comparing the input to the database in real-time.

Clause 145. The method of any of Clauses 136 to 144, further comprising generating a report, wherein the report identifies abnormalities in the spatial awareness of the patient.

Clause 146. A system for evaluating spatial awareness, the system comprising: a virtual reality (VR) headset comprising screens, at least one eye-tracking sensor, at least one eye-tracking camera, and at least one motion-tracking sensor, the VR headset being configured to collect spatial awareness input from a patient wearing the VR headset; and a computing device in electronic communication with the VR headset, the computing device being configured to (a) cause a virtual environment to be displayed on the screens of the VR headset and (b) process the spatial awareness input to determine the spatial awareness of the patient, wherein the spatial awareness input comprises one or more of head movements of the patient, a spatial orientation of the patient in the virtual environment, a gaze direction of the patient, or visual responses of the patient in response to viewing the virtual environment.

Clause 147. The system of Clause 146, further comprising a handheld device in electronic communication with the VR headset and the computing device, wherein the patient can use the handheld device to provide the spatial awareness input.

Clause 148. The system of any of Clauses 146 to 147, wherein the system is configured to detect a reaction time that is 0.5 seconds or less.

Clause 149. The system of any of Clauses 146 to 148, wherein the system is configured to detect a reaction time that is 0.25 seconds or less.

Clause 150. The system of any of Clauses 146 to 149, wherein the system is configured to detect a reaction time that is 0.13 seconds or less.

Clause 151. The system of any of Clauses 146 to 150, wherein the at least one eye-tracking sensor and the at least one eye-tracking camera are configured to track a gaze direction and the visual responses of the patient.

Clause 152. The system of any of Clauses 146 to 151, wherein the at least one eye-tracking sensor and the at least one eye-tracking camera are configured track a gaze direction and the visual responses in real-time and communicate corresponding data with the computing device in real-time.

Clause 153. The system of any of Clauses 146 to 152, wherein the at least one eye-tracking camera is an infrared camera.

Clause 154. The system of any of Clauses 146 to 153, wherein the at least one motion-tracking sensor is configured to track physical movements and a spatial orientation of the patient.

Clause 155. The system of any of Clauses 146 to 154, wherein the at least one motion-tracking sensor is configured to track physical movements and a spatial orientation of the patient in real-time and communicate corresponding data with the computing device in real-time.

Clause 156. The system of any of Clauses 146 to 155, wherein the computing device comprises a user interface at which a report summarizing the spatial awareness data of the patient can be accessed.

Clause 157. A virtual reality (VR) headset for evaluating spatial awareness, the VR headset comprising: screens configured to display a virtual environment for a patient wearing the VR headset; at least one eye-tracking sensor and at least one eye-tracking camera, the at least one eye-tracking sensor and the at least one eye-tracking camera being configured to track a gaze direction and the visual responses of the patient; and at least one motion-tracking sensor configured to track physical movements and a spatial orientation of the patient.

Clause 158. The VR headset of Clause 157, wherein the at least one eye-tracking sensor and the at least one eye-tracking camera are configured track a gaze direction and the visual responses in real-time and communicate corresponding data with the computing device in real-time.

Clause 159. The VR headset of any of Clauses 157 to 158, wherein the at least one eye-tracking camera is an infrared camera.

Clause 160. The VR headset of any of Clauses 157 to 159, wherein the at least one motion-tracking sensor is configured to track physical movements and a spatial orientation of the patient in real-time and communicate corresponding data with the computing device in real-time.

Clause 161. The VR headset of any of Clauses 157 to 160, wherein the at least one motion-tracking sensor is positioned along a transverse plane of the VR headset, wherein the transverse plane aligns with an eyeline of the patient wearing the VR headset.

Clause 162. The VR headset of any of Clauses 157 to 161, wherein the at least one motion-tracking sensor comprises one motion-tracking sensor on a left side of the VR headset, one motion-tracking sensor on a right side of the VR headset, and at least two motion-tracking sensors on a front side of the VR headset.

Clause 163. The VR headset of any of Clauses 157 to 162, wherein the at least one motion-tracking sensor is configured to track a three-dimensional movement of the head of the patient.

Clause 164. The VR headset of any of Clauses 157 to 163, wherein the at least one motion-tracking sensor comprises one or more of an accelerometer or a gyroscope.

Clause 165. A method for assessing and improving eye-tracking stability and effectiveness, the method comprising: displaying a virtual environment on screens of a virtual reality (VR) headset worn by a patient, wherein the virtual environment comprises one or more objects; monitoring first eye movements of the patient; processing the first eye movements; in response to processing the first eye movements, adjusting the virtual environment displayed on the screens of the VR headset; monitoring the second eye movements of the patient; and comparing one or more of the first and second eye movements to a database to determine an eye-tracking stability and an eye-tracking effectiveness of the patient.

Clause 166. The method of Clause 165, wherein displaying the virtual environment comprises displaying the one or more objects moving in a set manner and adjusting the virtual environment comprises adjusting the set manner.

Clause 167. The method of any of Clauses 165 to 166, wherein displaying the virtual environment comprises displaying a grid.

Clause 168. The method of any of Clauses 165 to 167, wherein the grid comprises squares of a set size, and the method further comprises adjusting the set size of the squares.

Clause 169. The method of any of Clauses 165 to 168, wherein adjusting the virtual environment comprises changing one or more of a brightness, contrast, or saturation of the virtual environment.

Clause 170. The method of any of Clauses 165 to 169, wherein adjusting the virtual environment comprises adjusting the virtual environment in real-time as the first eye movement is processed.

Clause 171. The method of any of Clauses 165 to 170, wherein adjusting the virtual environment comprises increasing a field of vision which the patient is prompted to observe.

Clause 172. The method of any of Clauses 165 to 171, wherein monitoring the first and second eye movements comprises continuously monitoring eye movements of the patient.

Clause 173. The method of any of Clauses 165 to 172, further comprising, before displaying the virtual environment, occluding one eye of the patient.

Clause 174. The method of any of Clauses 165 to 173, further comprising prompting the patient to participate in the assessment while standing.

Clause 175. The method of any of Clauses 165 to 174, further comprising generating a report, wherein the report identifies abnormalities in the eye-tracking stability and eye-tracking effectiveness of the patient.

Clause 176. A method for assessing and improving eye-tracking stability and effectiveness, the method comprising: displaying a shape on screens of a virtual reality (VR) headset worn by a patient, wherein the shape comprises a first pattern; monitoring first eye movements of the patient as the patient tracks the shape; processing the first eye movements; in response to processing the first eye movements, adjusting the shape displayed on the screens such that the shape comprises a second pattern, wherein the second pattern is different from the first pattern; monitoring second eye movements of the patient as the patient tracks the shape; processing the second eye movements; and comparing one or more of the first and second eye movements to a database to determine an eye-tracking stability and an eye-tracking effectiveness of the patient.

Clause 177. The method of Clause 176, wherein displaying the shape comprising the first pattern comprises displaying the shape comprising a grid pattern.

Clause 178. The method of any of Clauses 176 to 177, wherein the grid pattern comprises squares of a set size, and adjusting the shape to comprise the second pattern comprises adjusting the set size of the squares.

Clause 179. The method of any of Clauses 176 to 178, wherein the first pattern comprises a different brightness, contrast, and/or saturation than the second pattern.

Clause 180. The method of any of Clauses 176 to 179, further comprising displaying a first target within the first pattern and a second target within the second pattern, wherein the second target is displayed at a different position on the shape than the first target.

Clause 181. The method of any of Clauses 176 to 180, further comprising monitoring third eye movements of the patient as eyes of the patient travel from the first target to the second target.

Clause 182. The method of any of Clauses 176 to 181, further comprising identifying the different position at which the third eye movements are below a healthy threshold and continuing to display the second target in areas near the different position.

Clause 183. The method of any of Clauses 176 to 182, wherein adjusting the shape comprises replacing the first pattern with the second pattern in real-time as the patient tracks the shape.

Clause 184. The method of any of Clauses 176 to 183, wherein monitoring the first and second eye movements comprises continuously monitoring eye movements of the patient.

Clause 185. The method of any of Clauses 176 to 184, wherein processing the first and second eye movements comprises processing the first and second eye movements in real-time.

Clause 186. The method of any of Clauses 176 to 185, wherein comparing the one or more of the first and second eye movements to the database comprises comparing the one or more of the first and second eye movements to the database in real-time.

Clause 187. The method of any of Clauses 176 to 186, further comprising, before displaying the virtual environment, occluding one eye of the patient.

Clause 188. The method of any of Clauses 176 to 187, further comprising prompting the patient to participate in the assessment while standing.

Clause 189. The method of any of Clauses 176 to 188, further comprising generating a report, wherein the report identifies abnormalities in the eye-tracking stability and eye-tracking effectiveness of the patient.

Clause 190. A system for assessing eye-tracking stability and effectiveness, the system comprising: a virtual reality (VR) headset comprising screens, at least one eye-tracking sensor, at least one eye-tracking camera, and at least one motion-tracking sensor, the VR headset being configured to collect eye tracking data from a patient wearing the VR headset; and a computing device in electronic communication with the VR headset, the computing device being configured to (a) cause a virtual environment to be displayed on the screens of the VR headset and (b) process the eye tracking data to determine an eye-tracking stability and an eye-tracking effectiveness of the patient, wherein the eye tracking data comprises eye movements and/or reaction times of the patient in response to viewing the virtual environment.

Clause 191. The system of Clause 190, further comprising a handheld device in electronic communication with the VR headset and the computing device, wherein the patient can use the handheld device to interact with the virtual environment.

Clause 192. The system of any of Clauses 190 to 191, wherein the at least one eye-tracking sensor and the at least one eye-tracking camera are configured to measure one or more of an angle of eye movements of the patient, a delay in the eye movements of the patient, and a reaction time of the patient.

Clause 193. The system of any of Clauses 190 to 192, wherein the at least one eye-tracking sensor and the at least one eye-tracking camera are configured to measure one or more of an angle of eye movements of the patient, a delay in the eye movements of the patient, and a reaction time of the patient in real-time and communicate corresponding data to the computing device in real-time.

Clause 194. The system of any of Clauses 190 to 193, wherein the at least one eye-tracking camera is an infrared camera.

Clause 195. The system of any of Clauses 190 to 194, wherein the at least one motion-tracking sensor is configured to track physical movements and a spatial orientation of the patient.

Clause 196. The system of any of Clauses 190 to 195, wherein the at least one motion-tracking sensor is configured to track physical movements and a spatial orientation of the patient in real-time and communicate corresponding data with the computing device in real-time.

Clause 197. The system of any of Clauses 190 to 196, wherein the computing device is configured to adjust the virtual environment in response to processing the eye-tracking data.

Clause 198. The system of any of Clauses 190 to 197, wherein the computing device is configured to adjust the virtual environment in real-time as the patient responds to the virtual environment.

Clause 199. The system of any of Clauses 190 to 198, wherein the computing device comprises a user interface at which a report summarizing the spatial awareness data of the patient can be accessed.

Clause 200. A virtual reality (VR) headset for assessing eye-tracking stability and effectiveness, the VR headset comprising: screens configured to display a virtual environment for a patient wearing the VR headset; at least one eye-tracking sensor and at least one eye-tracking camera, the at least one eye-tracking sensor and the at least one eye-tracking camera being configured to collect eye tracking data from the patient; and at least one motion-tracking sensor configured to track physical movements and a spatial orientation of the patient.

Clause 201. The VR headset of Clause 200, wherein the at least one eye-tracking sensor and the at least one eye-tracking camera are configured to measure one or more of an angle of eye movements of the patient, a delay in the eye movements of the patient, and a reaction time of the patient.

Clause 202. The VR headset of any of Clauses 200 to 201, wherein the at least one eye-tracking sensor and the at least one eye-tracking camera are configured to measure one or more of an angle of eye movements of the patient, a delay in the eye movements of the patient, and a reaction time of the patient in real-time and communicate corresponding date//i.e., data about the angle of eye movements, the delay of eye movements, and the reaction time//to the computing device in real-time.

Clause 203. The VR headset of any of Clauses 200 to 202, wherein the at least one eye-tracking camera is an infrared camera.

Clause 204. The VR headset of any of Clauses 200 to 203, wherein the at least one motion-tracking sensor is configured to track physical movements and a spatial orientation of the patient in real-time and communicate corresponding data with the computing device in real-time.

Clause 205. The VR headset of any of Clauses 200 to 204, wherein the at least one motion-tracking sensor is positioned along a transverse plane of the VR headset, wherein the transverse plane aligns with an eyeline of the patient wearing the VR headset.

Clause 206. The VR headset of any of Clauses 200 to 205, wherein the at least one motion-tracking sensor comprises one motion-tracking sensor on a left side of the VR headset, one motion-tracking sensor on a right side of the VR headset, and at least two motion-tracking sensors on a front side of the VR headset.

Clause 207. The VR headset of any of Clauses 200 to 206, wherein the at least one motion-tracking sensor is configured to track a three-dimensional movement of the head of the patient.

Clause 208. The VR headset of any of Clauses 200 to 207, wherein the at least one motion-tracking sensor is configured to track a speed at which the patient moves in three-dimensional space.

Clause 209. The VR headset of any of Clauses 200 to 208, wherein the at least one motion-tracking sensor comprises one or more of an accelerometer or a gyroscope.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

In general, it will be appreciated that the processors can include, by way of example, computers, program logic, or other substrate configurations representing data and instructions, which operate as described herein. In other embodiments, the processors can include controller circuitry, processor circuitry, processors, general purpose single-chip or multi-chip microprocessors, digital signal processors, embedded microprocessors, microcontrollers and the like.

Furthermore, it will be appreciated that in one embodiment, the program logic may advantageously be implemented as one or more components. The components may advantageously be configured to execute on one or more processors. The components include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim.

As used herein, the term "about" is relative to the actual value stated, as will be appreciated by those of skill in the art, and allows for approximations, inaccuracies, and limits of measurement under the relevant circumstances. In one or more aspects, the terms "about," "substantially," and "approximately" may provide an industry-accepted tolerance for their corresponding terms and/or relativity between items.

As used herein, the term "comprising" indicates the presence of the specified integer(s), but allows for the possibility of other integers, unspecified. This term does not imply any particular proportion of the specified integers. Variations of the word "comprising," such as "comprise" and "comprises," have correspondingly similar meanings.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A method of evaluating eye movement, the method comprising:

displaying a virtual environment on screens of a virtual reality (VR) headset worn by a patient;

displaying an object in the virtual environment at a first position;

monitoring a first input of the patient, wherein the first input comprises an eye movement of the patient in response to the object being displayed at the first position;

displaying the object in the virtual environment at a second position, wherein the second position is different from the first position;

monitoring a second input of the patient, wherein the second input comprises the eye movement of the patient in response to the object being displayed at the second position; and comparing one or more of the first and second input to a database;

wherein displaying the object at the first and second positions comprises incrementally adjusting a position of the object in the virtual environment, and wherein the first position is five degrees left of a center point in the virtual environment and the second position is five degrees right of the center point.

2. The method of claim 1, wherein displaying the object at the first and second positions comprises instantly showing the object in the first position, instantly removing the object from the first position, instantly the object in the second position, and instantly removing the object from the second position.

3. The method of claim 1, wherein displaying the object at the first and second positions comprises fading the object into the first position, fading the object out of the first position, fading the object into the second position, and fading the object out of the second position.

4. The method of claim 1, wherein displaying the object at the first and second positions comprises displaying the object as the object travels along a continuous path between the first and second positions.

5. The method of claim 1, wherein monitoring the first and second inputs comprises continuously monitoring the eye movements of the patient.

6. The method of claim 1, wherein monitoring the first and second inputs comprises identifying a delay between the object being displayed at the first and second positions and the eye movement of the patient in response to the object being displayed at the first and second positions.

7. The method of claim 1, wherein comparing one or more of the first and second input to the database comprises comparing one or more of the first and second input to the database in real-time as the patient responds to the object being displayed at the first and second positions.

8. The method of claim 1, further comprising quantifying deviation angles of the eye movements of the patient.

9. The method of claim 8, further comprising calculating a percent difference in the deviation angles of each eye of the patient.

10. The method of claim 9, further comprising recommending evaluation for eye movement disorders if the percent difference is 25% or more.

11. A system for evaluating eye movement, the system comprising:

a virtual reality (VR) headset comprising at least one eye-tracking sensor and at least one eye-tracking camera, the at least one eye-tracking sensor and the at least one camera being configured to collect eye movement data of a patient wearing the VR headset; and a computing device in electronic communication with the VR headset, the computing device being configured to cause an object to be displayed at various positions in a virtual environment and process the eye movement data to identify eye movement patterns of the patient, wherein the eye movement data comprises eye movements of the patient in response to the object being displayed at various positions in the virtual environment, wherein the various positions comprise a first position five degrees left of a center point in the virtual environment and a second position five degrees right of the center point.

12. The system of claim 11, further comprising a handheld device in electronic communication with the VR headset and the computing device, wherein the patient can use the handheld device to provide input in response to the object being displayed at various positions in the virtual environment.

13. The system of claim 11, wherein the eye movement data collected by the at least one eye-tracking sensor and the at least one eye-tracking camera comprises one or more of an accuracy, speed, and coordination of eye movements of the patient.

14. The system of claim 11, wherein the at least one eye-tracking sensor and the at least one eye-tracking camera are configured collect the eye movement data in real-time and communicate the eye movement data with the computing device in real-time.

15. The system of claim 11, wherein the at least one eye-tracking camera is an infrared camera.

16. The system of claim 11, wherein the at least one eye-tracking camera comprises at least two eye-tracking cameras with an eye-tracking camera pointed at each pupil of the patient.

17. The system of claim 11, wherein the computing devices comprises an algorithm that compares the eye movement patterns of the patient to a database to determine whether the eye movement patterns of the patient deviate from healthy ocular motor behavior.

\* \* \* \* \*